US006504007B1

(12) United States Patent
Klein et al.

(10) Patent No.: US 6,504,007 B1
(45) Date of Patent: Jan. 7, 2003

(54) GDNF RECEPTOR

(75) Inventors: Robert D. Klein, South San Francisco; Mark W. Moore, San Francisco; Arnon Rosenthal, Burlingham; Anne M. Ryan, Millbrae, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/860,370

(22) PCT Filed: Mar. 13, 1997

(86) PCT No.: PCT/US97/04363

§ 371 (c)(1),
(2), (4) Date: Jun. 6, 1997

(87) PCT Pub. No.: WO97/33912

PCT Pub. Date: Sep. 18, 1997

Related U.S. Application Data

(63) Continuation-in-part of application No. 08/618,236, filed on Mar. 14, 1996, now abandoned, and a continuation-in-part of application No. 08/615,902, filed on Mar. 14, 1996, now abandoned.

(51) Int. Cl.$^7$ .............................................. C07K 14/71
(52) U.S. Cl. ....................................... 530/350; 930/10
(58) Field of Search .............................. 536/23.1, 23.4, 536/23.5; 435/69.1, 325, 320.1; 530/350; 930/10

(56) References Cited

U.S. PATENT DOCUMENTS 5,550,050 A    8/1996    Holland et al. ........... 435/240.2

FOREIGN PATENT DOCUMENTS

| WO | WO 85/02610   | 6/1985  |
| WO | WO 93/06116   | 10/1994 |
| WO | WO 94/24160 A | 10/1994 |
| WO | WO 95/13376 A | 5/1995  |
| WO | WO 95/05465 A | 12/1995 |
| WO | WO 00/04893 A | 4/2000  |

OTHER PUBLICATIONS

Rudinger in "Petide Hormones" (Ed. J A. Parsons) University Park Press, Baltimore, pp. 1–7, 1976.*
Saarma et al., 11$^{th}$Biennal Meeting of the International Society for Developmental Neuroscience, Tampere, Finland (Jul. 30, 1996–Aug. 3, 1996) Abstract 110, p. 77.
Andres et al., "Expression of two novel eph–related receptor protein tyrosine kinases in mammary gland development and carcinogenesis" Oncogene9(5):1461–1467 (1994).
Barinaga, Marcia "Neurotrophic Factors Enter the Clinic" Science264: 772–774 (May 6, 1994).
Bennett et al., "Cloning and CHaracterization of HTK, a Novel Transmembrane yrosine Kinase o the EPH Sufamily" J. Biol. Chem269(19): 14211–8 (1994).

Berkmeier et al., "Neurotrophin–5: A Novel Neurotrophic Factor That Activates trk and trkB" 7:8570866 (1991).
Buj–Bello et al., "GDNF Is an Age–Specific Survival Factor for Sensory and Autonomic Neurons" Neuron15:821–828 (1995).
Hefti, Franz, "Nerve Growth Factor Promotes Survival of Septal Cholinergic Neurons After Fimbrial Transections" J. Neurosci6:2155–2162 (1986).
Henderson et al., "GDNF: A Potent Survival Factor for Motoneurons Present in Pheripheral Nerve and Muscle" Science266:1062–1064 (1994).
Heumann, Rolf, "Regulation of the Synthesis of Nerve Growth Factor" J. Exp. Biol132:1330150 (1978).
Jackowski, Andre "Neural injury repair: hope for the future as barriers to effective CNS regeneration become clearer" British J. of Neurosurgery9:303–317 (1995).
Jing, Shuqian et al., "GDNF–induced activation of the Ret protein tyrosine kinase is mediated by GDNFR–alpha, a novel receptor for GDNF" Cell85:113–124 (Jun. 28, 1996).
Kaisho et al., "Cloning and expression of a cDNA encoding a novel human neurotrophic factor" FEBS Lett.266:187 (1990).
Kotzbauer et al., "Neurturin, a relative glial–cell–line–derived neurotrophic factor" Nature384:467–470 (1996).
Lai et al., "An Extended Family of Protein–Tyrosine Kinase Genes Differentially Expressed in the Vertebrate Nervous System" Neuron6: 691–704 (1991).
Leibrock et al., "Molecular cloning and expression of brain–derived neurotrophic factor" Nature341:149–152 (1989).
Lin et al., "GDNF: A Glial Cell Line–Derived Neurotrophic Factor for Midbrain Dopaminergic Neurons" Science260:1130–1132 (1993).
Maisonpierre et al., "Ehk–1 and Ehk–2: two novel members of the Eph receptor–like tyrosine kinase family with distinctive structures and neuronal expression" Oncogene8:3277–3268 (1993).
Maisonpierre et al., "Neurotrophin–3: A Neurotrophic Factor Related to NGF and BDNF" Science247:1446 (1990).
Orth, S.R. et al., "Glial cell line–derived Neurotrophic Factor (GDNF) in the kidney" Journal of the American Society of Nephrology6(3):774 (Sep. 1995).

(List continued on next page.)

Primary Examiner—Gary L. Kunz
Assistant Examiner—Robert C. Hayes
(74) Attorney, Agent, or Firm—Knobbe, Martens, Olson & Bear, LLP

(57) ABSTRACT

GDNFRα, GDNFRα extracellular domain (ECD), GDNFRα variants, chimeric GDNFRae (e.g., GDNFRα immunoadhesin), and antibodies which bind thereto (including agonist and neutralizing antibodies) are disclosed. Various uses for these molecules are described, including methods to modulate cell activity and survival by response to GDNFRα-ligands, for example GDNF, by providing GDNFRα to the cell. Also provided are methods for using GDNFRα, GDNF, or agonists thereof, separately or in complex, to treat kidney diseases.

2 Claims, 14 Drawing Sheets-

OTHER PUBLICATIONS

Pasquale et al., "Identification of a developmentally regulated protein–tyrosine kinase by using anti–phoshotyrosibe antibodies to screen a cDNA expression library" *Proc. Natl. Acad. Sci. USA* 86:5449–5453 (1989).

Pasquale, Elena B., "Identification of chicken embryo kinase 5, a developmentally regulated receptor–type tyrosine kinase Of the Eph family" *Cell Regulation* 2:523–534 (1991).

Pichel J.G. et al., "Defects in enteric innervation and kidney development in mice lacking GDNF" *Nature* 382:73–76 (Jul. 4, 1996).

Pichel, J.G. et al., "GDNF is required for kidney development and enteric innervation:" *Cold Spring Harbor Simposia on Quantitative Biology 1996* 61:445–47 (May 1997).

Rosenthal et al., "Primary Structure and Biological Activity of a Novel Human Neurotrophic Factor" *Neuron* 4:767 (1990).

Saarma, M. et al., "Roles of GDNF in the development of nervous system and kidney" International Journal of Development Neuroscience 14(sup.11):77 (1996).

Saijadi et al., "Identification of a New eph–Related Receptor Tyrosine Kinase Gene From Mouse and Chicken That Is Developmentally Regulated and Encodes at Least Two Forms of the Receptor" *New Biol.* 3(8):760–78 (1991).

Schuchardt, A. et al., "Defrects in the kidney and enteric nervous system of mice lacking the Tyrosine kinase Receptor Ret" *Natue* 367:380–383 (Jan. 27, 1994).

Thoenen et al., "Physiology of Nerve Growth Factor" *Annu Rev. Physiol.* 60:284–335 (1980).

Trupp, M. et al. "Peripheral expression and biological activities of GDNF, a new neurotrophic factor for avian and mammalian peripheral neurons" The *Journal of Cell Biology* 130(1):137–148 (Jul. 1, 1995).

Wen, D. et al. "Erythropoietin structure–function relationships: high degree of sequence homology among mammals" *Blood* 82(5):1507–16 (Sep. 1993).

Yan et al. "In vivo neurotrophic effects of GDNF on neonatal and adult facial motor neurons" *Nature* 373:341–244 (Jan. 26, 1995).

\* cited by examiner

```
TTCTATCGAT TGAATTCCCC GGGGATCCTC TAGAGATCCC TCGACCTCGA      50

CCCACGCGTC CGCCGGGCGG CGGCTTTGGA TTTTGGGGGG GCGGGGACCA     100

GCTGCGCGGC GGCACC    ATG TTC CTA GCC ACT CTG TAC TTC      140
                     Met Phe Leu Ala Thr Leu Tyr Phe
                      1               5

GCG CTG CCA CTC CTG GAT TTG CTG ATG TCC GCC GAG GTG        179
Ala Leu Pro Leu Leu Asp Leu Leu Met Ser Ala Glu Val
        10              15              20

AGT GGT GGA GAC CGT CTG GAC TGT GTG AAA GCC AGC GAT        218
Ser Gly Gly Asp Arg Leu Asp Cys Val Lys Ala Ser Asp
                25              30

CAG TGC CTG AAG GAA CAG AGC TGC AGC ACC AAG TAC CGC        257
Gln Cys Leu Lys Glu Gln Ser Cys Ser Thr Lys Tyr Arg
 35              40              45

ACA CTA AGG CAG TGC GTG GCG GGC AAG GAA ACC AAC TTC        296
Thr Leu Arg Gln Cys Val Ala Gly Lys Glu Thr Asn Phe
         50              55              60

AGC CTG ACA TCC GGC CTT GAG GCC AAG GAT GAG TGC CGT        335
Ser Leu Thr Ser Gly Leu Glu Ala Lys Asp Glu Cys Arg
                 65              70

AGC GCC ATG GAG GCC TTG AAG CAG AAG TCT CTG TAC AAC        374
Ser Ala Met Glu Ala Leu Lys Gln Lys Ser Leu Tyr Asn
         75              80              85

TGC CGC TGC AAG CGG GGC ATG AAG AAA GAG AAG AAT TGT        413
Cys Arg Cys Lys Arg Gly Met Lys Lys Glu Lys Asn Cys
                 90              95

CTG CGT ATC TAC TGG AGC ATG TAC CAG AGC CTG CAG GGA        452
Leu Arg Ile Tyr Trp Ser Met Tyr Gln Ser Leu Gln Gly
100             105             110

AAT GAC CTC CTG GAA GAT TCC CCG TAT GAG CCG GTT AAC        491
Asn Asp Leu Leu Glu Asp Ser Pro Tyr Glu Pro Val Asn
        115             120             125
```

FIG. 1A

```
AGC AGG TTG TCA GAT ATA TTC CGG GCA GTC CCG TTC ATA          530
Ser Arg Leu Ser Asp Ile Phe Arg Ala Val Pro Phe Ile
            130                     135

TCA GAT GTT TTC CAG CAA GTG GAA CAC ATT TCC AAA GGG          569
Ser Asp Val Phe Gln Gln Val Glu His Ile Ser Lys Gly
        140                     145                 150

AAC AAC TGC CTG GAC GCA GCC AAG GCC TGC AAC CTG GAC          608
Asn Asn Cys Leu Asp Ala Ala Lys Ala Cys Asn Leu Asp
            155                     160

GAC ACC TGT AAG AAG TAC AGG TCG GCC TAC ATC ACC CCC          647
Asp Thr Cys Lys Lys Tyr Arg Ser Ala Tyr Ile Thr Pro
165                 170                     175

TGC ACC ACC AGC ATG TCC AAC GAG GTC TGC AAC CGC CGT          686
Cys Thr Thr Ser Met Ser Asn Glu Val Cys Asn Arg Arg
            180                     185                 190

AAG TGC CAC AAG GCC CTC AGG CAG TTC TTC GAC AAG GTT          725
Lys Cys His Lys Ala Leu Arg Gln Phe Phe Asp Lys Val
                195                     200

CCG GCC AAG CAC AGC TAC GGG ATG CTC TTC TGC TCC TGC          764
Pro Ala Lys His Ser Tyr Gly Met Leu Phe Cys Ser Cys
        205                     210                 215

CGG GAC ATC GCC TGC ACC GAG CGG CGG CGA CAG ACT ATC          803
Arg Asp Ile Ala Cys Thr Glu Arg Arg Arg Gln Thr Ile
                220                     225

GTC CCC GTG TGC TCC TAT GAA GAA CGA GAG AGG CCC AAC          842
Val Pro Val Cys Ser Tyr Glu Glu Arg Glu Arg Pro Asn
230                     235                     240

TGC CTG AGT CTG CAA GAC TCC TGC AAG ACC AAT TAT ATC          881
Cys Leu Ser Leu Gln Asp Ser Cys Lys Thr Asn Tyr Ile
        245                     250                 255

TGC AGA TCT CGC CTT GCA GAT TTT TTT ACC AAC TGC CAG          920
Cys Arg Ser Arg Leu Ala Asp Phe Phe Thr Asn Cys Gln
                260                     265
```

FIG. 1B

```
CCA GAG TCA AGG TCT GTC AGC AAC TGT CTT AAG GAG AAC        959
Pro Glu Ser Arg Ser Val Ser Asn Cys Leu Lys Glu Asn
    270         Ser 275                     280

TAC GCA GAC TGC CTC CTG GCC TAC TCG GGA CTG ATT GGC        998
Tyr Ala Asp Cys Leu Leu Ala Tyr Ser Gly Leu Ile Gly
            285             290

ACA GTC ATG ACT CCC AAC TAC GTA GAC TCC AGC AGC CTC       1037
Thr Val Met Thr Pro Asn Tyr Val Asp Ser Ser Ser Leu
295             300                 305

AGC GTG GCA CCA TGG TGT GAC TGC AGC AAC AGC GGC AAT       1076
Ser Val Ala Pro Trp Cys Asp Cys Ser Asn Ser Gly Asn
        310             315                 320

GAC CTG GAA GAC TGC TTG AAA TTT CTG AAT TTT TTT AAG       1115
Asp Leu Glu Asp Cys Leu Lys Phe Leu Asn Phe Phe Lys
                325             330

GAC AAT ACT TGT CTC AAA AAT GCA ATT CAA GCC TTT GGC       1154
Asp Asn Thr Cys Leu Lys Asn Ala Ile Gln Ala Phe Gly
    335             340             345

AAT GGC TCA GAT GTG ACC ATG TGG CAG CCA GCC CCT CCA       1193
Asn Gly Ser Asp Val Thr Met Trp Gln Pro Ala Pro Pro
            350             355

GTC CAG ACC ACC ACT GCC ACC ACT ACC ACT GCC TTC CGG       1232
Val Gln Thr Thr Thr Ala Thr Thr Thr Thr Ala Phe Arg
360             365                 370

GTC AAG AAC AAG CCT CTG GGG CCA GCA GGG TCT GAG AAT       1271
Val Lys Asn Lys Pro Leu Gly Pro Ala Gly Ser Glu Asn
        375             380                 385

GAG ATC CCC ACA CAC GTT TTA CCA CCC TGT GCG AAT TTG       1310
Glu Ile Pro Thr His Val Leu Pro Pro Cys Ala Asn Leu
                390             395

CAG GCT CAG AAG CTG AAA TCC AAT GTG TCG GGT AGC ACA       1349
Gln Ala Gln Lys Leu Lys Ser Asn Val Ser Gly Ser Thr
    400             405             410
```

FIG. 1C

| | | | | | | | | | | | | |
|---|---|---|---|---|---|---|---|---|---|---|---|---|
| CAC | CTC | TGT | CTT | TCT | GAT | AGT | GAT | TTC | GGA | AAG | GAT | GGT | 1388 |
| His | Leu | Cys | Leu | Ser | Asp | Ser | Asp | Phe | Gly | Lys | Asp | Gly | |
| | | | 415 | | | | | 420 | | | | | |
| CTC | GCT | GGT | GCC | TCC | AGC | CAC | ATA | ACC | ACA | AAA | TCA | ATG | 1427 |
| Leu | Ala | Gly | Ala | Ser | Ser | His | Ile | Thr | Thr | Lys | Ser | Met | |
| 425 | | | | | 430 | | | | | 435 | | | |
| GCT | GCT | CCT | CCC | AGC | TGC | AGT | CTG | AGC | TCA | CTG | CCG | GTG | 1466 |
| Ala | Ala | Pro | Pro | Ser | Cys | Ser | Leu | Ser | Ser | Leu | Pro | Val | |
| | | 440 | | | | | 445 | | | | | 450 | |
| CTG | ATG | CTC | ACC | GCC | CTT | GCT | GCC | CTG | TTA | TCT | GTA | TCG | 1505 |
| Leu | Met | Leu | Thr | Ala | Leu | Ala | Ala | Leu | Leu | Ser | Val | Ser | |
| | | | | 455 | | | | | 460 | | | | |
| TTG | GCA | GAA | ACG | TCG | TAGCTGCATC | | CGGGAAAACA | | GTATGAAAAG | | | | 1550 |
| Leu | Ala | Glu | Thr | Ser | | | | | | | | | |
| | | 465 | | 468 | | | | | | | | | |

| | | | | |
|---|---|---|---|---|
| ACAAAAGAGA | ACCAAGTATT | CTGTCCCTGT | CCTCTTGTAT | ATCTGAAAAT | 1600 |
| CCAGTTTTAA | AAGCTCCGTT | GAGAAGCAGT | TTCACCCAAC | TGGAACTCTT | 1650 |
| TCCTTGTTTT | TAAGAAAGCT | TGTGGCCCTC | AGGGGCTTCT | GTTGAAGAAC | 1700 |
| TGCTACAGGG | CTAATTCCAA | ACCCATAAGG | CTCTGGGGCG | TGGTGCGGCT | 1750 |
| TAAGGGGACC | ATTTGCACCA | TGTAAAGCAA | GCTGGGCTTA | TCATGTGTTT | 1800 |
| GATGGTGAGG | ATGGTAGTGG | TGATGATGAT | GGTAATTTTA | ACAGCTTGAA | 1850 |
| CCCTGTTCTC | TCTACTGGTT | AGGAACAGGA | GATACTATTG | ATAAAGATTC | 1900 |
| TTCCATGTCT | TACTCAGCAG | CATTGCCTTC | TGAAGACAGG | CCCGCAGCCT | 1950 |
| AGTGTGAATG | ACAAGTGGAG | GTTGGCCTCA | AGAGTGGACT | TGGCAGACTC | 2000 |
| TACCTTGTAG | TAATGTTCAC | CTTTCCGTGT | ATGGTCTCCA | CAGAGTGTTT | 2050 |
| ATGTATTTAC | AGACTGTTCT | GTGATCCCCC | AACAACAACA | ACCACAAATT | 2100 |
| CCTTGGTCAC | CTCCAAATGT | AACCGGTCCT | TTAGCCCAGT | AGAGGAGGGT | 2150 |
| GGGTGTGGCC | CTGGCACAGC | TCCCGGATTG | TTGATGGGCA | CTCTCCTGAG | 2200 |

FIG. 1D

```
CTTTGCTTGA GTGAGAAGCT GAATGTAGCT GAAAATCAAC TCTTCTTACA      2250

CTTAAAAAAA AAAAAAAAAA AAAAAAAAAA AAAAAAAAAA AAAAAAAAAA      2300

AAAAAAAAAA AAAAGGTTTA GGGATAACAG GGTAATGCGG CCGCGTCGAC      2350

CTGCAGAAGC TTGGCCGCCA TGGCCCAA                              2378
```

FIG. 1E

MELATLYFALPLLDLLMSAEVSGGDRLDCVKASDQCLKEQSCSTKYRTLRQCVAGKETNF
SLTSGLEAKDECRSAMEALKQKSLYNCRCKRGMKKEKNCLRIYWSMYQSLQGNDLLEDSP
YEPVNSRLSDIFRAVPFISDVFQQVEHISKGNNCLDAAKACNLDDTCKKYRSAYITPCTT
SMSNEVCNRRKCHKALRQFFDKVPAKHSYGMLFCSCRDIACTERRQTIVPVCSYEERER
PNCLSLQDSCKTNYICRSRLADFFTNCQPESRSVSNCLKENYADCLLAYSGLIGTVMTPN
YVDSSSLSVAPWCDCSNSGNDLEDCLKFLNFFKDNTCLKNAIQAFGNGSDVTMWQPAPPV
QTTATTTAFRVKNKPLGPAGSENEIPTHVLPPCANLQAQKLKSNVSGSTHLCLSDSDF
GKDGLAGASSHITTKSMAAPPSCSLSSLPVLMLTALAALLSVSLAETS

FIG. 2

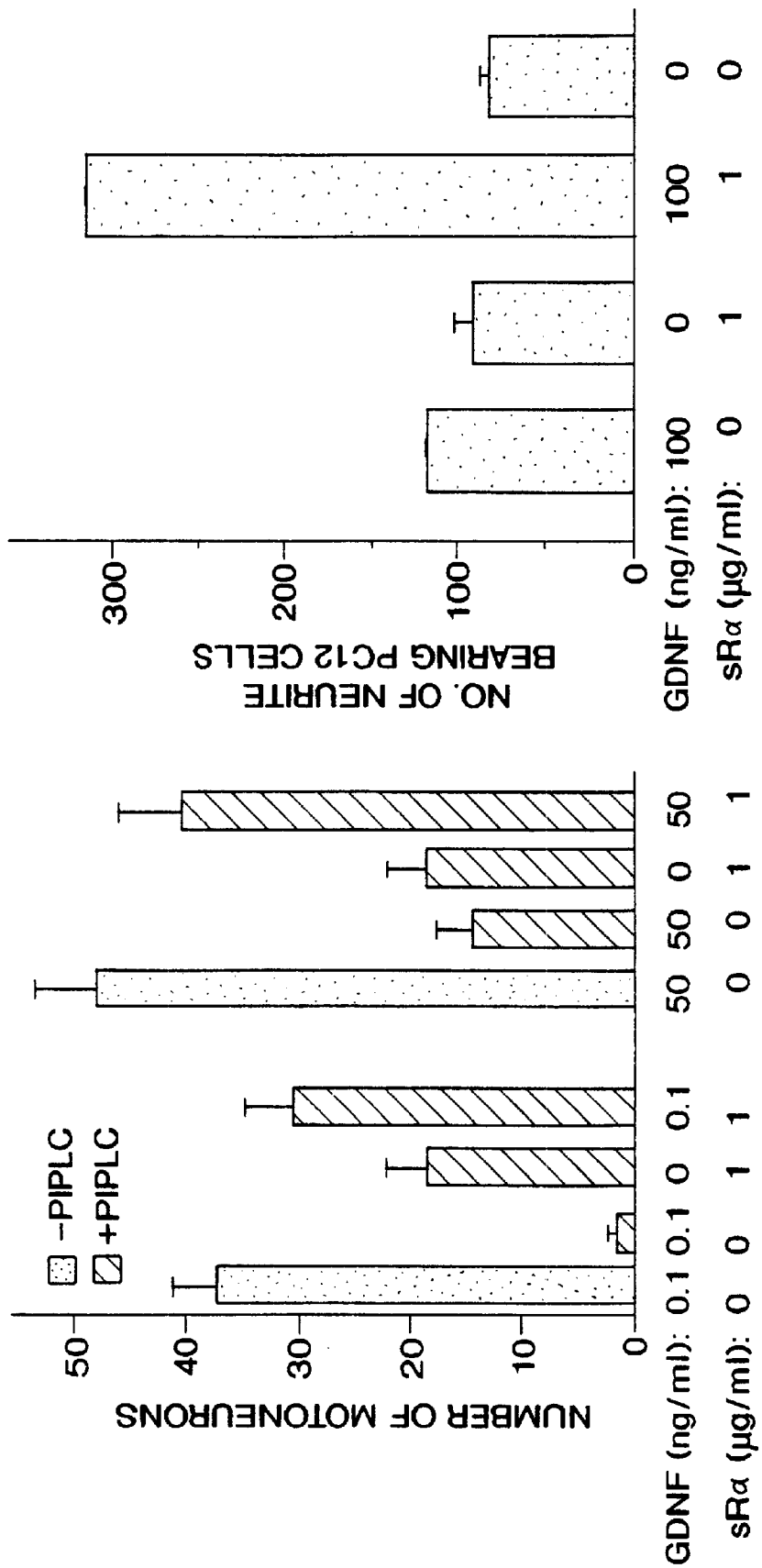

GDNF RECEPTOR

CROSS REFERENCE TO RELATED APPLICATIONS

This application is the National Stage under 35 U.S.C. 371 of International Application No. PCT/US97/04363, filed Mar. 13, 1997, which is a continuation-in-part of Application Nos. 08/615,902, filed Mar. 14, 1996, now abandoned, and 08/618,236, filed Mar. 14, 1996, now abandoned, the entire disclosures of which are incorporated herein by reference.

INTRODUCTION

TECHNICAL FIELD

The present invention relates to novel uses of Glial-cell Derived Neurotrophic Factor ("GDNF") and its receptor designated GDNFRα, and provides GDNFRα-encoding nucleic acid (SEQ ID NO:1) and amino acid sequences (SEQ ID NO:2). In particular, the invention relates to native sequence GDNFRα, GDNFRα variants, soluble GDNFRα variants including GDNFRα extracellular domain, chimeric GDNFRα, and antibodies which bind to the GDNFRα diagnostic techniques for identifying GDNF-related conditions, methods for identifying molecules homologous to GDNFRα, and therapeutic techniques for the treatment of GDNF-related and GDNFRα-related conditions, particularly kidney diseases.

BACKGROUND

Diseases of the nervous system are usually devastating and often lead to death. Neurological diseases are often chronic, which imposes a great social and economic burden. For example, stroke is the third leading cause of death in the United States, after heart disease and cancer. Neurotrophic factors, which are naturally-occurring proteins, such as insulin-like growth factors, nerve growth factor, brain-derived neurotrophic factor, neurotrophin-3, -4/5 and- 6, ciliary neurotrophic factor, GDNF, and recently neurturin, have been proposed as potential means for enhancing specific neuronal cell survival to treat neurological diseases such as amyotrophic lateral sclerosis, Alzheimer's disease, stroke, epilepsy, Huntington's disease, Parkinson's disease, and peripheral neuropathy. Neurotrophic factors, or neurotrophins, which influence growth and development of the vertebrate nervous system, are believed to play an important role in promoting the differentiation, survival, and function of diverse groups of neurons in the brain and periphery. Neurotrophic factors are believed to have important signaling functions in neural tissues, based in part upon the precedent established with nerve growth factor (NGF). NGF supports the survival of sympathetic, sensory, and basal forebrain neurons both in vitro and in vivo. Administration of exogenous NGF rescues neurons from cell death during development. Conversely, removal or sequestration of endogenous NGF by administration of anti-NGF antibodies promotes such cell death (Heumann, *J. Exp. Biol.,* 132:133–150 (1987); Hefti, *J. Neurosci.,* 6:2155–2162 (1986); Thoenen et al., *Annu. Rev. Physiol,* 60:284–335 (1980)).

Additional neurotrophic factors related to NGF have since been identified. These include brain-derived neurotrophic factor (BDNF) (Leibrock, et al., *Nature,* 341:149–152 (1989)), neurotrophin-3 (NT-3) (Kaisho, et al, *FEBS Lett.,* 266:187 (1990); Maisonpierre, et al., *Science,* 247:1446 (1990); Rosenthal, et al., *Neuron,* 4:767 (1990)), and neurotrophin 4/5 (NT-4/5) (Berkmeier, et al., *Neuron,* 7:857–866 (1991)). GDNF, a distant member of the TGF-β super family, and neurturin ("NTN") are two, recently identified, structurally related, potent survival factors for sympathetic sensory and central nervous system neurons (Lin et al. *Science* 260:1130–1132 (1993); Henderson et al. *Science* 266:1062–1064 (1994); Buj-Bello et al., *Neuron* 15:821–828 (1995); Kotzbauer et al. *Nature* 384:467–470 (1996)). GDNF has been considered a potential therapeutic agent for Parkinson's disease, ALS, and Alzheimer's disease. The mechanism by which GDNF and NTN signals are transmitted has not been elucidated.

Neurotrophins, like NGF, affect their target cells through interactions with cell surface receptors. According to our current understanding, two kinds of transmembrane glycoproteins act as receptors for the known neurotrophins. Equilibrium binding studies have shown that neurotrophin-responsive neuronal cells possess a common low molecular weight (65,000–80,000 Daltons), a low affinity receptor typically referred to as $p75^{LNGFR}$ or p75, and a high molecular weight (130,000–150,000 Dalton) receptor. The high affinity receptors (trkA, trkB and trkC) are members of the trk family of receptor tyrosine kinases.

Receptor tyrosine kinases are known to serve as receptors for a variety of protein factors that promote cellular proliferation, differentiation, and survival. In addition to the trk receptors, examples of other receptor tyrosine kinases include the receptors for epidermal growth factor (EGF), fibroblast growth factor (FGF), and platelet-derived growth factor (PDGF). Typically, these receptors span the cell membrane, with one portion of the receptor being intracellular and in contact with the cytoplasm, and another portion of the receptor being extracellular. Binding of a ligand to the extracellular portion of the receptor induces tyrosine kinase activity in the intracellular portion of the receptor, with ensuing phosphorylation of various intracellular proteins involved in cellular signaling pathways.

Aberrant expression of receptor tyrosine kinases ("RTK") correlates with transforming ability. For example, carcinomas of the liver, lung, breast and colon show elevated expression of Eph RTK. Unlike many other tyrosine kinases, this elevated expression can occur in the absence of gene amplification or rearrangement Moreover, Hek, a human RTK, has been identified as a leukemia-specific marker present on the surface of a pre-B cell leukemia cell line. As with Eph, Hek also was overexpressed in the absence of gene amplification or rearrangements in, for example, hemopoietic tumors and lymphoid tumor cell lines. Overexpression of Myk-1 (a murine homolog of human Htk (Bennett et al., *J. Biol. Chem.,* 269(19): 14211–8 (1994)) was found in the undifferentiated and invasive mammary tumors of transgenic mice expressing the Ha-ras oncogene. (Andres et al., *Oncogene,* 9(5):1461–7 (1994) and Andres et al., *Oncogene,* 9(8):2431 (1994)). Ret, the product of the c-ret proto-oncogene, is a member of the receptor tyrosine kinase superfamily.

In addition to their roles in carcinogenesis, a number of transmembrane tyrosine kinases have been reported to play key roles during development. Some receptor tyrosine kinases are developmentally regulated and predominantly expressed in embryonic tissues. Examples include Cek1, which belongs to the FGF subclass, and the Cek4 and Cek5 tyrosine kinases (Pasquale et al., *Proc. Natl. Acad. Sci., USA,* 86:5449–5453 (1989); Sajjadi et al., *New Biol.,* 3(8): 769–78 (1991); and Pasquale, *Cell Regulation,* 2:523–534 (1991). Eph family members are expressed in many different adult tissues, with several family members expressed in the nervous system or specifically in neurons (Maisonpierre et al., *Oncogene*, 8:3277–3288 (1993); Lai et al., *Neuron*, 6:691–704 (1991)).

The aberrant expression or uncontrolled regulation of any one of these receptor tyrosine kinases can result in different malignancies and pathological disorders. Therefore, there exists a need to identify means to regulate, control and manipulate receptor tyrosine kinases ("RTK") and their associated ligands or GPI-linked receptors, in order to provide new and additional means for the diagnosis and therapy of receptor tyrosine kinase pathway-related disorders and cellular processes. The present application provides the clinician and researcher with such means by providing a novel neurotrophin-binding molecule that is also specific for interacting with a particular RTK receptor. New disease conditions are identified that are associated with this molecule and its neurotrophin ligand. These compounds and their methods of use, as provided herein, allow new and exquisite therapeutic control and specificity. Accordingly, it is an object of the present invention to provide an improved therapy for the prevention and/or treatment of neurological conditions and other conditions in which neurotrophic signaling pathways related to this novel receptor and its ligand play a role.

These and other objects of the invention will be apparent to the ordinarily skilled artisan upon consideration of the specification as a whole.

SUMMARY

The present invention is based, in part, on the present discovery that GDNF-deficient mice completely lack kidneys and enteric nervous system and display a partial loss of dorsal root ganglia (<23%) and sympathetic (<35%) and nodose sensory ganglia (<40%) neurons. GDNF-heterozygotes display severe end stage renal disease at an early age. Thus GDNF plays an essential role in the development or survival of the metanephric kidney and enteric neurons. Accordingly, provided are methods of treatment of these and related diseases using GDNF and GDNF-like compounds, optionally in complex or combination with GDNF receptor.

Provided herein are a novel GDNF receptor termed GDNFRα, soluble forms of the receptor, and a GDNFRα extracellular domain ("ECD"). Also disclosed are GDNFRα polypeptides, optionally conjugated with or fused to molecules which increase the serum half-lives thereof, and optionally formulated as pharmaceutical compositions with a physiologically acceptable carrier.

Soluble GDNFRα that retains both ligand binding, preferably GDNF binding, and receptor signaling function (via Ret receptor tyrosine kinase) can be used to impart, restore, or enhance GDNFRα-ligand (preferably GDNF) responsiveness to cells. This responsiveness includes ligand-binding, Ret tyrosine phosphorylation and Ret-mediated downstream activity, which can result in modulation of cell activity such as survival or growth. The embodiments find use in vivo, in vitro or ex vivo. The compounds of the invention find use in treating conditions known to be associated with GDNF as well as the newly identified conditions disclosed herein. GDNFRα ECD that binds GDNF, but does not mediate a GDNF signal, can be used as an antagonist to sequester GDNF ligand to reduce activation of endogenous GDNFRα. This is useful in conditions characterized by excess levels of GDNF ligand and/or excess GDNFRα activation in a mammal.

Pharmaceutical compositions of soluble GDNFRα, preferably ECD, further include an GDNFRα ligand, preferably GDNF. Such compositions, comprising a ligand/GDNFRα complex, are useful where it is desirable to prolong the half-life of the ligand, provide slow, sustained release of ligand, impart GDNFRα-ligand responsiveness to a target cell, and/or activate or enhance endogenous cellular GDNFRα or Ret activity directly. Optionally, the composition further contains one or more cytokines, neurotrophic factors, or their agonist antibodies.

Chimeric GDNFRα molecules such as GDNFRα immunoadhesins (having long serum half-lives) and epitope-tagged GDNFRα are disclosed. These find particular use as soluble forms of GDNFRα, particularly in complexes to deliver GDNF or impart GDNF-responsiveness to cells. Bispecific immunoadhesins (for example, combining a GDNFRα-ligand binding activity with a ligand-binding domain of another cytokine or neurotrophic factor receptor) can form high affinity binding complexes for GDNFRα-ligands in combination with other factors or for targeted delivery.

Also provided are methods for identifying a molecule which binds to and/or activates GDNFRα. Thus assays are provided to screen for or identify GDNFRα-ligand molecules (such as peptides, antibodies, and small molecules) that are agonists or antagonists of GDNFRα. Such methods generally involve exposing an immobilized GDNFRα to a molecule suspected of binding thereto and determining binding of the molecule to the immobilized GDNFRα and/or evaluating whether or not the molecule activates (or blocks activation of) the GDNFRα. In order to identify such GDNF ligands, the GDNFRα can be expressed on the surface of a cell and used to screen libraries of synthetic candidate compounds or naturally-occurring compounds (e.g., from endogenous sources such as serum or cells). GDNFRα can also be used as a diagnostic tool for measuring serum levels of endogenous or exogenous GDNFRα-ligand.

In a further embodiment, a method for purifying an GDNFRα-ligand is provided. This finds use in commercial production and purification of therapeutically active molecules that bind to this receptor. In one embodiment the molecule of interest (generally in a composition comprising one or more contaminants) is adsorbed to immobilized GDNFRα (e.g. GDNFRα immunoadhesin immobilized on a protein A resin). The contaminants, by virtue of their inability to bind to the GDNFRα, will generally not bind the resin. Accordingly, it is then possible to recover the molecule of interest from the resin by changing the elution conditions, such that the ligand molecule is released from the immobilized receptor.

Antibodies are provided that specifically bind to GDNFRα. Preferred antibodies are monoclonal antibodies that are non-immunogenic in a human and bind to an epitope in the extracellular domain of the receptor. Preferred antibodies bind the GDNFRα with an affinity of at least about $10^6$ L/mole, more preferably $10^7$ L/mole. Preferred antibodies are agonist antibodies.

Antibodies, which bind to GDNFRα, can be optionally fused to a heterologous polypeptide. The antibody or fusion finds particular use to isolate and purify GDNFRα from a source of the receptor.

In a further aspect is provided a method for detecting GDNFRα in vitro or in vivo which includes the steps of contacting an GDNFRα antibody with a sample suspected of containing the receptor, and detecting if binding has occurred.

For certain applications it is desirable to have an agonist antibody. Such agonist antibodies are useful for activating GDNFRα as described for GDNFRα-ligands such as GDNF. Furthermore, these antibodies are useful to treat conditions in which an effective amount of GDNFRα activation leads to a therapeutic benefit in the mammal. For example, the agonist antibody can be used to elicit an GDNF response in a cell comprising GDNFRα and, preferably, Ret. For therapeutic applications it is desirable to prepare a composition having the agonist antibody and a physiologically acceptable carrier. Optionally, the composition further contains one or more cytokines, neurotrophic factors, or their agonist antibodies.

In other embodiments, the antibody is a neutralizing antibody. Such molecules can be used to treat conditions characterized by unwanted or excessive activation of GDNFRα.

In addition to the above, the invention provides isolated nucleic acid molecules, expression vectors and host cells encoding GDNFRα, GDNF, or agonist thereof, which can be used in the recombinant production of GDNFRα, GDNF, or agonist thereof, as described herein. The isolated nucleic acid molecules and vectors are also useful to prepare transgenic animals, for gene therapy applications to treat patients with defects in GDNFRα or GDNF, to increase responsiveness of cells to GDNFRα ligands, or alternatively to decrease GDNFRα or GDNF activity (as by use of antisense nucleic acid).

BRIEF DESCRIPTION OF THE DRAWINGS

FIGS. 1A–1E depict the nucleic acid sequence (SEQ ID NO:1) of the sense strand of the cDNA encoding full length GDNFRα and the deduced amino acid sequence (SEQ ID NO:2) of full length GDNFRα. Nucleotides are numbered at the beginning of the sense strand. Amino acid residues are numbered at the beginning of the amino acid sequence.

FIG. 2 depicts the amino acid sequence of GDNFRα (SEQ ID NO:2) and its features. The signal peptide is underlined; the putative signal cleavage site is marked with an arrow; potential glycosylation sites are boxed; the hydrophobic domain element of the GPI attachment site is underlined with a double line; the three underlined amino acids (A-S-S) constitute the GPI-anchor cleavage/attachment site; the cysteines are displayed in boldface. The extracellular domain ("ECD") is flanked by the signal peptide and the GPI-attachment site.

FIGS. 9A, 9B, and 9C depict GDNFRα-dependent GDNF-induced survival of specific neuronal populations. FIG. 9A depicts survival response of embryonic chick nodose, trigeminal, sensory, and sympathetic neurons, rat spinal motoneurons and rat dopaminergic neurons to GDNF or to other growth factors following treatment with PIPLC. PIPLC reduces cell survival in the presence of GDNF or CNTF by 50–90% without changing the response to BDNF, NGF or TGFβ. FIG. 9B depicts increased survival of PIPLC-treated motoneurons in the presence of soluble GDNFRα ("sRα"), which restores the response of the PIPLC-treated motoneurons to GDNF. The trophic activity of GDNFRα alone these experiments is thought to be due to the low levels of GDNF possibly associated with this preparation. FIG. 9C depicts the neurite-outgrowth response of PC12 cells to the combination of soluble GDNFRα (sRα) and GDNF. Soluble GDNFRα imparts GDNF-responsiveness to PC12 cells. The number of neurite bearing live cells per microscopic field is presented.

FIG. 10A depicts GDNF-induced tyrosine autophosphorylation of Ret depends on GDNFRα. Modest stimulation of Ret tyrosine phosphorylation was observed in Neuro-2a and SK-N-SH (SK) cells that were not treated with PIPLC following exposure to GDNF alone (left 2 lanes). Phosphorylation of Ret was further enhanced in the presence of soluble GDNFRα ("+sRα"). No stimulation of Ret phosphorylation was observed in PIPLC-treated cells (+PIPLC) unless GDNF was added together with GDNFRα ("+PIPLC+sRα"). FIG. 10B depicts competition binding of $^{125}I$ GDNF to cells expressing GDNFRα or Ret. GDNF does not bind Ret with a high affinity. FIG. 10C depicts inmunoprecipitation of a GDNF, GDNFRα and Ret complex, which was formed on the cell surface. (Co) untransfected cells. (Ret) cells transfected with Ret alone. (Rα+Ret) cells transfected with Ret and GDNFRα. In all cases cells were exposed to GDNF (100 ng/ml) and then processed for immunoprecipitation with GDNF antisera. The presence of immune complexes between GDNF and Ret was then determined on a Western blot with Ret antisera. GDNF/Ret complex was formed only in the presence of GDNFRα. FIG. 10D depicts immunoprecipitation of a GDNFRα/Ret complex. Complex formation is stimulated by GDNF. (Rα=cells transfected with an epitope tagged GDNFRα alone. (Ret)= cells transfected with Ret alone. (Rα+Ret)=cells transfected with Ret and an epitope tagged GDNFRα. Following transfection, cells were either treated with GDNF (+) or left untreated (−), and then processed for immunoprecipitation with Ret antisera. The presence of immune complexes between Ret and GDNFRα was then determined on a Western blot with anti sera to the epitope tag of GDNFRα. Immune complexes between GDNFRα and Ret were formed in the presence of GDNF.

DETAILED DESCRIPTION

Figure 3:
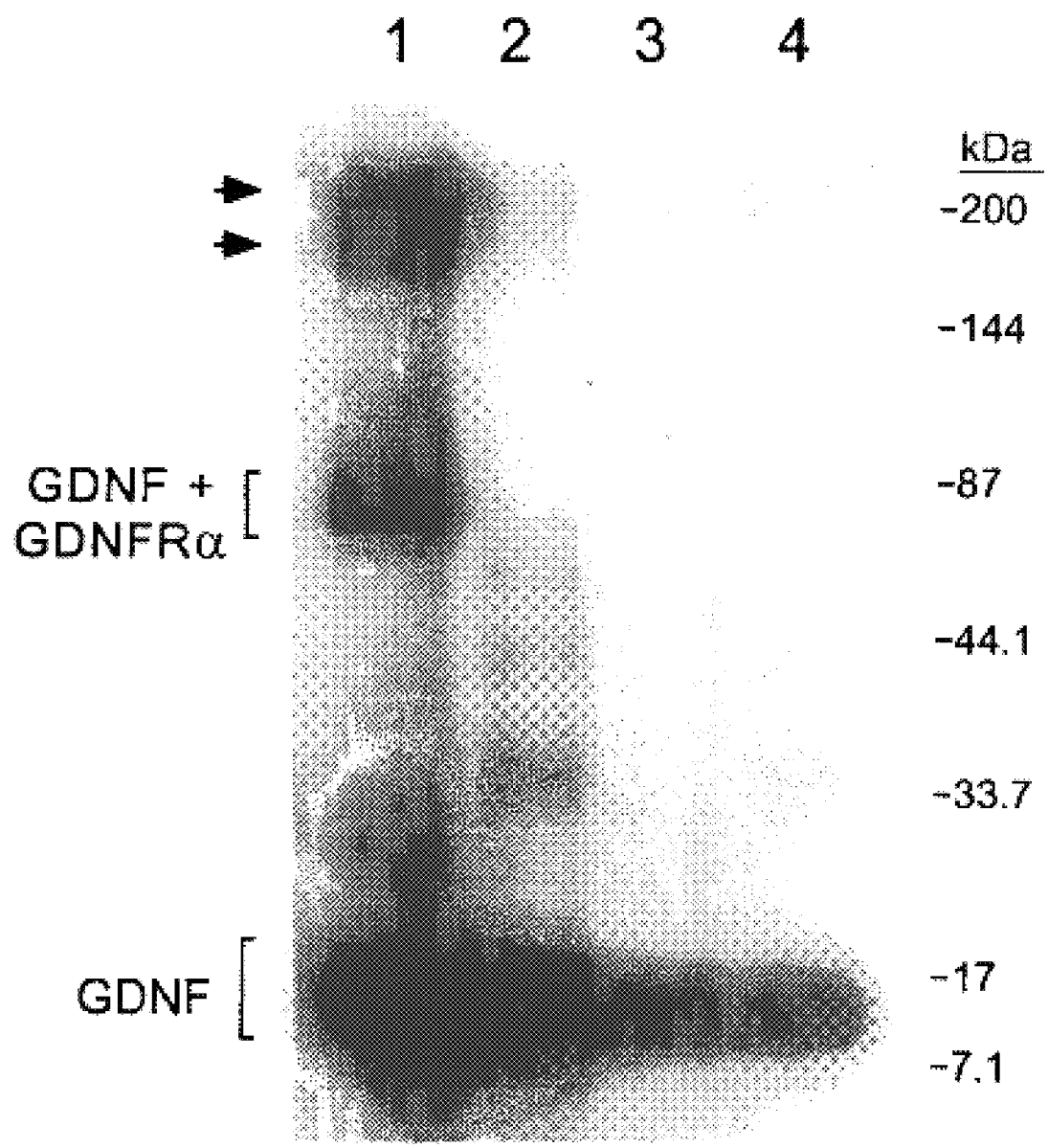
FIG. 3 depicts PAGE results of cross-linking experiments. Depicted are cross-linking of $I^{125}$ GDNF to cells expressing GDNFRα (lanes 1,2) or to control cells (lanes 3, 4) in the absence (lanes 1, 3) or presence (lanes 2, 4) of excess unlabeled GDNF. Cross-linked proteins (~85 kD, ~180 kD, ~200 kD) which are displaceable by unlabeled GDNF are found, in GDNFRα expressing, but not in control cells.

In describing the present invention, the following terms will be employed and are intended to be defined as indicated below.

The terms "GDNFRα" or "GDNFRα polypeptide" when used herein encompass native sequence GDNFRα, GDNFRα variants, GDNFRα extracellular domain, and chimeric GDNFRα (each of which is defined herein). Optionally, the GDNFRα is not associated with native glycosylation. "Native glycosylation" refers to the carbohydrate moieties which are covalently attached to GDNFRα when it is produced in the mammalian cell from which it is derived in nature. Accordingly, human GDNFRα produced in a non-human cell is an example of a GDNFRα which may "not be associated with native glycosylation." Sometimes, the GDNFRα is unglycosylated (e.g., as a result of being produced recombinantly in a prokaryote).

A "native sequence GDNFRα" comprises a polypeptide having the same amino acid sequence as a GDNFRα derived from nature. Thus, a native sequence GDNFRα can have the amino acid sequence of naturally occurring rat GDNFRα, murine GDNFRα, human GDNFRα, or GDNFRα from any other mammalian species. Such native sequence GDNFRα polypeptides can be isolated from nature or can be produced by recombinant or synthetic means. The term "native sequence GDNFRα" specifically encompasses naturally-occurring truncated forms of the GDNFRα, naturally-occurring variant forms (e.g.,alternatively spliced forms), and naturally-occurring allelic variants of the GDNFRα. The preferred native sequence GDNFRα is a mature native sequence GDNFRα. GDNFRα sequence for rat is shown in FIGS. 1A–1E. Preferred molecules are those comprising a nucleic acid molecule that is capable of hybridizing under moderate, and more preferably under stringent hybridization conditions, with the DNA sequence encoding the rat GDNF receptor shown in FIGS. 1A–1E. In one embodiment the GDNFR nucleic acid hybridizes at 42° C. in 20% formamide with the DNA sequence encoding the GDNF receptor shown in FIGS. 1A–1E. In another embodiment a GDNFR nucleic acid molecule is capable of hybridizing at 42° C. in 20% formamide with a DNA sequence of at least 10 contiguous bases, and preferably at least 20 contiguous bases, more preferably with at least 45 bases, and even more preferably with at least 60 bases encoding a portion of the complete GDNF receptor shown in FIGS. 1A–1E. Preferred sequences do not hybridize other known neurotrophin receptor sequences under similar conditions.

Similarly, "GDNF" encompasses native sequence GDNF, GDNF variants, pre-pro-GDNF, mature GDNF, and chimeric GDNF. Optionally, the GDNF is not associated with native glycosylation. GDNF can be unglycosylated (e.g.,as a result of being produced recombinantly in a prokaryote). A "native sequence GDNF" comprises a polypeptide having the same amino acid sequence as a GDNF derived from nature (see Lin et al., Science, 260:1130–1132 (1993) and WO 93/06116, which are incorporated herein in their entirety). Thus, a native sequence GDNF can have the amino acid sequence of naturally occurring rat GDNF, murine GDNF, human GDNF, or GDNF from any other mammalian species. Such native sequence GDNF polypeptides can be isolated from nature or can be produced by recombinant or synthetic means. The term "native sequence GDNFRα" specifically encompasses naturally-occurring truncated forms of the GDNF, naturally-occurring variant forms (e.g., alternatively spliced forms), and naturally-occurring allelic variants of the GDNF. The preferred native sequence GDNF is a mature native sequence human GDNF.

The "GDNFRα extracellular domain" (ECD) is a form of the GDNFRα which is essentially free of the transmembrane and cytoplasmic domains of GDNFRα, i.e., has less than 1% of such domains, preferably 0.5 to 0% of such domains, and more preferably 0.1 to 0% of such domains. Ordinarily, the GDNFRα ECD will have an amino acid sequence having at least about 60% amino acid sequence identity with the amino acid sequence of the ECD of an GDNFRα, for example as indicated in FIGS. 1A–1E for GDNFRα or the corresponding sequences provided herein, e.g. mouse sequences, human sequences, preferably at least about 65%, more preferably at least about 75%, even more preferably at least about 80%, even more preferably at least about 90%, with increasing preference of 95%, to at least 99% amino acid sequence identity, and finally to 100% identity, and thus includes GDNFRα variants as defined below. Preferred sequences will be at least 16 amino acids long, preferably at least 20 amino acids long, and even more preferably at least 40 amino acids long.

"GDNFRα variant" (or "GDNF variant") means a biologically active GDNFRα (or GDNF) as defined below having less than 100% sequence identity (but at least 60% identity) with a GDNFRα (or human GDNF; see Lin et al., Science, 260:1130–1132 (1993); WO 93/06116), for example, having the deduced amino acid sequence shown in FIGS. 1A–1E for GDNFRα or with the sequences provided herein. Such variants include polypeptides wherein one or more amino acid residues are added at the N- or C-terminus of, or within, a GDNFRα or GDNF sequence; from about one to thirty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having about 60% amino acid sequence identity with the amino acid sequence of a naturally-occurring GDNFRα (e.g., as shown in FIGS. 1A–1E or the corresponding sequences provided herein) or human GDNF, preferably at least about 65%, more preferably at least about 75%, even more preferably at least about 80%, even more preferably at least about 90%, with increasing preference of 95%, to at least 99% amino acid sequence identity, and finally to 100% identity. A "chimeric GDNFRα" is a polypeptide comprising full-length GDNFRα or one or more domains thereof (e.g.,the extracellular domain) fused or bonded to heterologous polypeptide. The chimeric GDNFRα will generally share at least one biological property in common with GDNFRα. Examples of chimeric GDNFRα include immunoadhesins and epitope-tagged GDNFRα. A "chimeric GDNF" is a polypeptide comprising mature GDNF fused or bonded to a heterologous peptide, preferably another neurotrophic factor or cytokine.

The term "immunoadhesin" is used interchangeably with the expression "GDNFRα-immunoglobulin chimera" and refers to a chimeric molecule that combines a portion of the GDNFRα (generally the extracellular domain thereof) with an immunoglobulin sequence. The immunoglobulin sequence preferably, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but preferably IgG1 or IgG3.

The term "epitope-tagged" when used herein refers to a chimeric polypeptide comprising GDNFRα (or GDNF) fused to a "tag polypeptide". The tag polypeptide has enough residues to provide an epitope against which an antibody thereagainst can be made, yet is short enough such that it does not interfere with biological activity of the GDNFRα or GDNF. The tag polypeptide preferably also is fairly unique so that the antibody thereagainst does not substantially cross-react with other epitopes. Suitable tag polypeptides generally have at least six amino acid residues and usually between about 8–50 amino acid residues (preferably between about 9–30 residues). Preferred are poly-histidine sequences, which bind nickle, allowing isolation of the tagged protein by Ni-NTA chromatography as described (Lindsay et al. Neuron 17:571–574 (1996)), for example.

"Isolated GDNFRα" or "isolated GDNF" means material that has been purified from a natural source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequential or the best commercially available amino acid sequential marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

"Biological property" when used in conjunction with either "GDNF", "GDNFRα" or "isolated GDNFRα" means having an effector or antigenic function or activity that is directly or indirectly caused or performed by native sequence GDNF or GDNFRα (whether in native or denatured conformation). Effector functions include ligand binding or receptor binding, and enhancement of survival, differentiation and/or proliferation of cells (especially proliferation of cells). However, effector functions do not include possession of an epitope or antigenic site that is capable of cross-reacting with antibodies raised against native sequence GDNF or GDNFRα.

An "antigenic function" means possession of an epitope or antigenic site that is capable of cross-reacting with antibodies raised against native sequence GDNF or GDNFRα. The principal antigenic function of a polypeptide is that it binds with an affinity of at least about $10^6$ L/mole to an antibody raised against native sequence GDNF or GDNFRα. Ordinarily, the polypeptide binds with an affinity of at least about $10^7$ L/mole. The antibodies used to define "antigenic function" are rabbit polyclonal antibodies raised by formulating the antigen in Freund's complete adjuvant, subcutaneously injecting the formulation, and boosting the immune response by intraperitoneal injection of the formulation until the titer of the antibody plateaus.

"Biologically active" when used in conjunction with "GDNF," "GDNFRα " or "isolated GDNFRα" means a polypeptide that exhibits or shares an effector function of native sequence GDNF or GDNFRα and that may (but need not), in addition, possess an antigenic function. A principal effector function of the GDNFRα is its ability to bind GDNF. Another principal effector function of GDNFRα is activating Ret tyrosine kinase (resulting in Ret autophosphorylation) to activate downstream pathways mediated by Ret signaling function.

"Antigenically active" is defined as a polypeptide that possesses an antigenic function of GDNF or GDNFRα and that may (but need not) in addition possess an effector function.

"Percent amino acid sequence identity" is defined herein as the percentage of amino acid residues in the candidate sequence that are identical with the residues in the GDNF or GDNFRα sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the candidate GDNF or GDNFRα sequence shall be construed as affecting sequence identity or homology.

"GDNF ligand" is a molecule which binds to and preferably activates native sequence GDNFRα. The ability of a molecule to bind to GDNFRα can be determined, for example, by the ability of the putative ligand to bind to GDNFRα immunoadhesin coated on an assay plate, for example. Specificity of binding can be determined by comparing binding to other neurotrophic factor or cytokine receptors, particularly of the TGF-βsuper family. Differential binding of at least two fold should be observed. The ability to compete with binding of GDNF to GDNFRα is a preferred property of a GDNF ligand. The thymidine incorporation assay provides another means for screening for ligands which activate GDNFRα function.

A "thymidine incorporation assay" can be used to screen for molecules which activate the GDNFRα. In order to perform this assay, IL-3 dependent Baf3 cells (Palacios et al., Cell, 41:727–734 (1985)) are stably transfected with full length native sequence GDNFRα as described herein and Ret. The GDNFRα/Ret/Baf3 cells so generated are starved of IL-3 for 24 hours in a humidified incubator at 37° C. in 5%$CO_2$ and air. Following IL-3 starvation, the cells are plated out in 96 well culture dishes with, or without, a test sample containing a potential agonist (such test samples are optionally diluted) and cultured for 24 hours in a cell culture incubator 20 μl of serum free RPMI media containing 1 μCi of $^3$H thymidine is added to each well for the last 6–8 hours. The cells are then harvested in 96 well filter plates and washed with water. The filters are then counted using a Packard Top Count Microplate Scintillation Counter, for example. Agonists are expected to induce a statistically significant increase (to a P value of 0.05) in $^3$H uptake, relative to control. Preferred agonists leads to an increase in 3H uptake which is at least two fold of that of the control. Other assays are described herein.

An "isolated" nucleic acid molecule is a nucleic acid molecule that is identified and separated from at least one contaminant nucleic acid molecule with which it is ordinarily associated in the natural source of the GDNF or GDNFRα nucleic acid. An isolated nucleic acid molecule is other than in the form or setting in which it is found in nature. Isolated nucleic acid molecules therefore are distinguished from the nucleic acid molecule as it exists in natural cells. However, an isolated GDNFRα (or GDNF) nucleic acid molecule includes GDNFRα (or GDNF) nucleic acid molecules contained in cells that ordinarily express GDNFRα (or GDNF) where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256: 495 (1975), or may be made by recombinant DNA methods (see, e.g., U.S. Pat. No. 4,816,567 (Cabilly et al.)). The "monoclonal antibodies" may also be isolated from phage antibody libraries using the techniques described in Clackson et al., 624–628 (1991) and Marks et al., *J. Mol. Biol.,* 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass while the remainder of the chain(s) is identical with or homologous to corresponding sequences in antibodies derived from another species or belonging to another antibody class or subclass, as well as fragments of such antibodies, so long as they exhibit the desired biological activity (Cabilly et al, supra; Morrison et al., *Proc, Natl. Acad. Sci.* USA, 81:6851–6855 (1984)).

"Humanized" formns of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature,* 321:522–525 (1986); Reichmann et al., *Nature,* 332:323–329 (1988); and Presta, *Curr. Op. Struct. Biol.,* 2:593–596 (1992). The humanized antibody includes a Primatized™ antibody wherein the antigen-binding region of the antibody is derived from an antibody produced by immunizing macaque monkeys with the antigen of interest.

"Non-immunogenic in a human" means that upon contacting the polypeptide of interest in a physiologically acceptable carrier and in a therapeutically effective amount with the appropriate tissue of a human, no state of sensitivity or resistance to the polypeptide of interest is demonstrable upon the second administration of the polypeptide of interest after an appropriate latent period (e.g., 8 to 14 days).

By "agonist antibody" is meant an antibody which is a GDNFRα ligand, able to activate native sequence GDNFRα.

A "neutralizing antibody" is one which is able to block or significantly reduce an effector function of native sequence GDNF or GDNFRα. For example, a neutralizing antibody may inhibit or reduce GDNFRα activation by a GDNF ligand, as determined, for example, in a neurite survival assays, a GDNF binding assay, or other assays taught herein or known in the art.

The phrase "enhancing proliferation of a cell" encompasses the step of increasing the extent of growth and/or reproduction of the cell relative to an untreated cell either in vitro or in vivo. An increase in cell proliferation in cell culture can be detected by counting the number of cells before and after exposure to a molecule of interest. The extent of proliferation can be quantified via microscopic examination of the degree of confluency. Cell proliferation can also be quantified using the thymidine incorporation assay described herein.

By "enhancing differentiation of a cell" is meant the act of increasing the extent of the acquisition or possession of one or more characteristics or functions which differ from that of the original cell (i.e. cell specialization). This can be detected by screening for a change in the phenotype of the cell (e.g., identifying morphological changes in the cell).

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

As used herein, the term "salvage receptor binding epitope" refers to an epitope of the Fc region of an IgG molecule (e.g., IgG1, IgG2, IgG3, and IgG4) that is responsible for increasing the in vivo serum half-life of the IgG molecule. Exemplary salvage receptor binding epitope sequences include HQNLSDGK(SEQ ID NO:3); HQNISDGK(SEQ ID NO:4); HQSLGTQ(SEQ ID NO:5); VISSHLGQ(SEQ ID NO:6); and PKNSSMISNTP(SEQ ID NO:7).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); neurotrophic factors or nerve growth factors such as NGF-β, NT-3, NT-4, NT-6, BDNF, CNTF, GDNF, AL-1 and other eph-receptor family ligands; platelet-growth factor; transforming growth factors (TGFs) such as TGF-α and TGF-β; insulin-like growth factor-I and -II; erythropoietin (EPO); osteoinductive factors; interferons such as interferon-α,-β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1,IL-α, IL-2, IL-3, IL-4, IL-5, IL-6, IL-7, IL-8, IL-9, IL-I 1, IL-12; and other polypeptide factors including LIF and kit ligand (KL). As used herein, the term cytokine includes proteins from natural sources or from recombinant cell culture and biologically active equivalents of the native sequence cytokines. Also included are genetically engineered molecules with cytokine activity such as TrkA-IgG or other soluble receptor chimeras.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

By "solid phase" is meant a non-aqueous matrix to which a reagent of interest (e.g.,the GDNFRα or an antibody thereto) can adhere. Examples of solid phases encompassed herein include those formed partially or entirely of glass (e.g.,controlled pore glass), polysaccharides (e.g.,agarose), polyacrylamides, polystyrene, polyvinyl alcohol and silicones. In certain embodiments, depending on the context, the solid phase can comprise the well of an assay plate; in others it is a purification column (e.g.,an affinity chromatography column). This term also includes a discontinuous solid phase of discrete particles, such as those described in U.S. Pat. No. 4,275,149.

Modes for carrying out the invention are presented herein. GDNF (Lin et al., *Science*, 260:1130–1132 (1993); WO 93/06116, which are incorporated herein in their entirety) is a potent survival factor for midbrain dopaminergic (Lin et al., *Science*, 260:1130–1132 (1993); Stromberg et al., *Exp. Neurol.*, 124:401–412 (1993); spinal motor (Henderson et al., *Science*, 266:1062–1064 (1994)) and noradrenergic neurons (Arenas et al., *Neuron*, 15:1465–1473 (1995)), which degenerate in Parkinson's disease (Hirsch et al., *Nature*, 334:345–348 (1988); Hornykiewicz, *Mt. Sinai J. Med.*, 55:11–20 (1988)), amyotrophic lateral sclerosis (Hirano, Amyotrophic Lateral Sclerosis and Other Motor Neuron Diseases, P. Rowland, ed. (New York: Raven Press, Inc.) pp. 91–101 (1991)), and Alzheimer's disease (Marcynuik et al., *J. Neurol. Sci.*, 76:335–345 (1986); Cash et al., *Neurology*, 37:42–46 (1987); Chan-Palay et al., *Comp. Neurol.*, 287:373–392 (1989)), respectively. Based, in part, on mice genetically engineered to lack GDNF, additional biological roles for GDNF are reported herein: the development and/or survival of enteric, sympathetic, and sensory neurons, and cells of the renal system. The results presented in the examples also demonstrates that GDNF is not necessary for catecholaminergic neuron development in the central nervous system (CNS).

Also described herein is the isolation, sequence, and tissue distribution of a novel GPI-linked protein and its gene, designated GDNFRα, which is shown to modulate cell response to GDNF. Ligand bound GDNFRα induces phosphorylation of the tyrosine kinase receptor Ret. These findings identify Ret and GDNFRα, respectively, as signaling and ligand binding components of a receptor complex for GDNF.

Cytokine receptors frequently assemble into multi-subunit complexes. Sometimes, the a subunit of this complex is involved in binding the cognate growth factor and the β-subunit may contain an ability to transduce a signal to the cell. Without wishing to be bound by theory, these receptors have been assigned to three subfamilies depending on the complexes formed. Subfamily 1 includes the receptors for EPO, granulocyte colony-stimulating factor (G-CSF), interleukin-4 (IL-4), interleukin-7 (IL-7), growth hormone (GH), and prolactin (PRL). Ligand binding to receptors belonging to this subfamily is thought to result in homodirnerization of the receptor. Subfamily 2 includes receptors for IL-3, granulocyte-macrophage colony-stimulating factor (GM-CSF), interleukin-5 (IL-5), interleukin-6 (IL-6), leukemia inhibitory factor (LIF), oncostatin M (OSM), and ciliary neurotrophic factor (CNTF). Subfamily 2 receptors are heterodimers having an α-subunit for ligand binding, and β-subunit (either the shared β-subunit of the IL-3, GM-CSF, and IL-5 receptors or the gp 130 subunit of the IL-6, LIF, OSM, and CNTF receptors) for signal transduction. Subfamily 3 contains only the interleukin-2 (IL-2) receptor. The β and γ subunits of the IL-2 receptor complex are cytokine-receptor polypeptides which associate with the α-subunit of the unrelated Tac antigen.

In one aspect, the present invention is based on the discovery of the GDNFRα, a protein that binds GDNF with a high affinity. The experiments described herein demonstrate that this molecule is a receptor which appears to play a role in mediating responses to GDNF. In particular, this receptor has been found to be present in a variety of tissue and cell populations, including neurons, thus indicating that GDNF ligands, such as agonist antibodies, can be used to stimulate proliferation, growth, survival, differentiation, metabolism, or regeneration of GDNFRα- and Ret-containing cells.

In a preferred embodiment, GDNF is produced by recombinant DNA methods, utilizing the genes coding for GDNF (see WO 93/06116 for human and rat GDNF sequences, expression, and assay methods). The present invention includes a vector for use in producing biologically active GDNF comprised of expression regulatory elements operatively linked to a nucleic acid sequence coding for mature or pre-pro GDNF, and a host cell transformed by such a vector which comprises the regulatory elements needed to express the DNA sequence; transforming a host cell with said expression vector; culturing the host cells under conditions for amplification of the vector and expression of GDNF; and harvesting the GDNF.

A recombinant DNA method is described for the production of GDNF comprising: culturing the host cells of this invention under conditions for amplification of the vector and expression of GDNF; and harvesting the GDNF.

The material isolated after expression is essentially biologically inactive, and exists as a monomer. Following refolding, GDNF exists as a biologically active disulfide-bonded dimer. GDNF, therefore, is a disulfide-bonded dimer in its natural, biologically active form. This invention, however, includes GDNF in both its monomeric and dimeric, and biologically inactive and biologically active forms.

Throughout the specification, any reference to glial derived neurotrophic factor should be construed to refer to neurotrophic factors of any origin which are substantially homologous to and which are biologically equivalent to the GDNF characterized and described herein. The degree of homology between the rat and human protein is about 93%, and all mammalian GDNF will have a similarly high degree of homology. Such GDNFs may exist as dimers in their biologically active form.

The present invention encompasses glycosylated and non-glycosylated forms of GDNF as well as truncated forms of the naturally-occurring and recombinant GDNF as described herein. In a further embodiment, GDNF is modified by attachment of one or more polyethylene glycol (PEG) or other repeating polymeric moieties. The present invention also encompasses GDNF recombinantly produced in bacterial expression systems containing an amino-terminal methionine residue.

Also included are methods for preventing or treating the disorders discussed herein. In one embodiment is a method of implanting GDNF-secreting cells into the body of patients in need of GDNF-therapy. The implant can optionally contain soluble-GDNFRα-secreting cells. The present invention also includes an implantation device, for preventing or treating the disorders discussed herein, comprising a semipermeable membrane and a GDNF-secreting cell encapsulated within the membrane, which is permeable to GDNF and impermeable to factors from the patient detrimental to the cells.

The description herein for vectors, hosts cells, fusion proteins, modifications, and method and routes of administration, etc. for making, expressing, and using GDNFR applies to GDNF and its variants, as would be known by one of ordinary skill in the art.

Techniques suitable for the production of GDNFRα are well known in the art and include isolating GDNFRα from an endogenous source of the polypeptide, peptide synthesis (using a peptide synthesizer) and recombinant techniques (or any combination of these techniques). The preferred technique for production of GDNFRα is a recombinant technique to be described below.

Most of the discussion below pertains to recombinant production of GDNFRα by culturing cells transformed with a vector containing GDNFRα nucleic acid and recovering the polypeptide from the cell culture. It is further envisioned that the GDNFRα of this invention may be produced by homologous recombination, as provided for in WO 91/06667, published May 16, 1991.

Briefly, this method involves transforming primary human cells containing a GDNFRα-encoding gene with a construct (i.e., vector) comprising an amplifiable gene (such as dihydrofolate reductase (DHFR) or others discussed below) and at least one flanking region of a length of at least about 150 bp that is homologous with a DNA sequence at the locus of the coding region of the GDNFRα gene to provide amplification of the GDNFRα gene. The amplifiable gene must be at a site that does not interfere with expression of the GDNFRα gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifing agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing GDNFRα are grown so as to express the gene and produce the protein.

The conserved structure and sequence of the mammalian GDNFRα and the elucidation of the cDNA sequence which encodes the rat and mouse receptor, as well as human sequences disclosed herein, make it possible to clone gene sequences from other mammals which encode the GDNFRα. Of particular interest to the present invention is the ability to clone the human GDNFRα molecules using the sequences disclosed herein. The DNA encoding GDNFRα may be obtained from any cDNA library prepared from tissue believed to possess the GDNFRα mRNA and to express it at a detectable level, as shown herein in the Examples. Accordingly, GDNFRα DNA can be conveniently obtained from a cDNA library prepared, for example, from mammalian fetal liver, brain, muscle, intestine, and peripheral nerves. The GDNFRα-encoding gene may also be obtained from a genomic library or by oligonucleotide synthesis.

Libraries are screened with probes (such as antibodies to the GDNFRα or oligonucleotides of about 20–80 bases) designed to identify the gene of interest or the protein encoded by it. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989). An alternative means to isolate the gene encoding GDNFRα is to use PCR methodology as described in section 14 of Sambrook et al., supra.

A preferred method of practicing this invention is to use carefully selected oligonucleotide sequences to screen cDNA libraries from various human tissues, preferably human fetal liver. The oligonucleotide sequences selected as probes should be of sufficient length and sufficiently unambiguous that false positives are minimized. Preferred sequences are obtained from the naturally-occurring GDNFRα disclosed herein.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Amino acid sequence variants of GDNFRα are prepared by introducing appropriate nucleotide changes into the GDNFRα DNA, or by synthesis of the desired GDNFRα polypeptide. Such variants represent insertions, substitutions, and/or specified deletions of, residues within or at one or both of the ends of the amino acid sequence of a naturally occurring GDNFRα, such as the GDNFRα shown in FIGS. 1A–1E or sequences disclosed herein. Preferably, these variants represent insertions and/or substitutions within or at one or both ends of the mature sequence, and/or insertions, substitutions and/or specified deletions within or at one or both of the ends of the signal sequence of the GDNFRA. Any combination of insertion, substitution, and/or specified deletion is made to arrive at the final construct, provided that the final construct possesses the desired biological activity as defined herein. The amino acid changes also may alter post-translational processes of the GDNFRα, such as changing the number or position of glycosylation sites, altering the membrane anchoring characteristics, and/or altering the intracellular location of the GDNFRα by inserting, deleting, or otherwise affecting the leader sequence of the GDNFRα. Preferred embodiments are those having several amino substitutions, deletions, or insertions. More preferred substitutions, deletions, or insertions of 1 to 3 amino acids. Most preferred are substitutions, deletions, or insertions of 1 amino acid. Preferred changes are typically conservative in nature.

Variations in the native sequence as described above can be made using any of the techniques and guidelines for conservative and non-conservative mutations set forth in U.S. Pat. No. 5,364,934, which is specifically incorporated by reference. These include oligonucleotide-mediated (site-directed) mutagenesis, alanine scanning, and PCR mutagenesis. See also, for example, Table I therein and the discussion surrounding that table for guidance on selecting amino acids to change, add, or delete.

The nucleic acid (e.g., cDNA or genomic DNA) encoding the GDNFRα is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

The GDNFRαs of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the GDNFRα DNA that is inserted into the vector. The heterologous signal sequence selected preferably is one that is recognized and processed (i.e., cleaved by a signal peptidase) by the host cell. For prokaryotic host cells that do not recognize and process the native GDNFRα signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g. the yeast invertase leader, α factor leader (including Saccharomyces and Kluyveromyces α-factor leaders, the latter described in U.S. Pat. No. 5,010, 182 issued Apr. 23, 1991), or acid phosphatase leader, the *C. albicans* glucoamylase leader (EP 362,179 published Apr. 4, 1990), or the signal described in WO 90/13646 published Nov. 15, 1990. In mammalian cell expression, the native signal sequence (e.g., the GDNFRα presequence that normally directs secretion of GDNFRα from human or rat cells in vivo) is satisfactory, although other mammalian signal sequences may be suitable, such as signal sequences from other animal GDNFRαs, and signal sequences from secreted polypeptides of the same or related species, as well as viral secretory leaders, for example, the herpes simplex gD signal.

The DNA for such precursor region is ligated in reading frame to DNA encoding the mature GDNFRα or a soluble variant thereof.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of GDNFRα DNA. However, the recovery of genomic DNA encoding GDNFRα is more complex than that of an exogenously replicated vector because restriction enzyme digestion is required to excise the GDNFRα DNA.

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the GDNFRα nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes GDNFRα. Amplification is the process by which genes in greater demand for the production of a protein critical for growth are reiterated in tandem within the chromosomes of successive generations of recombinant cells. Increased quantities of GDNFRα are synthesized from the amplified DNA. Other examples of amplifiable genes include metallothionein-I and -II, preferably primate metallothionein genes, adenosine deaminase, ornithine decarboxylase, etc. A preferred vector system is provided in U.S. Pat. No. 5,561,053.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding GDNFRα. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding GDNFRα, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Bianchi et al., *Curr. Genet.*, 12:185 (1987). More recently, an expression system for large-scale production of recombinant calf chymosin was reported for *K. lactis*. Van den Berg, *Bio/Technology*, 8:135 (1990). Stable multicopy expression vectors for secretion of mature recombinant human serum albumin by industrial strains of Kluyveromyces have also been disclosed. Fleer et al., *Bio/Technology*, 9:968–975 (1991).

Expression and cloning vectors usually contain a promoter that is recognized by the host organism and is operably linked to the GDNFRα nucleic acid. Promoters are untranslated sequences located upstream (5') to the start codon of a structural gene (generally within about 100 to 1000 bp) that control the transcription and translation of particular nucleic acid sequence, such as the GDNFRα nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to GDNFRα-encoding DNA by removing the promoter from the source DNA by restriction enzyme digestion and inserting the isolated promoter sequence into the vector. Both the native GDNFRα promoter sequence and many heterologous promoters may be used to direct amplification and/or expression of the GDNFRα DNA. However, heterologous promoters are preferred, as they generally permit greater transcription and higher yields of GDNFRα as compared to the native GDNFRα promoter.

Promoters suitable for use with prokaryotic hosts include the β-lactamase and lactose promoter systems (Chang et al., *Nature,* 275:615 (1978); Goeddel et al., *Nature,* 281:544 (1979)), alkaline phosphatase, a tryptophan (trp) promoter system (Goeddel, *Nucleic Acids Res.,* 8:4057 (1980); EP 36,776), and hybrid promoters such as the tac promoter. deBoer et al., *Proc. Natl. Acad. Sci. USA,* 80:21–25 (1983). However, other known bacterial promoters are suitable. Their nucleotide sequences have been published, thereby enabling a skilled worker operably to ligate them to DNA encoding GDNFRα (Siebenlist et al., *Cell,* 20:269 (1980)) using linkers or adaptors to supply any required restriction sites. Promoters for use in bacterial systems also will contain a Shine-Delgarno (S.D.) sequence operably linked to the DNA encoding GDNFRα.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.,* 255:2073 (1980)) or other glycolytic enzymes (Hess et al., *J. Adv. Enzyme Reg.,* 7:149 (1968); Holland, *Biochemistry,* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

GDNFRα transcription from vectors in mammalian host cells is controlled, for example, by promoters obtained from the genomes of viruses such as polyoma virus, fowlpox virus (UK 2,211,504 published Jul. 5 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the GDNFRα sequence, provided such promoters are compatible with the host cell systems.

The early and late promoters of the SV40 virus are conveniently obtained as an SV40 restriction fragment that also contains the SV40 viral origin of replication. Fiers et al., *Nature,* 273:113 (1978); Mulligan et al., *Science,* 209:1422–1427 (1980); Pavlakis et al., *Proc. Natl. Acad. Sci. USA,* 78:7398–7402 (1981). The immediate early promoter of the human cytomegalovirus is conveniently obtained as a HindIII E restriction fragment. Greenaway et al., *Gene,* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295:503–508 (1982) on expressing cDNA encoding immune interferon in monkey cells; Reyes et al., *Nature,* 297:598–601 (1982) on expression of human β-interferon cDNA in mouse cells under the control of a thymidine kinase promoter from herpes simplex virus; Canaani et al., *Proc. Natl. Acad. Sci. USA,* 79:5166–5170 (1982) on expression of the human interferon β 1 gene in cultured mouse and rabbit cells; and Gorman et al., *Proc. Natl. Acad. Sci. USA,* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of a DNA encoding the GDNFRα of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA,* 78:993 (1981)) and 3' (Lusky et al., *Mol. Cell Bio.,* 3:1108 (1983)) to the transcription unit, within an intron (Banerji et al., *Cell,* 33:729 (1983)), as well as within the coding sequence itself. Osborne et al., *Mol. Cell Bio.,* 4:1293 (1984). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature,* 297:17–18 (1982) on enhancing elements for activation of eukaryotic promoters. The enhancer may be spliced into the vector at a position 5' or 3' to the GDNFRα-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs (Crowley et al. *Cell* 76:1001–1011 (1994)). These regions contain nucleotide segments transcribed as polyadenylated fragments in the untranslated portion of the mRNA encoding GDNFRα.

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9:309 (1981) or by the method of Maxam et al., *Methods in Enzymology*, 65:499 (1980).

Particularly useful in the practice of this invention are expression vectors that provide for the transient expression in mammalian cells of DNA encoding GDNFRα. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of GDNFRα that are biologically active GDNFRα.

Other methods, vectors, and host cells suitable for adaptation to the synthesis of GDNFRα in recombinant vertebrate cell culture are described in Gething et al., *Nature*, 293:620–625 (1981); Mantei et al., *Nature*, 281:40–46 (1979); EP 117,060; and EP 117,058. A particularly useful plasmid for mammalian cell culture expression of GDNFRα is pRK5 (EP 307,247) or pSV16B. WO 91/08291 published Jun. 13, 1991.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coli* 294 (ATCC 31,446), although other strains such as *E. coli* B, *E. coli* X1776(ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonA Δ ptr3phoA Δ E15 Δ(argF-lac)169 ompT Δ degP41kan$^r$ . Strain 27C7 was deposited on Oct. 30, 1991 in the American Type Culture Collection as ATCC No. 55,244. Alternatively, the strain of *E. coli* having mutant periplasmic protease disclosed in U.S. Pat. No. 4,946,783 issued Aug. 7, 1990 may be employed. Alternatively still, methods of cloning, e.g. PCR or other nucleic acid polymerase reactions, are suitable.

In addition to prokaryotes, eukaryotic microbes such as filamentous fungi or yeast are suitable cloning or expression hosts for GDNFRα-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach et al., *Nature*, 290:140 (1981); EP 139,383 published May 2, 1985); Kluyveromyces hosts (U.S. Pat. No. 4,943,529; Fleer et al., supra) such as, e.g. *K. lactis* (MW98–8C, CBS683, CBS4574; Louvencourt et al., *J. Bacteriol.*, 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906, Van den Berg et al., supra), *K. thermotolerans*, and *K. marxianus*; *yarrowia* (EP 402,226); *Pichia pastoris* (EP 183,070; Sreekrishna et al., *J. Basic Microbiol.*, 28:265–278 (1988)); Candida; *Trichoderma reesia* (EP 244,234); *Neurospora crassa* (Case et al., *Proc. Natl. Acad. Sci. USA*, 76:5259–5263 (1979)); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.*, 112:284–289 (1983); Tilburn et al., *Gene*, 26:205–221 (1983); Yelton etal., *Proc. Natl. Acad. Sci. USA*, 81:1470–1474(1984)) and *A. niger*. Kelly et al., *EMBO J.*, 4:475–479 (1985).

Suitable host cells for the expression of glycosylated GDNFRα are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombja mori* have been identified. See, e.g., Luckow et al., *Bio/Technology*, 6:47–55 (1988); Miller et al., in *Genetic Engineering*, Setlow et al., eds., Vol. 8 (Plenum Publishing, 1986), pp. 277–279; and Maeda et al., *Nature*, 315:592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the GDNFRα-encoding DNA. During incubation of the plant cell culture with *A. tumefaciens*, the DNA encoding the GDNFRα is transferred to the plant cell host such that it is transfected, and will, under appropriate conditions, express the GDNFRα-encoding DNA. In addition, regulatory and signal sequences compatible with plant cells are available, such as the nopaline synthase promoter and polyadenylation signal sequences. Depicker et al., *J. Mol. Appl. Gen.*, 1:561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989. However, interest has been greatest in vertebrate cells, and propagation of vertebrate cells in culture (tissue culture) has become a routine procedure. See, e.g., *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/-DHFR (CHO, Urlaub et al., *Proc. Natl. Acad. Sci. USA*, 77:4216(1980)); mouse sertoli cells (TM4, Mather, *Biol. Reprod.*, 23:243–251 (1980)); monkey kidney cells (CV1 ATCC CCL 70); African green monkey kidney cells (VERO-76, ATCC CRL-1587); human cervical carcinoma cells (BELA, ATCC CCL 2); canine kidney cells (MDCK, ATCC CCL 34); buffalo rat liver cells (BRL 3A, ATCC CRL 1442); human lung cells (W138, ATCC CCL 75); human liver 10 cells (Hep G2, 14B 8065); mouse mammary tumor (MMT 060562, ATCC CCL51); TRI cells (Mather et al., *Annals N. Y. Acad. Sci.*, 383:44–68 (1982)); MRC 5 cells; FS4 cells; and a human hepatoma line (Hep G2).

Host cells are transfected and preferably transformed with the above-described expression or cloning vectors for GDNFRα production and cultured in conventional nutrient media modified as appropriate for inducing promoters, selecting transformants. or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham et al., *Virology*, 52:456–457 (1978) is preferred. General aspects of mammalian cell host system transformations have been described in U.S. Pat. No. 4,399,216 issued Aug. 16, 1983. Transformations into yeast are typically carried out according to the method of Van Solingen et al., *J. Bact.*, 130:946 (1977) and Hsiao et al., *Proc. Natl. Acad. Sci. USA*, 76:3829(1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology*, 185:527–537 (1990) and Mansour et al., *Nature*, 336:348–352 (1988).

Prokaryotic cells used to produce the GDNFRα polypeptide of this invention are cultured in suitable media as described generally in Sambrook et al., supra.

The mammalian host cells used to produce the GDNFRα of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al. *Meth. Enz.*, 58:44 (1979), Barnes et al., *Anal. Biochem.*,102:255 (1980), U.S. Pat. Nos. 4,767,704; 4,657,866; 4,927,762; 4,560,655; or U.S. Pat. No. 5,122,469; WO 90/03430; WO 87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are maintained within a host animal.

Gene amplification and/or expression may be measured in a sample directly, for example, by conventional Southern blotting, Northern blotting to quantitate the transcription of mRNA (Thomas, *Proc. Natl. Acad. Sci. USA*, 77:5201–5205 (1980)), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, can be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.,* 75:734–738 (1980).

Antibodies useful for immunohistochemical staining and/or assay of sample fluids may be either monoclonal or polyclonal, and may be prepared as described herein.

GDNFRα (e.g., GDNFRα ECD) preferably is recovered from the culture medium as a secreted polypeptide, although it also may be recovered from host cell lysates. If the GDNFRα is membrane-bound, it can be released from the membrane using a suitable detergent solution (e.g. Triton-X 100).

When GDNFRα is produced in a recombinant cell other than one of human origin, the GDNFRα is completely free of proteins or polypeptides of human origin. However, it is necessary to purify GDNFRα from recombinant cell proteins or polypeptides to obtain preparations that are substantially homogeneous as to GDNFRα. As a first step, the culture medium or lysate can be centrifuged to remove particulate cell debris. GDNFRα can then be purified from contaminant soluble proteins and polypeptides with the following procedures, which are exemplary of suitable purification procedures: by fractionation on an ion-exchange column; ethanol precipitation; reverse phase HPLC; chromatography on silica; chromatofocusing; immunoaffinity; epitope-tag binding resin; SDS-PAGE; ammonium sulfate precipitation; gel filtration using, for example, Sephadex G-75; and protein A Sepharose columns to remove contaminants such as IgG.

GDNFRα variants in which residues have been deleted, inserted, or substituted are recovered in the same fashion as native sequence GDNFRα, taking account of any substantial changes in properties occasioned by the variation. Immunoaffmity resins, such as a monoclonal anti-GDNFRα resin, can be employed to absorb the GDNFRα variant by binding it to at least one remaining epitope.

A protease inhibitor such as phenyl methyl sulfonyl fluoride (PMSF) also may be useful to inhibit proteolytic degradation during purification, and antibiotics may be included to prevent the growth of adventitious contaminants.

Covalent modifications of GDNFRα polypeptides are included within the scope of this invention. Both native sequence GDNFRα and amino acid sequence variants of the GDNFRα may be covalently modified. One type of covalent modification of the GDNFRα is introduced into the molecule by reacting targeted amino acid residues of the GDNFRα with an organic derivatizing agent that is capable of reacting the N-terminal residue, the C-terminal residue, or with selected side chains.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing -amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed under alkaline conditions because of the high $PK_a$ of the guanidine functional group. Furthermore, these reagents may react with the groups of lysine as well as with the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking GDNFRα to a water-insoluble support matrix or surface for use in the method for purifying anti-GDNFRα antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-((p-azidophenyl)dithio) propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties,* W. H. Freeman & Co., San Francisco, pp. 79–86 (1983)), acetylation of the N-terminal amine, and amidation of any C-terminal carboxyl group.

Another type of covalent modification of the GDNFRα polypeptide included within the scope of this invention comprises altering the native glycosylation pattern of the polypeptide. By altering is meant deleting one or more carbohydrate moieties found in native GDNFRα, and/or adding one or more glycosylation sites that are not present in the native GDNFRα.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the GDNFRα polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native GDNFRα sequence (for O-linked glycosylation sites). For ease, the GDNFRα amino acid sequence is preferably altered through changes at the DNA level, particularly by mutating the DNA encoding the GDNFRα polypeptide at preselected bases such that codons are generated that will translate into the desired amino acids. The DNA mutation(s) may be made using methods described above and in U.S. Pat. No. 5,364,934, supra.

Another means of increasing the number of carbohydrate moieties on the GDNFRα polypeptide is by chemical or enzymatic coupling of glycosides to the polypeptide. These procedures are advantageous in that they do not require production of the polypeptide in a host cell that has glycosylation capabilities for N-linked or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87105330 published Sep. 11, 1987, and in Aplin et al., *CRC Crit. Rev. Biochem.*, 259–306 (1981).

Removal of carbohydrate moieties present on the GDNFRα polypeptide may be accomplished chemically or enzymatically. Chemical deglycosylation requires exposure of the polypeptide to the compound trifluoromethane-sulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol,* 138:350 (1987).

Glycosylation at potential glycosylation sites may be prevented by the use of the compound tunicamycin as described by Duskin et al., *J. Biol. Chem.,* 257:3105 (1982). Tunicamycin blocks the formation of protein-N-glycoside linkages.

Another type of covalent modification of GDNFRα comprises linking the GDNFRα polypeptide to one of a variety of nonproteinaceous polymers, e.g. polyethylene glycol, polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337.

Variants can be assayed as taught herein. A change in the immunological character of the GDNFRα molecule, such as affinity for a given antibody, can be measured by a competitive-type immunoassay. Other potential modifications of protein or polypeptide properties such as redox or thermal stability, hydrophobicity, susceptibility to proteolytic degradation, or the tendency to aggregate with carriers or into multimers are assayed by methods well known in the art.

This invention encompasses chimeric polypeptides comprising GDNFRα fused to a heterologous polypeptide. A chimeric GDNFRα is one type of GDNFRα variant as defined herein. In one preferred embodiment, the chimeric polypeptide comprises a fusion of the GDNFRα with a tag polypeptide which provides an epitope to which an anti-tag antibody or molecule can selectively bind. The epitope-tag is generally provided at the amino- or carboxyl- terminus of the GDNFRα. Such epitope-tagged forms of the GDNFRα are desirable, as the presence thereof can be detected using a labeled antibody against the tag polypeptide. Also, provision of the epitope tag enables the GDNFRα to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., *Mol. Cell. Biol.,* 8:2159–2165 (1988)); the c-myc tag and the 8F9, 3C7, 6E10, G4, B7 and 9E10 antibodies thereto (Evan et al., *Molecular and Cellular Biology,* 5:3610–3616 (1985)); and the Herpes Simplex virus glycoprotein D (gD) tag and its antibody. Paborsky et al., *Protein Engineering,* 3(6): 547–553 (1990). Other tag polypeptides have been disclosed. Examples include the Flag-peptide (Hopp et al., *BioTechnology,* 6:1204–1210 (1988)); the KT3 epitope peptide (Martin et al., *Science,* 255:192–194 (1992)); an α-tubulin epitope peptide (Skinner et al., *J. Biol. Chem.,* 266:15163–15166 (1991)); and the T7 gene 10 protein peptide tag. Lutz-Freyernuth et al., *Proc. Natl. Acad. Sci. USA,* 87:6393–6397 (1990). Once the tag polypeptide has been selected, an antibody thereto can be generated using the techniques disclosed herein. A C-terminal poly-histidine sequence tag is preferred. Poly-histidine sequences allow isolation of the tagged protein by Ni-NTA chromatography as described (Lindsay et al. *Neuron* 17:571–574 (1996)), for example.

The general methods suitable for the construction and production of epitope-tagged GDNFRα are the same as those disclosed hereinabove. GDNFRα-tag polypeptide fusions are most conveniently constructed by fusing the cDNA sequence encoding the GDNFRα portion in-frame to the tag polypeptide DNA sequence and expressing the resultant DNA fusion construct in appropriate host cells. Ordinarily, when preparing the GDNFRα-tag polypeptide chimeras of the present invention, nucleic acid encoding the GDNFRα will be fused at its 3' end to nucleic acid encoding the N-terminus of the tag polypeptide, however 5' fusions are also possible.

Epitope-tagged GDNFRα can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope-tagged GDNFRα can be eluted from the affinity column by varying the buffer pH or ionic strength or adding chaotropic agents, for example.

Chimeras constructed from a receptor sequence linked to an appropriate immunoglobulin constant domain sequence (immunoadhesins) are known in the art. Immunoadhesins reported in the literature include fusions of the T cell receptor* (Gascoigne et al., *Proc. Natl.Acad. Sci. USA*, 84: 2936–2940 (1987)); CD4* (Capon et al., *Nature* 337: 525–531 (1989); Traunecker et al., *Nature*, 339: 68–70 (1989); Zettmeissl et al., DNA *Cell Biol. USA*, 9: 347–353 (1990); Byrn et al., *Nature*, 344: 667–670 (1990)); L-selectin (homing receptor) ((Watson et al., *J. Cell. Biol.*, 110:2221–2229 (1990); Watson et al., *Nature*, 349: 164–167 (1991)); CD44* (Aruffo et al., *Cell*, 61: 1303–1313 (1990)); CD28* and B7* (Linsley et al., *J. Exp. Med.*, 173: 721–730 (1991); CTLA-4* (Lisley et al., *J. Exp. Med.* 174:561–569 (1991)); CD22* (Stamenkovic et al., *Cell*, 66:1133–1144 (1991)); TNF receptor (Ashkenazi et al., *Proc. Natl. Acad. Sci. USA*, 88: 10535–10539 (1991); Lesslauer et al., *Eur. J. Immunol.*, 27: 2883–2886 (1991); Peppel et al., *J. Exp. Med.*, 174:1483–1489 (1991); NP receptors (Bennett et al., *J. Biol. Chem.* 266:23060–23067 (1991)); and IgE receptor α* (Ridgway et al., *J. Cell. Biol.*, 115:abstr. 1448 (1991)), where the asterisk (*) indicates that the receptor is member of the immunoglobulin superfamily.

The simplest and most straightforward immunoadhesin design combines the binding region(s) of the "adhesin" protein with the hinge and Fc regions of an immunoglobulin heavy chain. Ordinarily, when preparing the GDNFRα-immunoglobulin chimeras of the present invention, nucleic acid encoding the extracellular domain of the GDNFRα will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge and CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the GDNFRα-immunoglobulin chimeras.

In some embodiments, the GDNFRα-immunoglobulin chimeras are assembled as monomers, or hetero- or homo-multimer, and particularly as dimers or tetramers, essentially as illustrated in WO 91/08298.

In a preferred embodiment, the GDNFRα extracellular domain sequence is fused to the N-terminus of the C-terminal portion of an antibody (in particular the Fc domain), containing the effector functions of an immunoglobulin, e.g. immunoglobulin $G_1$ (IgG1). It is possible to fuse the entire heavy chain constant region to the GDNFRα extracellular domain sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the GDNFRα amino acid sequence is fused to the hinge region and CH2 and CH3, or to the CH1, hinge, CH2 and CH3 domains of an IgG1, IgG2, or IgG3 heavy chain. The precise site at which the fusion is made is not critical, and the optimal site can be determined by routine experimentation.

In some embodiments, the GDNFRα-immunoglobulin chimeras are assembled as multimer, and particularly as homo-dimers or-tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Alternatively, the GDNFRV extracellular domain sequence can be inserted between immunoglobulin heavy chain and light chain sequences such that an immunoglobulin comprising a chimeric heavy chain is obtained. In this embodiment, the GDNFRα sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., Mol. Immunol., 28:1027–1037 (1991).

Although the presence of an immunoglobulin light chain is not required in the immunoadhesins of the present invention, an immunoglobulin light chain might be present either covalently associated to an GDNFRα-immunoglobulin heavy chain fusion polypeptide, or directly fused to the GDNFRα extracellular domain. In the former case, DNA encoding an immunoglobulin light chain is typically coexpressed with the DNA encoding the GDNFRα-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued Mar. 28, 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger adhesin domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For GDNFRα immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1 m and 2) are located in the Fc region; and one of these sites GIml, is non-immunogenic. In contrast, there are 12 serologically-defined allotypes in IgG3, all of which are in the Fc region; only three of these sites (G3 m5, 11 and 21) have one allotype which is nonimmunogenic. Thus, the potential immunogenicity of a γ3 immunoadhesin is greater than that of a γ1 immunoadhesin.

With respect to the parental immunoglobulin, a useful joining point is just upstream of the cysteines of the hinge that form the disulfide bonds between the two heavy chains. In a frequently used design, the codon for the C-terminal residue of the GDNFRα part of the molecule is placed directly upstream of the codons for the sequence DKTH-TCPPCP of the IgG1 hinge region.

The general methods suitable for the construction and expression of immunoadhesins are the same as those disclosed hereinabove with regard to GDNFRα. GDNFRα immunoadhesins are most conveniently constructed by fusing the cDNA sequence encoding the GDNFRα portion in-frame to an Ig cDNA sequence. However, fusion to genomic Ig fragments can also be used (see, e.g., Gascoigne et al., *Proc. Natl. Acad. Sci. USA,* 84:2936–2940 (1987); Aruffo et al., *Cell,* 61:1303–1313 (1990); Stamenkovic et al., *Cell,* 66:1133–1144 (1991)). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the GDNFRα and Ig parts of the immunoadhesin are inserted in tandem into a plasmid vector that directs efficient expression in the chosen host cells. For expression in mammalian cells, pRK5-based vectors (Schall et al., *Cell,* 61:361–370 (1990)) and CDM8-based vectors (Seed, *Nature,* 329:840 (1989)) can be used. The exact junction can be created by removing the extra sequences between the designed junction codons using oligonucleotide-directed deletional mutagenesis (Zoller et al., *Nucleic Acids Res.,* 10:6487 (1982); Capon et al., *Nature,* 337:525–531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of GDNFRα immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell,* 61:1303–1313 (1990); Zett-meissl et al., *DNA Cell Biol. US,* 9:347–353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., 1987, supra, Martin et al., *J. Virol,* 67:3561–3568 (1993)).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol. Meth.,* 62:1–13 (1983)). Protein G is recommended for all mouse isotypes and for human γ3 (Guss et al., *EMBO J.,* 5:1567–1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens et al., *Anal. Biochem.,* 159:217–226 (1986)) and immobilized metal chelate chromatography (Al-Mashikhi et al., *J. Dairy Sci.,* 71:1756–1763 (1988)). In contrast to antibodies, however, their behavior on ion exchange columns is dictated not only by their isoelectric points, but also by a charge dipole that may exist in the molecules due to their chimeric nature.

If desired, the immunoadhesins can be made bispecific. Thus, the immunoadhesins of the present invention may combine a GDNFRα extracellular domain and a domain, such as the extracellular domain, of another cytokine or neurotrophic factor receptor subunit. Exemplary cytokine receptors from which such bispecific immunoadhesin molecules can be made include TPO (or mpl ligand), EPO, G-CSF, IL4, IL-7, GH, PRL, IL-3, GM-CSF, IL-5, IL-6, LIF, OSM, CNTF, and IL-2 receptors. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

The GDNFRα protein and GDNFRα gene (and GDNF and GDNF gene) are believed to find ex vivo or in vivo therapeutic use for administration to a mammal, particularly humans, in the treatment of diseases or disorders, related to GDNF activity or benefited by GDNF-responsiveness. Conditions particularly amenable to treatment with the embodiments of the invention are those related to Ret expression or that benefit by Ret activation, particularly of the downstream pathways mediated by Ret. Particularly preferred are neurologic disorders, preferably central nervous system disorders, disorders of the kidney, hematopoietic disorders related to the spleen, and enteric nervous system disorders. In one embodiment the patient is administered an effective amount of GDNFRα, GDNF, or agonist thereof, or active peptide fragment or variant thereof. The present invention also provides for pharmaceutical compositions comprising GDNFRα, GDNF, or agonist thereof, or active peptide fragment or derivative, in a suitable pharmacologic carrier. The material may be administered systemically or locally. Applicable to the methods taught herein, the receptor protein can be optionally administered prior to, after, or preferably concomitantly with (or in complex with) GDNF or other GDNFRαligand. As taught herein, GDNFRα can be provided to target cells in the absence of GDNF to increase the responsiveness of those cells to subsequently administered GDNF or GDNF agonist.

It may be beneficial to decrease the trophic effect of endogenous GDNF. Therefore, in areas of nervous system trauma, it may be desirable to provide GDNF antagonists, including, but not limited to, cell-free GDNFRα defective in Ret activation, which may compete with endogenous cellular receptor for GDNF binding. Under such circumstances, it may be desirable to provide GDNF antagonist locally at the injury site rather than systemically. Use of a GDNFR-providing implant may be desirable for local administration.

Alternatively, certain conditions can benefit from an increase in GDNF (or other GDNFRα-ligand) responsiveness. It may therefore be beneficial to increase the number of or binding affinity of GDNFRα in cells of patients suffering from such conditions. This can be achieved through administration of soluble GDNFRα, optionally complexed with GDNFRα-ligand, preferably GDNF, or by gene therapy using GDNFRα-encoding nucleic acid. Selective expression of recombinant GDNFR in appropriate cells can be achieved using GDNFR genes controlled by tissue specific or inducible promoters or by producing localized infection with replication defective viruses carrying a recombinant GDNFR gene. Conditions which may benefit from increased sensitivity to GDNF include, but are not limited to, motoneuron disorders including amyotrophic lateral sclerosis, Werdnig-Hoffmann disease, chronic proximal spinal muscular atrophy, and Guillain-Barre syndrome. Additional conditions include those involving sympathetic neurons, particularly where increased survival or GDNF-responsiveness is desired. Conditions where increased survival or GDNF-responsiveness of sensory neurons, including peripheral sensory neurons, and central nervous system neurons, including dopaminergic neurons, is desirable, are also suitably treated with embodiments of the invention. Accordingly, treatment of neurological disorders associated with diabetes, Parkinson's disease, Alzheimer's disease, and Huntington's chorea are provided herein. The present compositions and methods can also be applied to conditions related to non-neuronal cells that express GDNFRα. In fact, since GDNFRα serves to activate Ret, conditions associated Ret-activated pathways in Ret-expressing cells can be treated with the embodiments of the invention.

A disease or medical disorder is considered to be nerve damage if the survival or function of nerve cells and/or their axonal processes is compromised. Such nerve damage occurs as the result conditions including: (a) physical injury, which causes the degeneration of the axonal processes and/or nerve cell bodies near the site of the injury; (b) ischemia, as a stroke; (c) exposure to neurotoxins, such as the cancer and AIDS chemotherapeutic agents such as cisplatin and dideoxycytidine (ddC), respectively; (d) chronic metabolic diseases, such as diabetes or renal dysfunction; and (e) neurodegenerative diseases such as Parkinson's disease, Alzheimer's disease, and Amyotrophic Lateral Sclerosis (ALS), which cause the degeneration of specific neuronal populations. Conditions involving nerve damage include Parkinson's disease, Alzheimer's disease, Amyotzphic Lateral Sclerosis, stroke, diabetic polyneuropathy, toxic neuropathy, and physical damage to the nervous system such as that caused by physical injury of the brain and spinal cord or crush or cut injuries to the arm and hand or other parts of the body, including temporary or permanent cessation of blood flow to parts of the nervous system, as in stroke.

The GDNFRα gene is expressed in muscle cells and associated neurons. Accordingly, the present invention provides for methods of treating GDNFR-expressing-muscle cell disorders comprising administering to a patient in need of such treatment the compounds of the invention. Muscle cell disorders which may benefit from such treatment include but are not limited to the following progressive muscular dystrophies: Duchenne, Becker, Emery-Dreifuss, Landouzy-Dejerine, scapulohumeral, limb-girdle, Von Graefe-Fuchs, oculopharyngeal, myotonic and congenital. In addition, such molecules may be of use in the treatment of congenital (central core, nemaline, centronuclear and congenital fiber-type disproportion) and acquired (toxic, inflammatory) myopathies.

In a further embodiment of the invention, patients that suffer from an excess of GDNFR, hypersensitivity to GDNF, excess GDNF, etc. may be treated by administering an effective amount of anti-sense RNA or anti-sense oligodeoxyribonucleotides corresponding to the GDNFR gene coding region thereby decreasing expression of GDNFR.

The compounds and methods of the invention can have use in conditions associated with a decrease in hematopoietic cells. Examples of these diseases include: anemia (including macrocytic and aplastic anemia); thrombocytopenia; hypoplasia; disseminated intravascular coagulation (DIC); myelodysplasia; immune (autoimmune) thrombocytopenic purpura (ITP); and HIV induced ITP. Additionally, GDNF and GDNFRα molecules may be useful in treating myeloproliferative thrombocytotic diseases as well as thrombocytosis from inflammatory conditions and in iron deficiency. GDNF and GDNFRα, which lead to an increase in hematopoietic cell proliferation, can also be used to enhance repopulation of mature blood cell lineages in cells having undergone chemo- or radiation therapy or bone marrow transplantation therapy. Generally, the GDNF and GDNFRα molecules are expected to lead to an enhancement of the proliferation and/or differentiation (but especially proliferation) of hematopoietic cells. Preferred embodiments provide for treatment to enhance hematopoiesis occurring in the spleen.

Other potential therapeutic applications for GDNF and GDNFRα, and their genes, include treatment to promote kidney or liver cell growth, survival, and repair, including are treatment for kidney diseases and disorders. For example, acute renal failure refers to the abrupt disruption of previously normal kidney function. This serious clinical condition can result from a wide variety of mechanisms including circulatory failure (shock), vascular blockage, glomerulonephritis, and obstruction to urine flow. Acute renal failure frequently arises as a complication of abdominal or vascular surgery. Also, low birth weight, high-risk neonates, which may now survive lung and heart problems due to continued improvements in prenatal care, may die from complications of acute renal failure caused by infection or drug toxicity. Of particular clinical importance are cases of acute renal failure associated with trauma, sepsis, postoperative complications, or medication, particularly antibiotics. In particular, the compounds of the invention find use in etiologies, directly or indirectly, related to dysfunction of the enteric nervous system or renal system. Specific conditions affecting the GI include but are not limited to Achalasia, Esophageal spasm, Scleroderma (related to muscular atrophy of the smooth muscle portion of the esophagus, weakness of contraction of the lower two-thirds of the esophageal body, and incompetence of the lower esophageal sphincter, but also caused by treatment with immunosuppressive agents), disorders such as duodenal ulcer, Zollinger-Ellison Syndrome (hypersecretion of acid caused by factors including genetic factors, smoking, neural influences), hypersecretion of gastric acid, malabsorptive disorder for example, in diabetes (and hypoparathyroidism, hyperthyroidism, and adrenal insufficiency) where gastric atony, nausea, vomiting, etc. are at least in part related to dysfunction of the sympathetic/parasympathetic nervous system. Additional disorders include disorders of intestinal motility, including: diverticulosis/diverticulitis; Hirschsprung's disease (a congenital disorder caused by absence of ganglion cells (Meissner's and Auerbach's plexuses) in a small segment of the distal colon, usually near the anus, typically presented in infants, but in less severe cases, may not be diagnosed until adolescence or early adulthood; megacolon of other types (Hirschsprung's is a type of megacolon); intestinal pseudo-obstruction, acute or chronic, which is a severe dysmotility due to abnormalities of sympathetic innervation of the muscle layers of the intestine, or secondarily may result from scleroderma, diabetes, amyloidosis, other neurologic diseases, drugs, or sepsis; and, chronic constipation, which is a serious problem in patients with mental retardation or neurological diseases, wherein a contributing factor is disordered gut motility. Additional conditions include but not limited to: spinal cord dysfunction, due to an obvious disruption of enteric nervous system; Guillain Barre syndrome; Multiple sclerosis; Pandysautonomia (dysfunction of autonomic nervous system); Parkinsonism (frequently associated with disordered gastrointestinal motility); Multiple System Atrophy (Shy Drager Syndrome), which has been documented to have as a feature disordered gut motility; and, porphyria and amyloidosis which are diffuse diseases manifested by neuropathy and often with accompanying GI motility disorders.

The necrosis or damage of GDNFR-expressing or GDNF-responsive tissue treatable with the compositions and methods provided herein, includes necrosis due to microbiologic or viral infection such as viral hepatitis, tuberculosis, typhoid fever, tularemia, brucellosis, yellow fever, and the like, or necrosis due to ischemic injury resulting from shock, heart failure, and the like, or necrosis due to acute or chronic reaction with drugs and toxic substances such as chemotherapeutics, chloroform, carbon tetrachloride, phosphorous poisoning, and the like. As taught herein, the compositions and methods of the invention are useful to treat kidney diseases by providing cellular growth enhancement, including that of renal cells such as renal epithelial cells and neurons innervating the kidney. The compounds and methods of the present invention provide for the repair of kidney damage. Not to be bound by theory, it is believed that this can be accomplished, either directly or indirectly, by stimulating kidney cells, including innervating neurons, to grow and divide. Accordingly, a method for regenerating kidney tissue is provided that includes the steps of preparing a GDNFR agonist (e.g. soluble GDNFRα optionally complexed with GDNF) as disclosed herein, optionally in combination with a pharmacologically acceptable carrier or additional growth factor or cytokine, and contacting the kidney tissue with the composition. A therapeutic amount of the composition is administered. Localized injections or implants are a preferred delivery method. Alternatively, damaged kidneys could be removed, treated ex vivo, and returned to the host after the kidney is repaired.

GDNFR agonists, including GDNF, can be administered during hemodialysis. Hemodialysis is defined as the temporary removal of blood from a patient for the purpose of extracting or separating toxins therefrom and the return of the cleansed blood to the same patient. Hemodialysis is indicated in patients where renal impairment or failure exists, that is, in cases where the blood is not being properly or sufficiently cleansed, (particularly to remove water) by the kidneys. In the case of chronic renal impairment or failure, hemodialysis has to be carried out on a repetitive basis. For example, in end stage kidney disease where transplantation of kidneys is not possible or is contraindicated, the patient will have to be dialyzed about 100 to 150 times per year.

The invention finds use in disorders or conditions that can result in kidney damage. The invention finds use in some immunosuppressive therapies where there is the side-effect of kidney damage, for example, in therapy of IDDM in humans by methods designed to suppress the autoimmune response. Therapy utilizing cyclosporin A in diabetes can result in kidney damage. Diabetes can result in the typical late damages of blood vessels of the kidneys. Other examples include immunologically- or non-immunologically-caused kidney diseases, such as e.g. glomerulonephritis, acute kidney failure, transplant rejection and kidney damage caused by nephrotic substances, kidney transplants, toxic damage to the kidneys. Furthermore, the present invention finds use in organ transplantation, including organ transport for storing any organ enucleated from a donor to insure the protection of the organ at the time of its transplantation, minimizing any trouble occurring until the transplantation operation, and to ensure the preservation of said organ in a good condition. The organ is one having GDNFR-bearing or GDNF-responsive cells. In one specific preferred embodiment, the organ is the kidney. Use or intervention with GDNFR agonist, including GDNF, promises success with regard to the maintenance of the kidney function.

As discussed herein, an object of the invention to provide methods for treatment of mammals with dysfunctional gastrointestinal muscle or disorders of smooth muscles elsewhere in the body. The gastrointestinal muscle is organized and regulated very differently than muscle elsewhere. Both skeletal and smooth muscle in the gastrointestinal tract are under the control of the enteric nervous system which is an extremely complex network of nerves and muscles, that resides within the gastrointestinal wall and orchestrates the entire digestive process including motility, secretion and absorption. The enteric nerves are also organized into interconnected networks called plexuses. Of these, the myenteric plexus, situated between the circular and longitudinal muscle layers, is the main modulator of gastrointestinal motility. It receives input from both the central nervous system (via vagal and sympathetic pathways) as well as from local reflex pathways. Its output consists of both inhibitory and excitatory signals to the adjacent muscle. The final neural pathway regulating muscle activity in the gastrointestinal tract is therefore represented by the neurons of the myenteric plexus. A useful, if somewhat simplistic concept is to visualize net muscle tone in the gastrointestinal tract as that resulting from the balance between the opposing effects of two neuronal systems in the myenteric plexus: one causing the muscle to contract (mainly via acetylcholine) and the other causing it to relax. Both types of neurons, however, are activated by acetylcholine within the myenteric plexus. The role of acetylcholine in the regulation of gastrointestinal muscle tone is therefore complex. Acetylcholine directly released by effector nerves near the muscle causes contraction; however, within the plexus, it may result in inhibition or excitation. This is in contrast to skeletal muscle outside the gastrointestinal tract which is directly innervated by nerves emanating from the central nervous system. The interaction between nerve and muscle in skeletal muscle outside the gastrointestinal tract is far more simple: nerves release acetylcholine which causes the muscle to contract. Finally, the myenteric plexus is probably the most important but not the only determinant of muscle tone in the gastrointestinal tract. In fact, basal smooth muscle tone may be visualized as resulting from the sum of many different factors including intrinsic (myogenic) tone, and circulating hormones, in addition to nerve activity. As indicated in the examples, GDNFR is found in the GI muscles and innervating neurons. Consequently, the present invention provides compositions, methods, and devices for treatment of gastrointestinal disorders including achalasia, other disorders of the lower esophageal sphincter, sphincter of Oddi dysfunction, irritable bowel syndrome, and other disorders as discussed herein.

For example, provided is a method to treat Irritable Bowel Syndrome (IBS), which is a motor disorder consisting of altered bowel habits, abdominal pain, and the absence of detectable pathology. IBS is recognized by its symptoms, which are markedly influenced by psychological factors and stressful life situations. IBS is one of the most commonly encountered gastrointestinal disorders. Between 20% and 50% of patients referred to gastrointestinal clinics suffer from IBS. Symptoms of IBS occur in approximately 14% of otherwise apparently healthy people. It is a syndrome composed of a number of conditions with similar manifestations. The major symptoms of IBS (altered bowel habits, abdominal pain and bloating) are manifestations of increased motility in the gut and hyper-secretion of gastric acid. Activity of the GI tract is modulated neurally by the central nervous system (CNS) via parasympathetic and sympathetic innervation and by the peripherally located enteric nervous system (ENS) which resides within the GI tract itself and express GDNFR.

In another aspect is provided the administration of GDNFRα to a mammal having depressed levels of endogenous GDNFRα or a defective GDNFRα gene, preferably in the situation where such depressed levels lead to a pathological disorder, or where there is lack of activation of GDNFRα and Ret. In these embodiments, where the full length GDNFRα is to be administered to the patient, it is contemplated that the gene encoding the receptor may be administered to the patient via gene therapy technology.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA*, 83:4143–4146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnolog*, 11:205–210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.*, 262:4429–4432 (1987); and Wagner et al., *Proc. Natl. Acad. Sci. USA*, 87:3410–3414 (1990). For review of the currently known gene marking and gene therapy protocols see Anderson et al., *Science*, 256:808–813 (1992).

The invention also provides antagonists of GDNFRα activation (e.g., GDNFRα antisense nucleic acid, neutralizing antibodies). Administration of GDNFRα antagonist to a mammal having increased or excessive levels of endogenous GDNFRα activation is contemplated, preferably in the situation where such increased levels of GDNFRα or Ret activation lead to a pathological disorder.

In one embodiment, GDNFRα antagonist molecules may be used to bind endogenous ligand in the body, thereby causing desensitized GDNFRα to become responsive to GDNF ligand, especially when the levels of GDNF ligand in the serum exceed normal physiological levels. Also, it may be beneficial to bind endogenous GDNF ligand which is activating undesired cellular responses (such as proliferation of GDNFR-expressing tumor cells).

Pharmaceutical compositions of soluble GDNFRα can further include a GDNF or other GDNFRα-binding agonist. Such dual compositions, e.g. containing a GDNF/GDNFRα complex, may be beneficial where it is therapeutically useful to prolong half-life of GDNF, provide a slow-release reservoir for GDNF, activate endogenous GDNFRα or Ret, and/or to supplement the lack of GDNFRα in a target Ret-expressing cell, thereby rendering the cell responsive to GDNF.

Therapeutic formulations of GDNFRα, GDNF, or agonist thereof, are prepared for storage by mixing GDNFRα, GDNF, or agonist thereof, having the desired degree of purity with optional physiologically acceptable carriers, excipients, or stabilizers (*Remington's Pharmaceutical Sciences*, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

The GDNFRα, GDNF, or agonist thereof, also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in *Remington's Pharmaceutical Sciences*, supra.

GDNFRα, GDNF, or agonist thereof, to be used for in vivo administration must be sterile. This is readily accomplished by filtration through sterile filtration membranes, prior to or following lyophilization and reconstitution. GDNFRα, GDNF, or agonist thereof, ordinarily will be stored in lyophilized form or in solution.

Therapeutic compositions of GDNFRα, GDNF, or agonist thereof, generally are placed into a container having a sterile access port, for example, an intravenous solution bag or vial having a stopper pierceable by a hypodermic injection needle.

The route of GDNFRα, GDNF, or agonist thereof, administration is in accord with known methods, e.g., those routes set forth above for specific indications, as well as the general routes of injection or infusion by intravenous, intraperitoneal, intracerebral, intramuscular, intraocular, intraarterial, or intralesional means, ,or sustained release systems as noted below. GDNFRα, GDNF, or agonist thereof, are administered continuously by infusion or by bolus injection. Generally, where the disorder permits, one should formulate and dose the GDNFRα, GDNF, or agonist thereof, for site-specific delivery. Administration can be continuous or periodic. Administration can be accomplished by a constant- or programmable-flow implantable pump or by periodic injections.

Suitable examples of sustained-release preparations include semipermeable matrices of solid hydrophobic polymers containing the protein, which matrices are in the form of shaped articles, e.g. films, or microcapsules. Examples of sustained-release matrices include polyesters, hydrogels (e.g. poly(2-hydroxyethyl-methacrylate) as described by Langer et al., *J. Biomed. Mater. Res.*, 15:167–277 (1981) and Langer, *Chem. Tech*, 12:98–105 (1982) or poly (vinylalcohol)), polylactides (U.S. Pat. No. 3,773,919, EP 58,481), copolymers of L-glutamic acid and γ ethyl-L-glutamate (Sidman et al., *Biopolymers*, 22:547–556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(–)3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release compositions of GDNFRα, GDNF, or agonist thereof, also include liposomally entrapped GDNFRα, GDNF, or agonist thereof. Liposomes containing GDNFRα, GDNF, or agonist thereof, are prepared by methods knownperse: DE 3,218,121; Epstein etal., *Proc. Natl. Acad. Sci. USA*, 82:3688–3692 (1985); Hwang et al., *Proc. Natl. Acad. Sci. USA*, 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the suitable therapy.

When applied topically, the GDNFRα, GDNF, or agonist thereof, is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the GDNFRα, GDNF, or agonist thereof, formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the GDNFRα, GDNF, or agonist thereof, held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400–600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5%, more preferably about 3%, of the gel and the GDNFRα, GDNF, or agonist thereof, is present in an amount of about 300–1000 mg per ml of gel.

Semipermeable, implantable membrane devices are useful as means for delivering drugs in certain circumstances. For example, cells that secrete soluble GDNFR, GDNF, or agonist thereof, or chimeras can be encapsulated, and such devices can be implanted into a patient, for example, into the brain of patients suffering from Parkinson's Disease. See, U.S. Pat. No. 4,892,538 of Aebischer et al.; U.S. Pat. No. 5,011,472 of Aebischer et al.; U.S. Pat. No. 5,106,627 of Aebischer et al.; PCT Application WO 91/10425; PCT Application WO 91/10470; Winn et al., *Exper. Neurolog*, 113:322–329 (1991); Aebischer et al., *Exper. Neurology*, 111:269–275 (1991); and Tresco et al., *ASAIO*, 38:17–23 (1992). Accordingly, also included is a method for preventing or treating damage to a nerve or damage to other GDNFR-expressing or GDNF-responsive cells, e.g. kidney, as taught herein, which comprises implanting cells that secrete GDNFRα, GDNF, or agonist thereof, or antagonist as may be required for the particular condition, into the body of patients in need thereof Finally, the present invention includes an implantation device, for preventing or treating nerve damage or damage to other cells as taught herein, containing a semipermeable membrane and a cell that secretes GDNFR, GDNF, or agonist thereof, (or antagonist as may be required for the particular condition) encapsulated within the membrane, the membrane being permeable to GDNFR, GDNF, or agonist thereof, and impermeable to factors from the patient detrimental to the cells. The patient's own cells, transformed to produce GDNF or GDNFR ex vivo, could be implanted directly into the patient, optionally without such encapsulation. The methodology for the membrane encapsulation of living cells is familiar to those of ordinary skill in the art, and the preparation of the encapsulated cells and their implantation in patients may be accomplished readily as is known in the art. The present invention includes, therefore, a method for preventing or treating cell damage, preferably nerve damage, by implanting cells into the body of a patient in need thereof, the cells either selected for their natural ability to generate GDNFRα, GDNF, or agonist thereof, or engineered to secrete GDNFRα, GDNF, or agonist thereof. Preferably, the secreted GDNFRα is soluble, human mature GDNFRα when the patient is human. Human mature GDNF (WO 93/06116) is the preferred form of GDNF. The implants are preferably non-immunogenic and/or prevent immunogenic implanted cells from being recognized by the immune system. For CNS delivery, a preferred location for the implant is the cerebral spinal fluid of the spinal cord.

An effective amount of GDNFRα, GDNF, or agonist thereof, to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the GDNFRα, GDNF, or agonist thereof, until a dosage is reached that achieves the desired effect. A typical daily dosage for systemic treatment might range from about 1 μg/kg to up to 10 mg/kg or more, preferably 1 μg/kg to 2 mg/kg, and more preferably 1 μg/kg to 1 mg/kg, depending on the factors mentioned above. As an alternative general proposition, the GDNFRα, GDNF, or agonist thereof, is formulated and delivered to the target site or tissue at a dosage capable of establishing in the tissue a level of GDNFRα, GDNF, or agonist thereof, greater than about 0.1 ng/cc up to a maximum dose that is efficacious but not unduly toxic. This intra-tissue concentration should be maintained if possible by continuous infusion, sustained release, topical application, GDNFRα (or GDNF or agonist thereof)-expressing cell implant, or injection at empirically determined frequencies. The progress of this therapy is easily monitored by conventional assays for the disorder to be treated. When GDNFRα is administered in complex with or concomitantly with GDNF, a 100:1 to 1:100 ratio of GDNFRα to GDNF dimer is useful. Preferably the ratio is 10:1 to 1:10, more preferably 1:1, and even more preferably 2:1, which may reflect the natural binding ratio of GDNFRα to GDNF.

GDNFRα nucleic acid is useful for the preparation of GDNFRα polypeptide by recombinant techniques exemplified herein which can then be used for production of anti-GDNFRα antibodies having various utilities described below.

The GDNFRα (polypeptide or nucleic acid) can be used to increase GDNF-responsiveness (and thus increase cell survival and modulate Ret-mediated downstream pathways) of cells in vitro. Such cells must contain or be modified to contain cell surface Ret. Cultured ex vivo, these cells may simultaneously be exposed to other known neurotrophic factors or cytokines, such as those described herein.

In yet another aspect of the invention, the GDNFRα may be used for affinity purification of ligands that bind to the GDNFRα, either naturally-occurring or synthetic ligands.

GDNF is a preferred ligand for purification. Briefly, this technique involves: (a) contacting a source of GDNF ligand with an immobilized GDNFRα under conditions whereby the GDNF ligand to be purified is selectively adsorbed onto the immobilized receptor; (b) washing the immobilized GDNFRα and its support to remove non-adsorbed material; and (c) eluting the GDNF ligand molecules from the immobilized GDNFRα to which they are adsorbed with an elution buffer. In a particularly preferred embodiment of affinity purification, GDNFRα is covalently attaching to an inert and porous matrix or resin (e.g., agarose reacted with cyanogen bromide). Especially preferred is a GDNFRα immunoadhesin immobilized on a protein A column. A solution containing GDNF ligand is then passed through the chromatographic material. The GDNF ligand adsorbs to the column and is subsequently released by changing the elution conditions (e.g. by changing pH or ionic strength). Novel ligands can be detected by monitoring displacement of a known, labeled GDNFRα ligand, such as $I^{125}$ -or biotinylated-GDNF.

The GDNFRα may be used for competitive screening of potential agonists or antagonists for binding to the GDNFRα. Such agonists or antagonists may constitute potential therapeutics for treating conditions characterized by insufficient or excessive GDNFRα activation, respectively.

The preferred technique for identifying molecules which bind to the GDNFRα utilizes a chimeric receptor (e.g., epitope-tagged GDNFRα or GDNFRα immunoadhesin) attached to a solid phase, such as the well of an assay plate. The binding of the candidate molecules, which are optionally labeled (e.g., radiolabeled), to the immobilized receptor can be measured. Alternatively, competition for binding of a known, labeled GDNFRα ligand, such as $I^{125}$-GDNF, can be measured. For screening for antagonists, the GDNFRα can be exposed to a GDNF ligand followed by the putative antagonist, or the GDNF ligand and antagonist can be added to the GDNFRα simultaneously, and the ability of the antagonist to block receptor activation can be evaluated.

The present invention also provides for assay systems for detecting GDNF activity, comprising cells which express high levels of GDNFRα, and which are, therefore, extremely sensitive to even very low concentrations of GDNF or GDNF-like molecules. The present invention provides for assay systems in which GDNF activity or activities similar to GDNF activity resulting from exposure to a peptide or non-peptide compound may be detected by measuring a physiological response to GDNF in a cell or cell line responsive to GDNF which expresses the GDNFR molecules of the invention. A physiological response may comprise any of the biological effects of GDNF, including but not limited to, those described herein, as well as the transcriptional activation of certain nucleic acid sequences (e.g. promoter/enhancer elements as well as structural genes), GDNF-related processing, translation, or phosphorylation, the induction of secondary processes in response to processes directly or indirectly induced by GDNF, including Ret-mediated effects, and morphological changes, such as neurite sprouting, or the ability to support the survival of cells, for example, nodose or dorsal root ganglion cells, motoneurons, dopaminergic neurons, sensory neurons, Purkinje cells, or hippocampal neurons.

In one embodiment of the invention, the functional interaction between GDNF and the GDNFRα may be observed by detecting an increase in the production autophosphorylated Ret protein, or alternatively, phosphorylated ERK-1 or ERK-2 homologs (See Kotzbauer et al., supra).

The present invention provides for the development of novel assay systems which can be utilized in the screening of compounds for GDNF- or GDNF-like activity. Target cells which bind GDNF may be produced by transfection with GDNFRα-encoding nucleic acid or may be identified and segregated by, for example, fluorescent-activated cell sorting, sedimentation of rosettes, or limiting dilution. Once target cell lines are produced or identified, it may be desirable to select for cells which are exceptionally sensitive to GDNF. Such target cells may bear a greater number of GDNFRα molecules; target cells bearing a relative abundance of GDNFRα can be identified by selecting target cells which bind to high levels of GDNF, for example, by marking high-expressors with fluorophore tagged-GDNF followed by immunofluorescence detection and cell sorting. Alternatively, cells which are exceptionally sensitive to GDNF may exhibit a relatively strong biological response in response to GDNF binding, such as a sharp increase in Ret-mediated effects or in immediate early gene products such as c-fos or c-jun. By developing assay systems using target cells which are extremely sensitive to GDNF, the present invention provides for methods of screening for GDNF or GDNF-like activity which are capable of detecting low levels of GDNF activity.

In particular, using recombinant DNA techniques, the present invention provides for GDNF target cells which are engineered to be highly sensitive to GDNF. For example, the GDNF-receptor gene can be inserted into cells which are naturally GDNF responsive such that the recombinant GDNFR gene is expressed at high levels and the resulting engineered target cells express a high number of GDNFRs on their cell surface. Alternatively, or additionally, the target cells may be engineered to comprise a recombinant gene which is expressed at high levels in response to GDNF/ receptor binding. Such a recombinant gene may preferably be associated with a readily detectable product. For example, and not by way of limitation, transcriptional control regions (i.e. promoter/enhancer regions) from an immediate early gene may be used to control the expression of a reporter gene in a construct which may be introduced into target cells. The immediate early gene/reporter gene construct, when expressed at high levels in target cells by virtue of a strong promoter/enhancer or high copy number, may be used to produce an amplified response to GDNFR binding. For example, and not by way of limitation, a GDNF-responsive promoter may be used to control the expression of detectable reporter genes including β-galactosidase, growth hormone, chloramphenicol acetyl transferase, neomycin phosphotransferase, luciferase, or β-glucuronidase. Detection of the products of these reporter genes, well known to one skilled in the art, may serve as a sensitive indicator for GDNF or GDNF-like activity of pharmaceutical compounds.

The GDNF- or GDNFRα-encoding gene constructs discussed herein (e.g., soluble ECD) can be inserted into target cells using any method known in the art, including but not limited to transfection, electroporation, calcium phosphate/ DEAE dextran methods, and cell gun. The constructs and engineered target cells can be used for the production of transgenic animals bearing the above-mentioned constructs as transgenes, from which GDNF- or GDNFRα-expressing target cells may be selected using the methods discussed.

Nucleic acids which encode GDNFR, preferably from non-human species, such as murine or rat protein, can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic, stage. A transgene is a DNA which is integrated into the genome of a cell from which a transgenic animal develops. In one embodiment, the human and /or rat cDNA encoding GDNFRα, or an appropriate sequence thereof, can be used to clone genomic DNA encoding GDNFR in accordance with established techniques and the genomic sequences used to generate transgenic animals that contain cells which express DNA encoding GDNFR. Methods for generating transgenic animals, particularly animals such as mice, have become conventional in the art and are described, for example, in U.S. Pat. Nos. 4,736,866 and 4,870,009. Typically, particular cells would be targeted for GDNFR transgene incorporation with tissue-specific enhancers, which could result in desired effect of treatment. Transgenic animals that include a copy of a transgene encoding GDNFR introduced into the germ line of the animal at an embryonic stage can be used to examine the effect of increased expression of DNA encoding GDNFR. Such animals can be used as tester animals for reagents thought to confer protection from, for example, diseases related to GDNF. In accordance with this facet of the invention, an animal is treated with the reagent and a reduced incidence of the disease, compared to untreated animals bearing the transgene, would indicate a potential therapeutic intervention for the disease.

Transgenic mice bearing minigenes are currently preferred. First a fusion enzyme expression construct is created and selected based on expression in cell culture as described in the Examples. Then a minigene capable of expressing that fusion enzyme is constructed using known techniques. Particularly preferred hosts are those bearing minigene constructs comprising a transcriptional regulatory element that is tissue-specific therein.

Transgenic mice expressing GDNFR minigene are made using known techniques, involving, for example, retrieval of fertilized ova, microinjection of the DNA construct into male pronuclei, and re-insertion of the fertilized transgenic ova into the uteri of hormonally manipulated pseudopregnant foster mothers. Alternatively, chimeras are made using known techniques employing, for example, embryonic stem cells (Rossant et al., *Philos. Trans. R. Soc. Lond Biol.* 339:207–215 (1993)) or primordial germ cells (Vick et al. *Philos. Trans. R. Soc. Lond. Biol.* 251:179–182(1993)) of the host species. Insertion of the transgene can be evaluated by Southern blotting of DNA prepared from the tails of offspring mice. Such transgenic mice are then back-crossed to yield homozygotes.

It is now well-established that transgenes are expressed more efficiently if they contain introns at the 5' end, and if these are the naturally occurring introns (Brinster et al. *Proc. Natl. Acad. Sci. USA* 85:836 (1988); Yokode et al., *Science* 250:1273 (1990)).

Transgenic mice expressing GDNFR minigene are created using established procedures for creating transgenic mice. Transgenic mice are constructed using now standard methods (et al. *Proc. Natl. Acad. Sci. USA* 85:836 (1988); Yokode et al., *Science* 250:1273 (1990); Rubin et al., *Proc Natl Acad Sci USA* 88:434 (1991); Rubin et al. *Nature* 353:265 (1991)). Fertilized eggs from timed matings are harvested from the oviduct by gentle rinsing with PBS and are microinjected with up to 100 nanoliters of a DNA solution, delivering about $10^4$ DNA molecules into the male pronucleus. Successfully injected eggs are then re-implanted into pseudopregnant foster mothers by oviduct transfer. Less than 5% of microinjected eggs yield transgenic offspring and only about ⅓ of these actively express the transgene: this number is presumably influenced by the site at which the transgene enters the genome.

Transgenic offspring are identified by demonstrating incorporation of the microinjected transgene into their genomes, preferably by preparing DNA from short sections of tail and analyzing by Southern blotting for presence of the transgene ("Tail Blots"). A preferred probe is a segment of a minigene fusion construct that is uniquely present in the transgene and not in the mouse genome. Alternatively, substitution of a natural sequence of codons in the transgene with a different sequence that still encodes the same peptide yields a unique region identifiable in DNA and RNA analysis. Transgenic "founder" mice identified in this fashion are bred with normal mice to yield heterozygotes, which are back-crossed to create a line of transgenic mice. Tail blots of each mouse from each generation are examined until the strain is established and homozygous. Each successfully created founder mouse and its strain vary from other strains in the location and copy number of transgenes inserted into the mouse genome, and hence have widely varying levels of transgene expression. Selected animals from each established line are sacrificed at 2 months of age and the expression of the transgene is analyzed by Northern blotting of RNA from liver, muscle, fat, kidney, brain, lung, heart, spleen, gonad, adrenal and intestine.

Alternatively, the non-human homologs of GDNFR can be used to construct a GDNFR "knock out" animal, i.e., having a defective or altered gene encoding GDNFR, as a result of homologous recombination between the endogenous GDNFR gene and an altered genomic GDNFR DNA introduced into an embryonic cell of the animal. For example, murine GDNFR cDNA can be used to clone genomic GDNFR DNA in accordance with established techniques. A portion of the genomic GDNFR DNA (e.g., such as an exon which encodes e.g., an extracellular domain) can be deleted or replaced with another gene, such as a gene encoding a selectable marker which can be used to monitor integration. Typically, several kilobases of unaltered flanking DNA (both at the 5' and 3'ends) are included in the vector (see e.g., Thomas and Capecchi, *Cell* 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., *Cell* 69:915 (1992)). The selected cells are then injected into a blastocyst of an animal (e.g., a mouse) to form aggregation chimeras (see e.g., Bradley, in Teratocarcinomas and Embryonic Stem Cells: A Practical Approach, E. J. Robertson, ed. (IRL, Oxford, 1987), pp.113–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for their ability to accept grafts, reject tumors and defend against infectious diseases and can be used in the study of basic immunobiology.

In addition to the above procedures, which can be used for preparing recombinant DNA molecules and tansformed host animals in accordance with the practices of this invention, other known techniques and modifications thereof can be used in carrying out the practice of the invention. For example, U.S. Pat. No. 4,736,866 discloses vectors and methods for production of a transgenic non-human eukaryotic animal whose germ cells and somatic cells contain a gene sequence introduced into the animal, or an ancestor of the animal, at an embryonic stage. U.S. Pat. No. 5,087,571 discloses a method of providing a cell culture comprising (1) providing a transgenic non-human mammal, all of whose germ cells and somatic cells contain a recombinant gene sequence introduced at an embryonic stage; and (2) culturing one or more of said somatic cells. U.S. Pat. No. 5,175,385 discloses vectors and methods for production of a transgenic mouse whose somatic and germ cells contain and express a gene at sufficient levels to provide the desired phenotype in the mouse, the gene having been introduced into said mouse or an ancestor of said mouse at an embryonic stage, preferably by microinjection. A partially constitutive promoter, the metallothionein promoter, was used to drive heterologous gene expression. U.S. Pat. No. 5,175,384 discloses a method of introducing a transgene into an embryo by infecting the embryo with a retrovirus containing the transgene. U.S. Pat. No. 5,175,383 discloses DNA constructs having a gene, homologous to the host cell, operably linked to a heterologous and inducible promoter effective for the expression of the gene in the urogenital tissues of a mouse, the transgene being introduced into the mouse at an embryonic stage to produce a transgenic mouse. Even though a homologous gene is introduced, the gene can integrate into a chromosome of the mouse at a site different from the location of the endogenous coding sequence. The vital MMTV promoter was disclosed as a suitable inducible promoter. U.S. Pat. No. 5,162,215, discloses methods and vectors for transfer of genes in avian species, including livestock species such as chickens, turkeys, quails or ducks, utilizing pluripotent stem cells of embryos to produce transgenic animals. U.S. Pat. No. 5,082,779, discloses pituitary-specific expression promoters for use in producing transgenic animals capable of tissue-specific expression of a gene. U.S. Pat. No. 5,075,229, discloses vectors and methods to produce transgenic, chimeric animals whose hemopoietic liver cells contain and express a functional gene driven by a liver-specific promoter, by injecting into the peritoneal cavity of a host fetus the disclosed vectors such that the vector integrates into the genome of fetal hemopoietic liver cells.

Although some of the above-mentioned patents and publications are directed to the production or use of a particular gene product or material that are not within the scope of the present invention, the procedures described therein can easily be modified to the practice of the invention described in this specification by those skilled in the art of fermentation and genetic engineering.

Assay systems of the present invention enable the efficient screening of pharmaceutical compounds for use in the treatment of GDNF-associated diseases. For example, and not by way of limitation, it may be desirable to screen a pharmaceutical agent for GDNF activity and therapeutic efficacy in renal or cerebellar degeneration. In a one embodiment of the invention, cells responsive to GDNF may be identified and isolated, and then cultured in microwells in a multiwell culture plate. Culture medium with added test agent, or added GDNF, in numerous dilutions may be added to the wells, together with suitable controls. The cells may then be examined for improved survival, neurite sprouting, and the like, and the activity of test agent and GDNF, as well as their relative activities, can be determined. For example, one can now identify GDNF-like compounds which can, like GDNF, prevent motoneuron cell death in response to toxic assault or axotomy, for example. GDNF-responsive motoneurons or enteric neurons could be utilized in assay systems to identify compounds useful in treating motoneuron or enteric nervous system diseases. If a particular disease is found to be associated with a defective GDNF response in a particular tissue, a rational treatment for the disease would be supplying the patient with exogenous GDNF. However, it may be desirable to develop molecules which have a longer half-life than endogenous GDNF, or which act as GDNF agonists, or which are targeted to a particular tissue. Accordingly, the methods of the invention can be used to produce efficient and sensitive screening systems which can be used to identify molecules with the desired properties. Similar assay systems could be used to identify GDNF antagonists.

In addition, the present invention provides for experimental model systems for studying the physiological role of GDNF and its receptor. Such systems include animal models, such as (i) animals exposed to circulating GDNFRα peptides which compete with cellular receptor for GDNF binding and thereby produce a GDNF-depleted condition, (ii) animals immunized with GDNFR; (iii) transgenic animals which express high levels of GDNFR and therefore are hypersensitive to GDNF; and (iv) animals derived using embryonic stem cell technology in which the endogenous GDNFR genes were deleted from the genome.

The present invention also provides for experimental model systems for studying the physiological role of GDNF and its receptor. In these model systems GDNFR protein, peptide fragment, or a derivative thereof, may be either supplied to the system or produced within the system. Such model systems could be used to study the effects of GDNF excess or GDNF depletion. The experimental model systems may be used to study the effects of increased or decreased response to GDNF in cell or tissue cultures, in whole animals, in particular cells or tissues within whole animals or tissue culture systems, or over specified time intervals (including during embryogenesis) in embodiments in which GDNFR expression is controlled by an inducible or developmentally regulated promoter. In a particular embodiment of the invention, the CMV promoter may be used to control expression of GDNFRα in transgenic animals. Transgenic animals, as discussed herein, are produced by any method known in the art, including, but not limited to microinjection, cell fusion, transfection, and electroporation.

The present invention also provides for model systems for autoimmune disease in which an autoimmune response is directed toward GDNFRα. Such models comprise animals which have been immunized with immunogenic amounts of GDNFR and preferably found to produce anti-GDNFR antibodies and/or cell-mediated immunity. To produce such a model system, it may be desirable to administer the GDNFR in conjunction with an immune adjuvant.

For-example, and not by way of limitation, an experimental model system may be created which may be used to study the effects of excess GDNF activity. In such a system, the response to GDNF may be increased by engineering an increased number of GDNFRs on cells of the model system relative to cells which have not been so engineered. These cells should also express Ret or another signalling molecule capable of interacting with GDNFRα and mediating an GDNF signal. It may be preferable to provide an increased number of GDNFRs selectively on cells which normally express GDNFRs. Cells may be engineered to produce increased numbers of GDNFR by infection with a virus which carries a GDNFR gene of the invention. Alternatively, the GDNFR gene may be provided to the cells by transfection. If the model system is an animal, a recombinant GDNFR gene may be introduced into the cells of the animal by infection with a virus which carries the GDNFR gene or other means as discussed herein. For example, a transgenic animal may be created which carries the GDNFR gene as a transgene. In order to ensure expression of GDNFR, the GDNFR gene should be placed under the control of a suitable promoter sequence. It may be desirable to put the GDNFR gene under the control of a constitutive and/or tissue specific promoter. By increasing the number of cellular GDNFRs, the response to endogenous GDNF may be increased. If the model system contains little or no GDNF, GDNF may be added to the system. It may also be desirable to add additional GDNF to the model system in order to evaluate the effects of excess GDNF activity. Over expressing GDNF (or secreted GDNF) may be the preferable method for studying the effects of elevated levels of GDNF on cells already expressing GDNFR. More preferably would be to express GDNFR in all cells (general expression) and determine which cells are then endowed with functional responsiveness to GDNF, thus allowing the potential identification of a second receptor component, if one exists.

An experimental model system may be created which may be used to study the effects of diminished GDNF activity. This system may permit identification of processes or neurons which require GDNF, and which may represent potential therapeutic targets. In such a system, the response to GDNF may be decreased by providing recombinant GDNFRs which are not associated with a cell surface or which are engineered so as to be ineffective in transducing a response to GDNF. For example, GDNFR protein, peptide, or derivative may be supplied to the system such that the supplied receptor may compete with endogenous GDNFR for GDNF binding, thereby diminishing the response to GDNF. The GDNFR may be a cell free receptor which is either added to the system or produced by the system. For example, a GDNFR protein which lacks the transmembrane domain may be produced by cells within the system, such as an anchorless GDNFR that may be secreted from the producing cell. Alternatively, GDNFR protein, peptide or derivative may be added to an extracellular space within the system. In additional embodiments of the invention, a recombinant GDNFR gene may be used to inactivate or "knock out" the endogenous gene by homologous recombination, and thus create a GDNFR deficient cell, tissue, or animal. For example, and not by way of limitation, a recombinant GDNFR gene may be engineered to contain an insertional mutation, for example the neo gene, which inactivates GDNFR. Such a construct, under the control of a suitable promoter, may be introduced into a cell, such as an embryonic stem cell, by a technique such as transfection, transduction, injection, etc. Cells containing the construct may then be selected by G418 resistance. Cells which lack an intact GDNFR gene may then be identified, e.g. by Southern blotting or Northern blotting or assay of expression. Cells lacking an intact GDNFR gene may then be fused to early embryo cells to generate transgenic animals deficient in GDNFR. A comparison of such an animal with an animal not expressing endogenous GDNF would reveal that either the two phenotypes match completely or that they do not, implying the presence of additional GDNF-like factors or receptors. Such an animal may be used to define specific cell populations, e.g., neuronal populations, or any other in vivo processes, normally dependent upon GDNF or its receptor. Thus, these populations or processes may be expected to be effected if the animal did not express GDNFR and therefore could not respond to GDNF. Alternatively, a recombinant GDNFR protein, peptide, or derivative which competes with endogenous receptor for GDNF may be expressed on the surface of cells within the system, but may be engineered so as to fail to transduce a response to GDNF binding. The recombinant GDNFR proteins, peptides or derivatives described above may bind to GDNF with an affinity that is similar to or different from the affinity of endogenous GDNFR to GDNF. To more effectively diminish the response to GDNF, the GDNFR protein, peptide, or derivative may desirably bind to GDNF with a greater affinity than that exhibited by the native receptor. If the GDNFR protein, peptide, or derivative is produced within the model system, nucleic acid encoding the GDNFR protein, peptide, or derivative may be supplied to the system by infection, transduction, transfection, etc. or as a transgene. As discussed supra, the GDNFR gene may be placed under the control of a suitable promoter, which may be, for example, a tissue-specific promoter or an inducible promoter or developmentally regulated promoter. In a specific embodiment of the invention the endogenous GDNFR gene of a cell may be replaced by a mutant GDNFR gene by homologous recombination. In a further embodiment of the invention, GDNFR expression may be reduced by providing GDNFR expressing cells with an amount of GDNFR antisense RNA or DNA effective to reduce expression of GDNFR protein.

The GDNFRα polypeptides are also useful as molecular weight markers. To use a GDNFRα polypeptide as a molecular weight marker, gel filtration chromatography or SDS-PAGE, for example, will be used to separate protein(s) for which it is desired to determine their molecular weight(s) in substantially the normal way. GDNFRα, preferably a soluble GDNFR, and other molecular weight markers will be used as standards to provide a range of molecular weights. For example, phosphorylase b (mw=97,400), bovine serum albumin (mw=68,000), ovalbumin (mw=46,000), trypsin inhibitor (mw=20,100), and lysozyme (mw=14,400) can be used as MW markers. The other molecular weight markers mentioned here can be purchased commercially from Amersham Corporation, Arlington Heights, Ill. The molecular weight markers are generally labeled to facilitate detection thereof. For example, the markers may be biotinylated and, following separation, can be incubated with streptavidin-horseradish peroxidase so that the various markers can be detected by light detection. The polypeptides of the invention also find use as feed additives for animals. The nucleic acids of the invention find use in preparing these polypeptides.

The purified GDNFRα, and the nucleic acid encoding it, may also be sold as reagents for mechanism studies of GDNFRα and its ligands, to study the role of the GDNFRα and GDNF ligand in normal growth and development, as well as abnormal growth and development, e.g, in malignancies. GDNFR probes can be used to identify cells and tissues which are responsive to GDNF in normal or diseased states. For example, a patient suffering from a GDNF-related disorder may exhibit an aberrancy of GDNFR expression. The present invention provides for methods for identifying cells which are responsive to GDNF by detecting GDNFR expression in such cells. GDNFR expression may be evidenced by transcription of GDNFR mRNA or production of GDNFR protein. GDNFR expression may be detected using probes which identify GDNFR nucleic acid or protein. One variety of probe which maybe used to detect GDNFR expression is a nucleic acid probe, which may be used to detect GDNFR-encoding RNA by any method known in the art, including, but not limited to, in situ hybridization, Northern blot analysis, or PCR related techniques. Another variety of probe which may be used is tagged GDNF as discussed herein.

According to the invention, tagged GDNF may be incubated with cells under conditions which would promote the binding or attachment of GDNF to GDNFR in or on said cells. In most cases, this may be achieved under standard culture conditions. For example, in one embodiment of the invention, cells may be incubated for about 30 minutes in the presence of tagged GDNF. If the tag is an antibody molecule, it may be preferable to allow GDNF to bind to cells first and subsequently wash the cells to remove unbound ligand, followed by adding anti-GDNF antibody tag. In another embodiment of the invention, tagged GDNF on the surface of GDNF-responsive cells, hereafter called target cells, may be detected by rosetting assays in which indicator cells that are capable of binding to the tag are incubated with cells bearing tagged-GDNF such that they adhere to tagged-GDNF on the target cells and the bound indicator cells form rosette-like clusters around GDNF-tag bearing cells. These rosettes may be visualized by standard microscopic techniques on plated cells, or, alternatively, may allow separation of rosetted and non-rosetted cells by density centrifugation. In a preferred specific embodiment of the invention, target cells, such as neuronal cells. In alternative embodiments of the invention, tagged-GDNF on the surface of target cells may be detected using immunofluorescent techniques in which a molecule which reacts with the tag, preferably an antibody, directly or indirectly produces fluorescent light. The fluorescence may either be observed under a microscope or used to segregate tagged-GDNF-bearing cells by fluorescence activated cell sorting techniques. The present invention also provides for methods for detecting other forms of tags, such as chromogenic tags and catalytic tags. An anti-GDNFR antibody can also be used as a probe. The detection methods for any particular tag will depend on the conditions necessary for producing a signal from the tag, but should be readily discernible by one skilled in the art.

GDNFRα variants are useful as standards or controls in assays for the GDNFRα for example ELISA, RIA, or RRA, provided that they are recognized by the analytical system employed, e.g., an anti-GDNFRα antibody.

Polyclonal antibodies are generally raised in animals by multiple subcutaneous (sc) or intraperitoneal (ip) injections of the relevant antigen and an adjuvant. Since the preferred epitope is in the ECD of the GDNFRα, it is desirable to use GDNFRα ECD or a molecule comprising the ECD (e.g. GDNFRα immunoadhesin) as the antigen for generation of polyclonal and monoclonal antibodies. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining 1 mg or 1 µg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fushing agent, such as polyethylene glycol, to form a hybridoma cell (Goding, Monoclonal Antibodies: Principles and Practice, pp.59–103 (Academic Press, 1986)).

The hybridoma cells thus prepared are seeded and grown in a suitable culture medium that preferably contains one or more substances that inhibit the growth or survival of the unfused, parental myelomacells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The ability of the MAbs to block binding of GDNF to its receptor can be evaluated by ELISA and bioassay utilizing available reagents (rhGDNFr-IgG; a stable transfected CHO cell line expressing GDNFRα) Neutralizing activities can also be evaluated by neuronal survival assay(s).

GDNFR-specific MAbs can be developed as discussed above using for example, the receptor immunoadhesin and transfected cell line) to initiate new immunization protocols to generate GDNFR-specific MAbs for use as potential agonists or antagonists, as well as for immunohistochemistry, immunocytochemistry, and assay development. The MAbs generated from fusion of the immunized animals can be screened for agonist and antagonist activities by bioassay (e.g., neuron survival assays, signal transduction/phosphorylation, kidney cell survival assays) as well as by ELISA and FACS (functional blocking of GDNF-GDNFR binding). Suitable techniques are provided in, for example, Lucas et al., *J. Immunol.* 145:1415–1422 (1990); Hoogenraad et al. J. Immunol. Methods 6:317–320 (1983); Moks et al., Eur. J. Biochem. 85:1205–1210 (1986); Laemmli, Nature (London) 227:680–685 (1970); and, Towbin et al., Proc Natl Acad Sci USA 76:4350–4354 (1979).

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol*, 5:256–262 (1993) and Plüackthun, *Immunol Revs.*, 130:151–188 (1992).

In a further embodiment, antibodies or antibody fragments can be isolated from antibody phage libraries generated using the techniques described in McCafferty et al., *Nature*, 348:552–554 (1990). Clackson et al., *Nature*, 352:624–628(1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Mark et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (Cabilly et al., supra, Morrison, et al., *Proc. Nat.* *Acad Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (eg., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci USA*, 90:2551 (1993); Jakobovits et al., *Nature*, 362:255–258 (1993); Bruggermann et al., *Year in Immuno.*, 7:33 (1993). Human antibodies can also be produced in phage-display libraries (Hoogenboom et al., *J. Mol. Biol.*, 227:381 (1991); Marks et al., *J. Mol. Biol*, 222:581 (1991)).

Bispecific antibodies (BsAbs) are antibodies that have binding specificities for at least two different antigens. BsAbs can be used as tumor targeting or imaging agents and can be used to target enzymes or toxins to a cell possessing the GDNFRα. Such antibodies can be derived from full length antibodies or antibody fragments (e.g F(ab')$_2$ bispecific antibodies). In accordance with the present invention, the BsAb may possess one arm which binds the GDNFRα and another arm which binds to a cytokine or another cytokine receptor (or a subunit thereof) such as the receptors for TPO, EPO, G-CSF, IL-4, IL-7, GH, PRL; the α or β subunits of the IL-3, GM-CSF, IL-5, IL-6, LIF, OSM and CNTF receptors; or the α, β or γ subunits of the IL-2 receptor complex. For example, the BsAb may bind both GDNFRα and gp130.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., *EMBO J.*, 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology*, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. According to these techniques, Fab'-SH fragments can be recovered from *E. coli*, which can be chemically coupled to form bivalent antibodies. Shalaby et al., *J. Exp. Med.*, 175:217–225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodrigues et al., *Int. J. Cancers*, (Suppl.) 7:45–50 (1992).

Various techniques for making and isolating bivalent antibody fragments directly from recombinant cell culture have also been described. For example, bivalent heterodimers have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA*, 90:6444–6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported. See Gruber et al., *J. Immunol.*, 152:5368 (1994).

The GDNFRα agonists (including GDNF and GDNF/soluble GDNFRα complex) and agonist GDNFRα antibodies of the present invention can be used to enhance splenic hematopoiesis, allowing some repopulation of blood cell lineages in patients having undergone chemo- or radiation therapy and transplantation. Generally, the agonists or antibodies will act to enhance proliferation and/or differentiation (but especially proliferation) of hematopoietic cells in the spleen. Without being bound by theory, GDNFR agonists may act directly as a growth, survival or differentiation factor for hematopoietic cells in the spleen and/or may indirectly act on the splenic stromal environment (possibly neurons involved in the splenic innervation) to produce another factor that is responsible for the maintenance of hematopoietic lineages. In any event, as taught herein GDNFR agonist, including GDNF, have therapeutic benefit in facilitating the splenic engraftment of bone marrow transplants following irradiation or chemotherapy or for stimulating extramedullary hematopoiesis in the spleen (which is normal in rodents, but not normally seen in man) in those conditions where there is an increased demand for blood cell production due to anemia (red blood cells), chronic infection (neutrophils), bone marrow failure (all lineages), and immune deficiency (lymphocytes). The agonists may similarly be useful for treating diseases characterized by a decrease in blood cells. Examples of these diseases include: anemia (including macrocytic and aplastic anemia); thrombocytopenia; hypoplasia; immune (autoimmune) thrombocytopenic purpura (ITP); and HIV induced ITP. Also, the agonists may be used to treat a patient having suffered a hemorrhage.

Therapeutic applications for GDNF or GDNFRα neutralizing antibodies include the treatment of metabolic disorders and cell tumors at sites of GDNFRα expression, especially those tumors characterized by overexpression of GDNFRα.

For therapeutic applications, the GDNF or GDNFRα antibodies of the invention are administered to a mammal, preferably a human, in a physiologically acceptable dosage form, including those that may be administered to a human intravenously as a bolus or by continuous infusion over a period of time, by intramuscular, intraperitoneal, intracerebrospinal, subcutaneous, intra-articular, intrasynovial, intrathecal, oral, topical, or inhalation routes. The antibodies also are suitably administered by intratumoral, peritumoral, intralesional, or perilesional routes or to the lymph, to exert local as well as systemic therapeutic effects.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of GDNF or GDNFRα antibodies include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The antibody will typically be formulated in such vehicles at a concentration of about 0.1 mg/ml to 100 mg/ml.

Suitable examples of sustained-release preparations include semipermeable matrices of solid hydrophobic polymers containing the GDNF or GDNFRα antibody, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and γ ethyl-L-glutamate (Sidman et al., supra), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated, antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release GDNF or GDNFRα antibody compositions also include liposomally entrapped antibodies. Liposomes containing the antibodies are prepared by methods known in the art, such as described in Epstein et al., *Proc. Natl. Acad. Sci. USA*, 82:3688(1985); Hwang et al., *Proc. Natl. Acad. Sci. USA*, 77:4030 (1980); and U.S. Pat. Nos. 4,485,045 and 4,544,545. Ordinarily, the liposomes are the small (about 200–800 Angstroms) unilamellar type in which the lipid content is greater than about 30 mol. % cholesterol, the selected proportion being adjusted for the optimal antibody therapy. Liposomes with enhanced circulation time are disclosed in U.S. Pat. No. 5,013,556.

For the prevention or treatment of disease, the appropriate dosage of GDNF or GDNFRα antibody will depend on the type of disease to be treated, as defined above, the severity and course of the disease, whether the antibodies are administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 15 mg/kg of GDNF- or GDNFRα antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

Animal model are available to assess effects of the compounds and method of the invention. For example, to assess the effects of treating damaged kidneys with compositions that affect growth (Toback, 1977; Toback et al. 1977), an intravenous injection of 1.0 to 1.1 mg of mercury per kg of body weight as HgCl2 is given to rats to induce a reversible syndrome of acute nonoliguric acute renal failure. After one day, there are marked increases in serum urea nitrogen concentration (SUN), urinary excretion of sodium and protein, and necrosis of proximal tubular cells. By day two, increases in phospholipid, DNA and RNA synthesis, and mitotic index indicate that cellular regeneration is underway. By day three, the SUN reaches a maximum, and squamoid epithelial cells appear on the tubular basement membrane. At day five, the SUN returns to normal, the maximal rate of phospholipid synthesis is reached, and the tubules are repopulated with more mature cells. The effects of infusion of a composition of autocrine growth factors on renal structure is compared with untreated rats and animals infused with vehicle alone during the course of the mercuric chloride-induced acute tubular necrosis syndrome discussed above.

The antibodies of the invention are also useful as affinity purification agents. In this process, the antibodies against GDNFRα are immobilized on a suitable support, such a Sephadex resin or filter paper, using methods well known in the art. The immobilized antibody then is contacted with a sample containing the GDNFRα to be purified, and thereafter the support is washed with a suitable solvent that will remove substantially all the material in the sample except the GDNFRα, which is bound to the immobilized antibody. Finally, the support is washed with another suitable solvent, such as glycine buffer, pH 5.0, that will release the GDNFRα from the antibody.

GDNFRα antibodies may also be useful in diagnostic assays for GDNFRα, e.g., detecting its expression in specific cells, tissues, or serum. For diagnostic applications, antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the polypeptide variant to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147–158 (CRC Press, Inc., 1987).

Competitive binding assays rely on the ability of a labeled standard to compete with the test sample analyte for binding with a limited amount of antibody. For example, the amount of GDNFRα in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme the following Examples of specific embodiments for carrying out the present invention are offered for illustrative purposes only, and are not intended to limit the scope of the present invention in any way.

The disclosures of all publications, patents and patent applications cited herein are hereby incorporated by reference in their entirety.

EXAMPLES

Example 1

Cloning of GDNFRα

Ventral midbrain tissue of E14 rat embryos, containing GDNF responsive dopaminergic neurons, was used to generate a cDNA library in a cytomegalovirus based expression vector (Holmes et al., *Science*, 253:1278–1280 (1991)). Pools of 1500 cDNAs clones were transfected into COS 7 cells and expression of putative GDNF receptor proteins was detected by binding of iodinated GDNF to the cells followed by autoradiography or by staining of bound cold GDNF with GDNF antibodies (Gearing et al., *EMBO J.*, 8:3667–3676 (1989)). Three hundred and thirty cDNA pools were screened. A single positive pool was identified. This pool was repeatedly subdivided into smaller pools and each pool was screened until a single cDNA clone has been isolated.

The cDNA (nucleic acid sequence shown in FIGS. 1A–1E) was found to encode a novel, cysteine-rich protein of 468 amino acid (designated full-length "GDNFRα"), which contains a signal peptide at its amino terminus and a stretch of 23 hydrophobic amino acid at its carboxy terminus (see FIG. 2). Three potential glycosylation sites are indicated (FIG. 2). The carboxy-terminal hydrophobic sequence is preceded by a group of small amino acids (Ala Ser Ser), defining a cleavage/attachment site for GPI linked protein (Micanovic et al., *Proc. Natl. Acad. Sci. USA*, 87:157–161 (1990); Moran et al., *J. Biol. Chem.*, 266:1250–1257 (1991)). The 30 cysteines are arranged in a manner that resembles the cysteine spacing in the cytokine receptor family (Bazan, *Proc. Natl. Acad. Sci. USA*, 87:6934–6938 (1990)). The extracellular domain ("ECD") is flanked by the signal peptide and the GPI-attachment site.

In addition to the cDNA isolated by expression cloning, nine other cDNAs were isolated from rat (4) and mouse (5) cDNA libraries using GDNFRα cDNA as a probe; of these 8 contained an open reading frame identical to GDNFRα, whereas one rat cDNA encoded a shorter open reading frame of 158 amino acids, which may represent an aberrant or a secreted form of this protein.

One independent cDNA clone, designated clone 26, which includes a full-length GDNFRα orf, was isolated from a mouse cDNA library using rat GDNFRα cDNA as a probe. The sequence of the 5' end of the mouse GDNFRα clone(s) is provided with the translation methionine start codon underlined:

CCGGCACTGAATCTAGGAAGGAGCCCAGGATGAGCGGCAGGTTGGGTCGGAACTGAACCCCTAAAAGCGGGTCCGCCTCCCGCCCTCGCGCCCGCTCGGAGCTGAGTCCCTGGCGGCGGTGGGCGGCAGAGCAACGGGGAGTCTGCTCTCACCCTGGATGGAGCTTAACTTTGAGTGGCCAGAGGAGCGCAGTCGCCCGGGGATCTCTGCACGCTGAGCTCTCTCCGCGAGATCCGGTGGCGGCTTTGGATTTTGGGGGGGCGGGGACCAGCTGCGCGGTGGCACCATGTTCCTAGCCACTCTGTACTTCGTGCTGCCACTCCTGGATTTGCTGATGTCGGCCGAGGTGAGTGGTGGGGACCGCCTGGACTGTGTGAAAGCCAGTGATCAGTGCCTGAAGGAACAGAGCTGCAGCACC(SEQ ID NO:8)

And the sequence encoding the C-terminal end of the mouse GDNFRα sequence is provided with the C-terminal serine codon underlined:

CGCCGCAAGTGCCACAAAGCCCTCAG-GCAGTTCTTCGACAAAGTTCCAGCCAAG-CACAGCTACGGGATGCTCTTCTGCTCCT-GCCGGGACGTCGCCTGCACCGAGAGGCGGCGACAGACTATCGTCCCTGTGTGCTCCTAT-GAAGAACGAGAGAGGCCCAACTGCCT-GAATCTGCAAGACTCCTGCAAGACAAAT-TACATCTGCAGATCTCGCCTTGCAGATTTTTTACCAACTGCCAGCCAGAGTCAAGGTCTGT-CAGCAACTGTCTTAAGGAGAACTACGCA-GACTGCCTCCTGGCCTACTCGGGACT-GATTGGCACAGTCATGACTCCTAACTACATAGACTCCAGCAGCCTCAGTGTGGCGCCGTG-GTGCGATTGCAGCAACAGTGGCAATGAC-CTGGAAGATTGCCTGAAGTTTCT-GAATTTTTTTAAGGACAATACGTGTCTCAAAAATGCAATTCAAGCCTTTGGCAATGGCTCG-GATGTGACCATGTGGCAGCCAGC-CCCCCCAGTCCAGACCACCACTGCCAC-GACTACCACTGCCTTCCGGATCAAGAACAAGCCTCTAGGGCCAGCAGGCTCTGAGAAT-GAGATTCCACACACGTTTTACCACCGT-GTGCTAATTTGCAGGCACAGAAGCT-GAAATCCAATGTATCGGGCAGTACACATCTCTGTCTTTCTGATAATGATTACGGAAAG-GATGGTCTCGCTGGTGCCTCCAGCCA-CATAACCACAAAATCAATGGCTGCTC-CTCCCAGCTGCGGTCTGAGCTCACTGCCGGTGATGGTGTTCACCGCTCTGGCTGCCCTGTTGTCTGTATCATTGGCAGAAACATCG(SEQ ID NO:9).

The sequences are highly homologous to those in FIGS. 1A–1E at both the amino and nucleic acid levels.

Other sequences that find use in the invention, particularly as probes to identify additional GDNFR sequences, including human variants, include or comprise the human EST-derived sequence designated ye83h05.r1or fragments thereof:

5'-AGGGAATTTGGCCCTCGAGGAAGGAGATTCGGCACGAGGCCAAGAGCAACCATTGCCTGGATGCTGCCAAGGCCTGCAACCTGAATGACAACTGCAAGAAGCTGCGCTCCTCCTACATCTCCATCTGCAACCGCGAGATCTCGCCCACCGAGCGCTGCAACCGCCGCAAGTGCCACAAGGCCCTGCGCCAGTTCTTCGACCGGGTGCCCAGCGAGTACACCTACCGCATGCTCTTCTGCTCCTGCCAAGATCAGGCGTGCGCTGAGCNCGCGGNCAAAACCATCCTGCCCAGCTGCTCCTATGAGGACAAGGAGAAGCCCAACTGCNTGGACNTGCGTGGCGTGTGCCGG(SEQ ID NO:10).

A-3'; and the human EST-derived sequence designated yI70a10.r1 or fragments thereof:

5'-GCAACCATTGCCTGGATGCTGCCAAGGCCTGCAACCTGAATGACAACTGCAAGAAGCTGCGCTCCTCCTACATCTCCATCTGCAACCGCGAGATCTCGCCCACCGAGCGCTGCAACCGCCGCAAGTGCCACAAGGCCCTGCGCCAGTTCTTCGACCGGGTGCCAGCGAGTACACCTACCGCATGCTCTTCTGCTCCTGCCAAGACCAGGCGTGCGCTGAGCGCGCGGGCAAAACCATCCTGCCCAGCTGCTCCTATGAGGACAAGGAGAAGCCCAACTGCCTGGACCTGCGTGGCGTGTGCCGGACTGACCACCTGTGTCGGTCCGGCTNGCCGACTTTCCATGCCAATTTGTTCGAGCCTTCCTACCAGACGGGTCACCAGGCTGCCCTNGCGGACAATTTACCAGGGCGTGTCTTGGGGTCTTNATGTTGGCATGATTGGGTTTGACAT-3' (SEQ ID NO:11).

Also of interest are sequence fragments derived from the above two sequences, and nucleic acids comprising these fragments or proteins comprising the amino acid sequence encoded by these fragments, for example: GCAA CCATTGCCTGGATGCTGCCAAGGCCTGCAACCTG AATGACAACTGCAAGAAGCTGCGCTCCTCCTACA TCTCCATCTGCAACCGCGAGATCTCGCCCACCGA GCGCTGCAACCGCCGCAAGTGCCACAAGGCCCT GCGCCAGTTCTTCGACCGGGTGCCCAGCGAGTAC ACCTACCGCATGCTCTTCTGCTCCTGCC, and GCAACCATTGCCTGGATGCTGCCAAGGCCTGCAA CCTGAATGACAACTGCAAGAAGCTGCGCTCCTC CTACATCTCCATCTGCAACCGCGAGATCTCGCCCA CCGAGCGCTGCAACCGCCGCAAGTGCCACAAGG CCCTGCGCCAGTTCTTCGACCGGGTGCCCAGCGA GTACACCTACCGCATGCTCTTCTGCTCCTGCC(SEQ ID NO:12).

Example 2

GDNFRα Binds GDNF

To characterize the interaction between GDNF and GDNFRα, cross-linking and competition binding experiments were performed using Chinese hamster ovary cells stably expressing GDNFRα. For cross-linking, Chinese hamster ovary (CHO) cells stably expressing GDNFRα or an irrelevant protein were incubated for 1 h at 37° C. either in the presence or absence of PIPLC (2 μg/ml) and were then resuspended at a density of 1–2×10$^6$/ml in ice-cold L15 media with 1 mM phenylmethylsulfonyl fluoride and 50 pM $^{125}$I-labeled GDNF and incubated at 4° C. for 2 hr. Formaldehyde was added to a final concentration of 4% at room temperature for 30 min. The cells were washed 3 times with 1 ml of phosphate-buffered saline. Cells were then lysed in sample buffer (80 mM Tris-HCl [pH 6.8], 10% [v/v] glycerol, 1% [w/v] SDS, 0.025% Bromphenol Blue and loaded on to SDS-polyacrylamide gels. Three proteins of approximately 85 kD, 180 kD and 200 kD were detected as cross-linked to I$^{125}$GDNF in cells expressing GDNFRα (FIG. 3). These proteins were absent when the cross-linking reaction took place in the presence of excess unlabeled GDNF or when $^{125}$I GDNF was cross-linked to cells expressing an irrelevant cell surface protein (FIG. 3). The ~80–85 kDa protein band likely represents a complex of the 58 kDa GDNFRα and the 15 kDa GDNF monomer, whereas the higher molecular weight bands may represent interaction between the $^{125}$I GDNF, GDNFRα and putative signaling molecules like Ret (see below) or dimerization of the $^{125}$I GDNF/GDNFRα complex. Cross linking of $^{125}$I GDNF was virtually abolished following treatment with phosphoinositide-specific phospholipase C (PIPLC), an enzyme that specially cleaves GPI- linkage (FIG. 3), supporting the notion that GDNFRα is indeed a high affinity GPI- linked, GDNF binding protein.

Figure 4A:
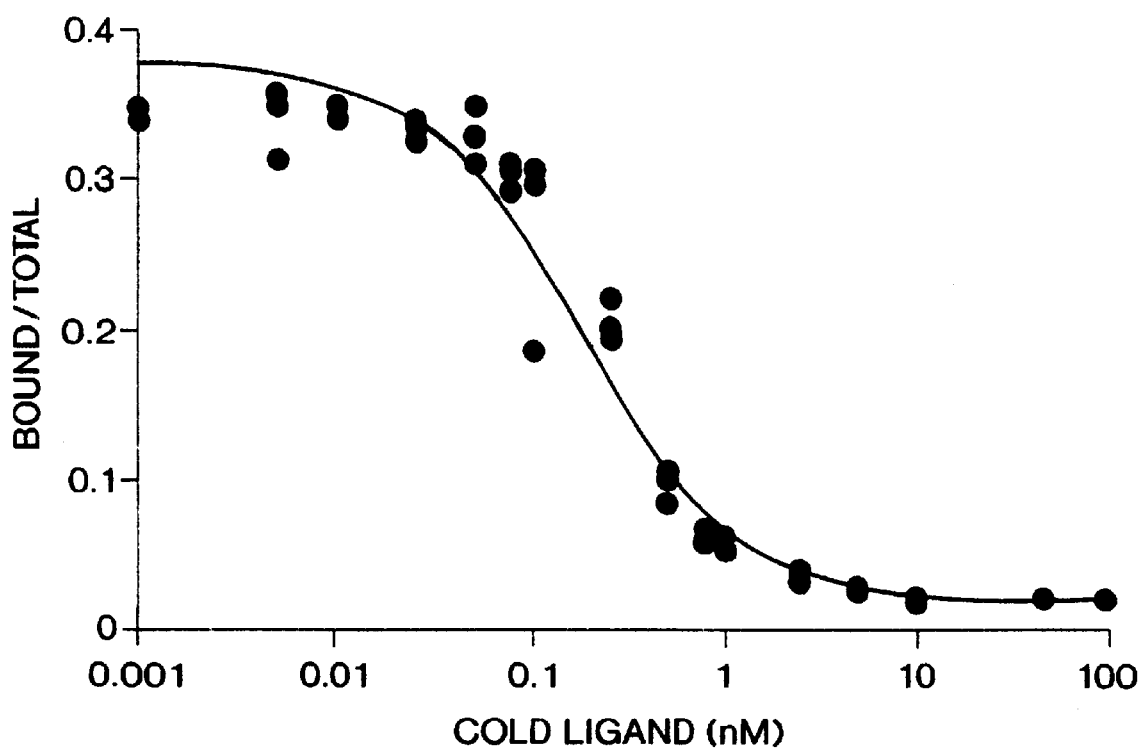
FIGS. 4A–B depict binding of binding of $I^{125}$ GDNF to GDNFRα expressing cells and displacement by unlabeled GDNF. The Scatchard representation FIG. 4B reveals a Kd value of 63 pM determined by the IGOR program.
Figure 4B:
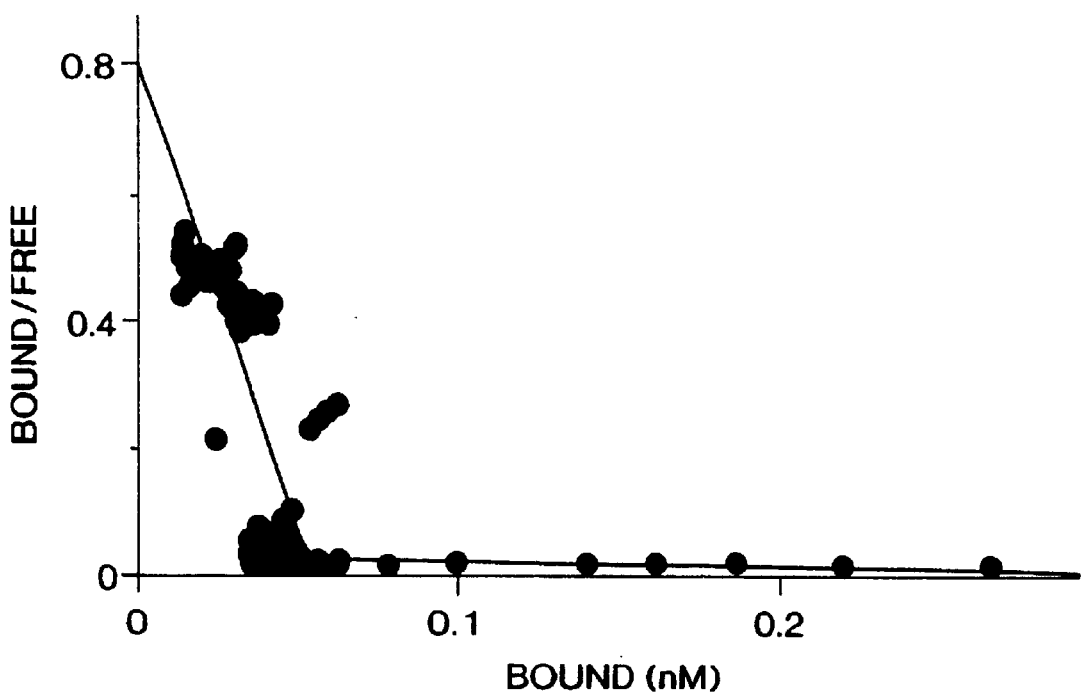

Competition binding experiments further indicate that GDNF binds specifically and reversibly to GDNFRα expressing cells. For equilibrium binding analysis cells were processed as before and incubated with 50 pM $^{125}$I-labeled GDNF and various concentrations of cold GDNF. The IGOR program was used to determine $K_d$. Competition binding of 125I GDNF to Chinese hamster ovary cells stably expressing GDNFRα demonstrated that GDNF binds specifically and reversibly to GDNFRα and that the two proteins interact with an approximate $K_d$ of 63 pM (FIG. 4; Scatchard analysis insert).

Figure 5:
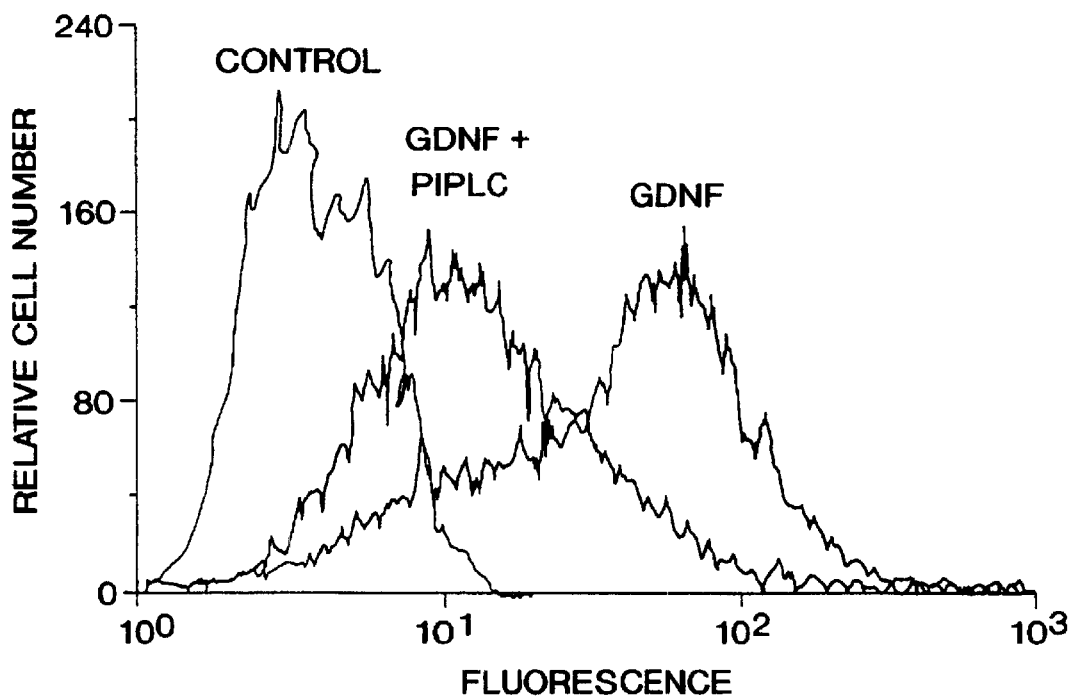
FIG. 5 depicts a fax-sort analysis of cells expressing GDNFRα following PIPLC treatment. Graphs are marked as to sample. "Control" represents cells expressing a control cell surface protein. Dashed line ("GDNF+PIPLC") represent cells expressing GDNFRα that were treated for 1 h at 37° C. with 2 ug/ml PIPLC. Circles ("GDNF") represent cell expressing GDNFRα which were not treated with PIPLC. A shift to the right indicates binding to GDNF. Treatment of GDNFRα expressing cells with PIPLC leads to a reduction of over 90% in the amount of GDNF binding.

As predicted from the presence of consensus sequence for GPI linkage, PIPLC treatment of fax-sorted cells expressing GDNFRα, reduced GDNF binding (FIG. 5). For fax sorting, Chinese hamster ovary (CHO) cells stably expressing recombinant GDNFRα, or an unrelated control protein, under the control of an SV40 promoter, were incubated for 1 h at 37° C. either in the presence or absence of PIPLC (2μg/ml) (Koke et al., *Prot. Exp. Purification,* 2:51–58 (1991)). GDNF (100 ng/ml) and anti-GDNF monoclonal antibodies (60/c; 100 μg/ml) were then added, and the cells were incubated for additional 30 min. Florescent anti-IgG monoclonal antibodies (Vector Inc.) were then added and the cells were fax sorted using a flow cytometer cell sorter. Equilibrium binding of $^{125}$I GDNF to GDNFRα expressing cells was reduced greater than 90% following treatment with PIPLC. These results indicate that GDNFRα is a high affinity GDNF-binding protein.

Example 3
Tissue Distribution of GDNFRα

The tissue distribution of the GDNFRα mRNA was examined using Northern blots as well as in situ hybridization analysis. Northern blot analysis of GDNFRα transcripts in adult rat tissues was performed. Northern blots were performed using commercially available multiple tissues blot (Clontech, Palo Alto, Calif.). The entire coding region of GDNFRα was used as a probe. A transcript of approximately 3.7 kb was detected in adult brain, liver, and kidney under stringent conditions.

In situ hybridization of GDNFRα probe to E14 rat embryo tissues was performed, including midsagittal section, ventral midbrain, spinal cord, and kidney regions. For in situ hybridization, tissues were fixed by immersion in cold 4% formaldehyde, equilibrated in 20% sucrose, sectioned at 20 m, and processed as previously described (Fonnum, *J. Neurochem.,* 24:407–409 (1975)) using the entire coding region of GDNFRα as a probe. In addition, in situ hybridization of E15.5 rat embryos was performed. Embryos were immersion-fixed overnight at 4° C. in 4% paraformaldehyde, then cryoprotected overnight in 15% sucrose. Adult rat brains and spinal cords were frozen fresh. Tissues were sectioned at 16 μm, and processed for in situ hybridization using $^{33}$P-UTP labeled RNA probes as described (Henderson et al. *Science* 266:1062–1064 (1994)). Sense and antisense probes were derived from the N-terminal region of GDNFRα using T7 polymerase. Reverse transcriptase polymerase chain reaction analysis was performed as described (Henderson et al. *Science* 266:1062–1064 (1994)).

GDNFRα transcripts were present in regions where GDNF responsive neurons reside, including ventral midbrain (dopaminergic neurons), ventral spinal cord (spinal motoneurons), and in subpopulations of GDNF-dependent dorsal root ganglia (DRG) neurons. In the nervous system of E14 rat embryos, mRNA for GDNFRα was found in regions like the ventral midbrain and the ventral spinal cord, where GDNF-responsive dopaminergic and motoneurons reside, as well as in the pons, medulla oblongata, choroid plexus, cerebellum primordium, diencephalon, and retina. GDNFRα transcripts were also found in whisker follicles, cutaneous muscles, tongue, kidney, esophagus, midgut, stomach, testis, genital tubercle and anal canal. GDNFRα transcripts are found in the E15.5 rat outer layer of the midbrain tectum, choroid plexus, cerebellar primordium, the olfactory epithelium, whisker pads, genital tubercle, urogenital sinus, testes, the intervertebral discs and trachea. In the adult rat nervous system GDNFRα mRNA was detected in the dorsal root ganglia, ventral horn, retina, lateral septum, pyramidal and granule cells in inner layers of the cortex, geniculate nucleus, ventral midbrain, the superior cerebellum, thalamus, pons, and medulla oblongata. Consistent with the finding that the kidneys and the enteric nervous system fail to develop in GDNF-deficient mice (see Example below), high levels of GDNFRα mRNA are present in developing nephrons and in embryonic smooth and striated muscles around the enteric nervous system in the esophagus, gut and stomach. In the adult, GDNFRα transcripts were also found in the pars compacta region of the substantia nigra, the ventrolateral cell column of the spinal cord, the hippocampal formation, inner layers of the cerebral cortex, lateral geniculate nucleus, superior colliculus, outer margin of cerebellar granule cells, lateral septum, endopiriform nucleus, and ciaustrum. GDNFRα transcripts were also found in non-neuronal tissues including the pituitary, urogenital tract and pancreatic primordium. Motoneurons express both GDNFRα and c-ret. Immunohistochemical staining with Ret antiserum revealed the presence of Ret in a developing nephron. In the kidney both Ret and GDNFRα are expressed in the developing nephrons adjacent to GDNF. In the gut, GDNF and GDNFRα are present between the inner circular and outer longitudinal smooth muscle adjacent to and possibly within the enteric nervous system, whereas Ret is present only in the enteric nervous system.

Example 4
GDNFRα Mediates Response to GDNF

Figure 6:
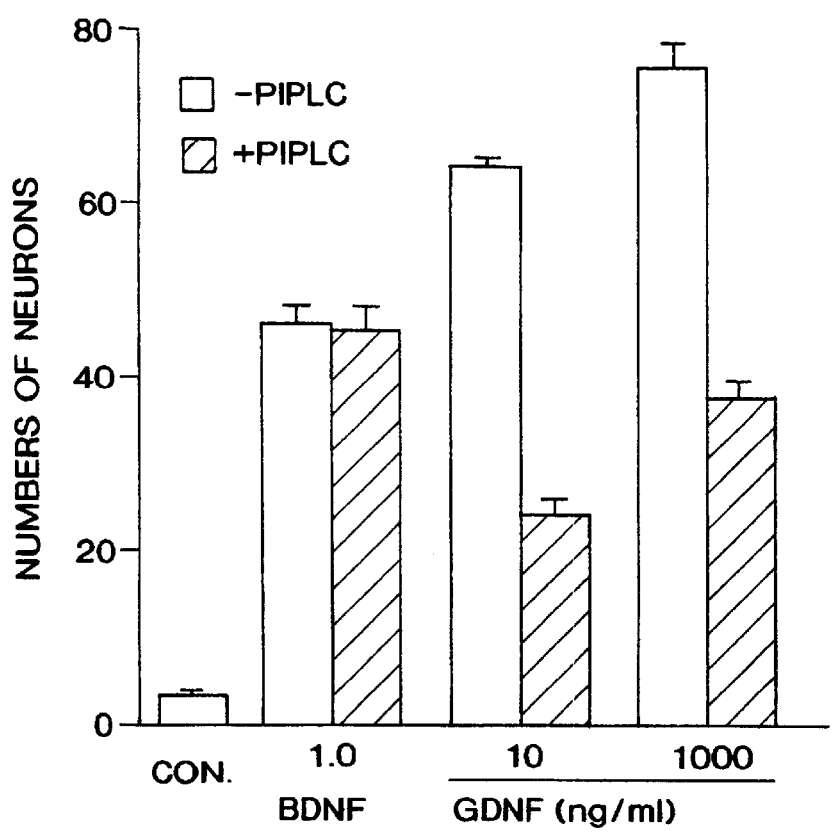
FIG. 6 depicts the response of E6 chick nodose sensory neurons to GDNF before and after PIPLC treatment. Treatment with PIPLC reduces cell survival in the presence of GDNF by over 50%. In contrast, PIPLC does not change the response to BDNF. E6 Chick nodose ganglia neurons were isolated, prepared plated and grown in triplicate wells as previously described (Buj-Bello et al. *Neuron* 15:821–828 (1995)). PIPLC (4 ug/ml) was added to the indicated samples 1 hour prior to as well as 12 and 24 hours following addition. GDNF (10 ng/ml or as indicated) and BDNF (1 ng/ml).
Figure 7:
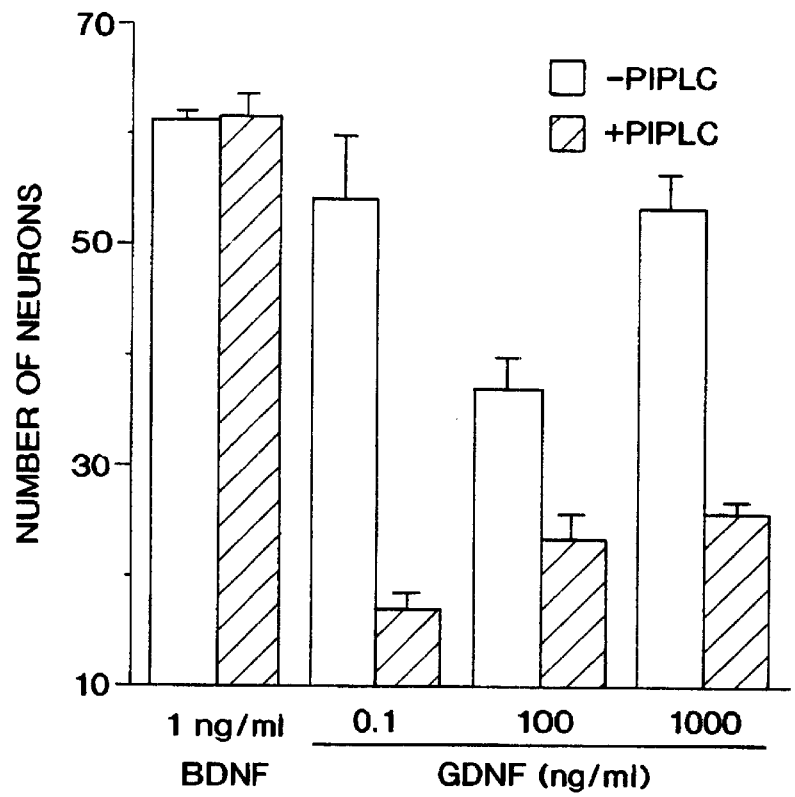
FIG. 7 depicts the response of E14 rat spinal motoneurons to GDNF before and after PIPLC treatment. Treatment with PIPLC reduces motoneurons survival in the presence of GDNF by over 90% without effecting the response to BDNF. Rat embryonic motoneurons were prepared, cultured, and counted as previously described (Bloch-Gallego et al, *Development,* 111:221–232 (1991); Camu et al., *J. Neurosci. Meth.,* 44:59–70 (1992); Henderson et al., *Nature,* 363:266–270 (1993)). Experiments were done in triplicate and the number of motoneurons surviving per $cm^2$ after culture for 50 h is depicted. Motoneurons were treated with the indicated amount of PIPLC 1 h before, with, and 15 h following addition of GDNF (at the indicated concentrations). CNTF (10 ng/ml), Leukemia inhibitory factor (LIF) (10 ng/ml) or BDNF (1 ng/ml).
Figure 8:
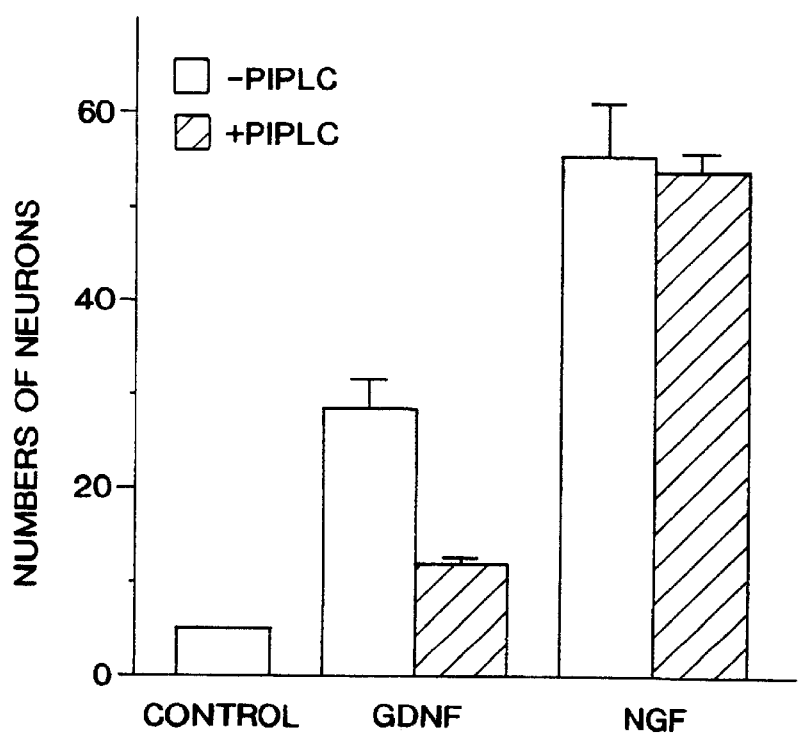
FIG. 8 depicts the response of NGF-responsive standard primary neuron culture to GDNF before and after PIPLC treatment. Treatment with PIPLC reduces neuron survival in the presence of GDNF by over 50% without effecting the response to NGF.
Figure 9A:
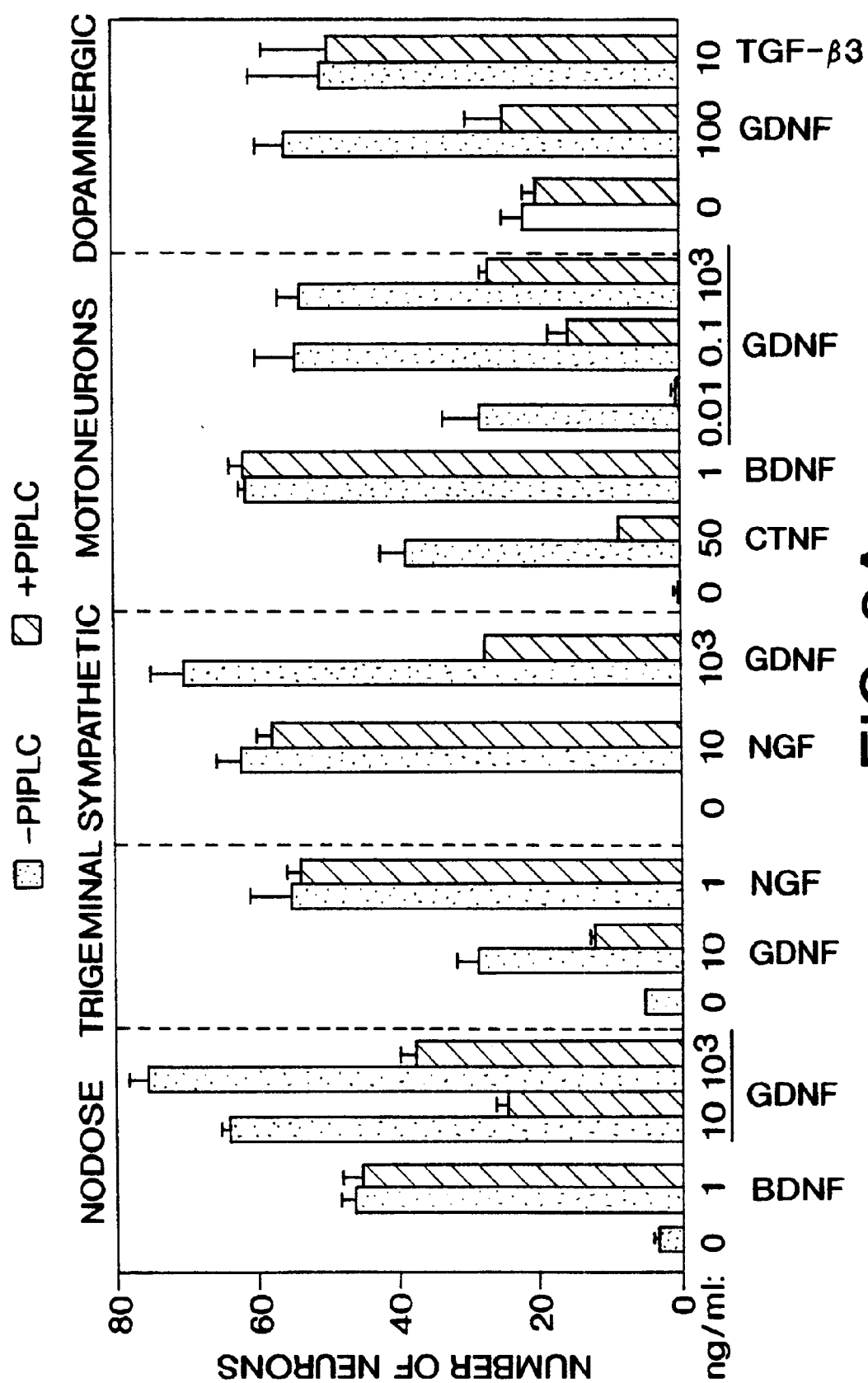

To determine that GDNFRα protein is an essential physiological mediator of GDNF, primary embryonic, cranial sensory, and motor neurons were treated with PIPLC (phosphoinositide-specific phospholipase C (PIPLC) which specifically cleaves GPI-linked proteins (Shukla, *Life Sci.,* 10:1323–1335 (1982); Rhee et al., *Science,* 244:546–550 (1989)) and their survival in the presence of GDNF or other factors was monitored. Embryonic chick nodose, trigeminal and sympathetic ganglia neurons (Buj-Belio et al., *Neuron* 15:821–828 (1995)), E14 rat motoneurons (Henderson et al. *Science* 266:1062–1064 (1994)) and E14 dopaminergic neurons (Bazan, *Proc. Natl. Acad. Sci. USA,* 87:6934–6938 (1990)) were isolated, plated and grown in triplicate wells. PIPLC (2–4 μg/ml) was added to the indicated samples 1–2 h prior to as well as 12 h and 24 h following addition of the indicated growth factors and the number of surviving neurons was determined 30 and 72 h later. The number of embryonic chick nodose and trigeminal ganglion sensory neurons or sympathetic neurons surviving in the presence of saturating concentrations of GDNF was reduced by 50–70% following PIPLC treatment. No changes in the response of these neurons to brain-derived neurotrophic factor (BDNF) or nerve growth factor (NGF) was observed in the presence of PIPLC (FIGS. 6 and 9A). Likewise PIPLC treatment reduced the number of E14 spinal motoneurons or of dopaminergic neurons that survived in the presence of GDNF by 50–90% without effecting survival of these neurons in the presence of BDNF or TGFβ3 (FIGS. 7 and 9A). In these different systems, PIPLC reduced the survival promoting effects of GDNF at GDNF concentrations as low as 10 pg/ml, suggesting that the GPI-linked receptor molecule is necessary for the high-affinity response to GDNF. In addition, PIPLC was effective even when GDNF was applied at 1 μg/ml ($2 \times 10^8$ fold above the $EC_{50}$) for nodose sensory neurons ($EC_{50}$ for chick nodose neurons is 6.1 ng/ml; Buj-Bello et al., *Neuron*, 15:821–828 (1995)) and at 0.1 pg/ml for motoneurons (Henderson et al., *Science*, 266:1062–1064 (1994)). These high concentrations did not reverse the effect of PIPLC treatment (FIGS. 6, 7, and 9A), excluding the possibility that the GPI-linked protein, following its release from the cell membrane, binds GDNF and reduces its effective concentration (FIG. 9A).

Antisense oligonucleotides to GDNFRα were used to block GDNFRα expression in primary embryonic motor and cranial sensory neurons. Oligodeoxynucleotides were synthesized against regions of the GDNFRα shown in FIG. 1. Whereas GDNF promoted the survival of these neurons in control cultures and in cultures containing sense oligonucleotides, no response to GDNF was observed in cultures containing antisense oligonucleotides. In contrast, the survival promoting effect of BDNF was the same in cultures containing GDNFRα antisense oligonucleotides and in control cultures.

a soluble GDNFRα protein was generated and used to restore GDNF response in PIPLC-treated motor and sensory neurons. Previous studies demonstrated that addition of a soluble form of the GPI-linked CNTF receptor (CNTFRA) led to the acquisition of a response to CNTF (Davis et al., *Science*, 259:1736–1739 (1993); Panayotatos et al., *Biochem.*, 33:5813–5818 (1994)). In the present case, as above, GDNF alone failed to prevent the death of many PIPLC-treated motoneurons, however, addition of soluble GDNFRα at 100 ng/ml completely restored the survival promoting effects of GDNF in PIPLC-treated, primary motor and sensory neurons (FIG. 9B). Thus, GDNFRα is expressed on GDNF-responsive neurons, and like the receptors for CNTF (Davis etal., *Science*, 253:59–63 (1991); Ip et al., *Neuron*, 10:89–102 (1993)) and endotoxin (LPS) (Lee et al., *Proc. Natl. Acad. Sci. USA*, 90:9930–9934 (1993)), is anchored to the cell membrane by a glycosyl-phosphatidyl inositol ("GPI") linkage (Low et al., *Science*, 239:268–275 (1988)).

Neurite outgrowth activity was determined with PC12 cells. Rat pheochromocytoma PC12 cells, which are dependent on neurotrophic factors for survival in serum-free media, and express low levels of Ret (data now shown) were grown without serum in the presence of GDNF, soluble GDNFRα or both and examined 7 days later. Soluble GDNFRα, which was produced as a carboxy terminus His tagged protein in 293 human embryonic kidney cells, was purified by Ni-NTA chromatography as described (Moran et al, *J. Biol Chem.*, 266:1250–1257 (1991)). PC12 cells, were seeded on collagen polyornithine-coated 35 mm dishes in RPMI medium supplemented with 10% horse serum and 5% fetal calf serum. Following attachment, the cells were switched to serum-free medium and then exposed to GDNF (100 ng/ml) and soluble GDNFRα (sRα) as indicated (FIG. 9C). The number of live neurite-bearing phase bright cells per microscopic field was determined 7 d later as described (Micanovic et al., *Proc. Natl. Acad. Sci USA*, 87:157–161 (1990)). With GDNF or soluble GDNFRα alone, only a few neurite-bearing, phase-bright, live cells were found. In contrast, when PC12 cells were exposed to both GDNF and soluble GDNFRα, an increase in the number of living cells with neurites was observed (FIG. 9C). The combination of soluble GDNFRα (sR=α) and GDNF induced neurite-outgrowth response of PCI2 cells. Soluble GDNFRα imparted GDNF-responsiveness to PC12 cells. GDNFRα is thus an important component of the GDNF signaling cascade and has the properties expected of a ligand-binding subunit of a functional GDNF receptor.

Example 5
GDNFRα and Ret Form a GDNF- Receptor Complex

Since GDNFRα is anchored to the outer surface of the cell, transmission of GDNF signals following binding to GDNFRα must involve an additional transmembrane protein. Other members of the TGFβ protein superfamily, of which GDNF is a member, that have a GPI-linked binding protein have a transmembrane serine threonine kinase receptor as well as (for reviews see: Massagud et al., *J. Biol. Chem.*, 266:20767–20772 (1991); Cheifetz et al., *J. Biol. Chem.*, 266:20767–20772 (1991)). The structure of GDNFRα indicates that a receptor complex for GDNF, like the receptor complexes for CNTF (Davis et al., *Science* 260:1805–1809 (1993)) and for endotoxin (LPS) (CD 14; Lee et al., *Proc. Natl. Acad. Sci. USA*, 90:9930–9934 (1993)), will be composed of multi-subunits, including a ligand-binding component (GDNFRα disclosed herein) and a trans-membrane, signal-transducing molecule such as gp130. The phenotype of mice lacking the orphan tyrosine kinase receptor c-ret (Schuchardt et al., *Nature* 367:380–383 (1994); recently confirmed by Durbec et al. *Nature* 381:789–793 (1996)) have a striking similarity to the phenotype of the GDNF-deficient mice first made and examined herein (see below). In addition, the tissue distribution of Ret (Pachnis et al. *Development* 119:1005–1017 (1993); Avantaggiato et al. *Cell Growth Diff.* 5:305–311 (1994); Tsuzuki et al. *Oncogene* 10:191–198 (1995); Davis et al. *Science* 259:1736–1739 (1993)) was similar to that for GDNFRα (data not shown). To confirm that GDNF has a transmembrane receptor, namely Ret, that complexes with GDNFRα to signal and mediate a GDNF response, physical interaction of GDNFRo and Ret were determined. The human neuroblastoma SKN-SH and the mouse neuroblastoma Neuro-2a, cell lines that express endogenous c-ret, were exposed to GDNF alone or to GDNF in combination with soluble GDNFRα for 5 minutes and the level of Ret tyrosine phosphorylation was determined. To assay for tyrosine phosphorylation of Ret, cells were incubated for 1 h at 37° C. with or without PIPLC and then exposed to various concentrations of GDNF and soluble GDNFRα for 5–10 min. at 37° C. Cells were then removed from the plates with 2 mM EDTA in PBS and lysed with ice-cold buffer (10 mM sodium phosphate [pH 7.0], 100 mM NaCl, 1% NP40, 5 mM EDTA, 100 mM sodium vanadate, 2 mM PMSF, and 0.2 units of aprotinin) and used for immunoprecipitation with antisera raised against the 19 amino acid carboxyl terminus of Ret, followed by binding to Protein A SEPHAROSE. The immunoprecipitated proteins were released by boiling in SDS sample buffer, separated on an 8% SDS-polyacrylamide gel, transferred to a nitrocellulose membrane and reacted with anti-phosphotyrosine antibody (Upstate Biotechnology, Inc.); detection was with an ECL Western blotting detection system (Amersham Life Science). To increase the level of Ret, SK-N-SH cells were treated with 10 nM retinoic acid 12 h before addition of GDNF.

Figure 10A:
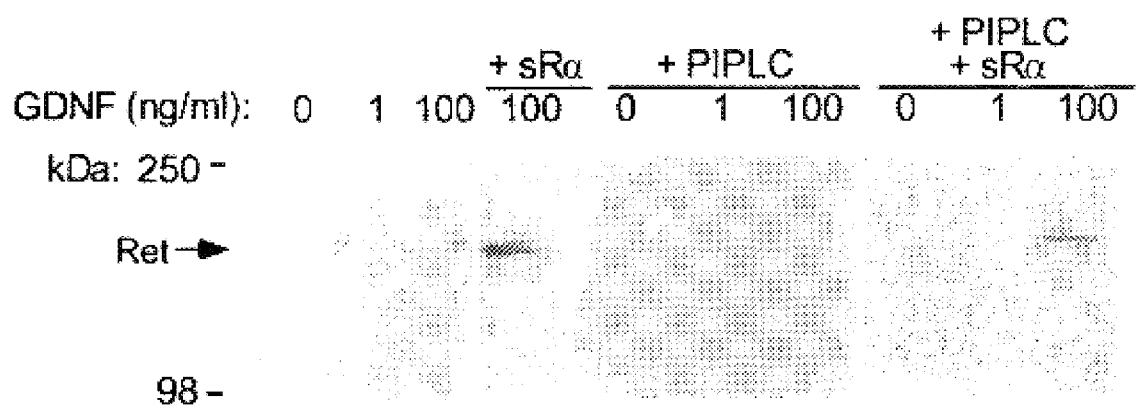
FIGS. 10A, 10B, 10C, and 10D depict involvement of Ret in the response to GDNF.

GDNF induced modest phosphorylation of Ret in these two cell lines (FIG. 10A) but not in NIH3T3 cells stably expressing the human Ret (data not shown). Ret phosphorylation was further increased when GDNF was added together with GDNFRα, but not when GDNFRα was added alone (FIG. 10A and data not shown). To determine whether induction of Ret tyrosine phosphorylation is dependent on the presence of GDNFRα, Neuro-2a cells and SK-N-SH cells were treated with PIPLC and the response of Ret to GDNF was examined. In agreement with the finding that survival responses to GDNF require the presence of GDNFRα, no induction of tyrosine phosphorylation on Ret was detected in these PIPLC-treated cells in the presence of GDNF alone. In contrast, stimulation of tyrosine phosphorylation of the 170 kDa Ret protein was readily observed in PIPLC treated Neuro-2a and SK-N-SH cells when GDNF was added together with a soluble GDNFRα (FIG. 10A and data not shown).

Figure 10B:
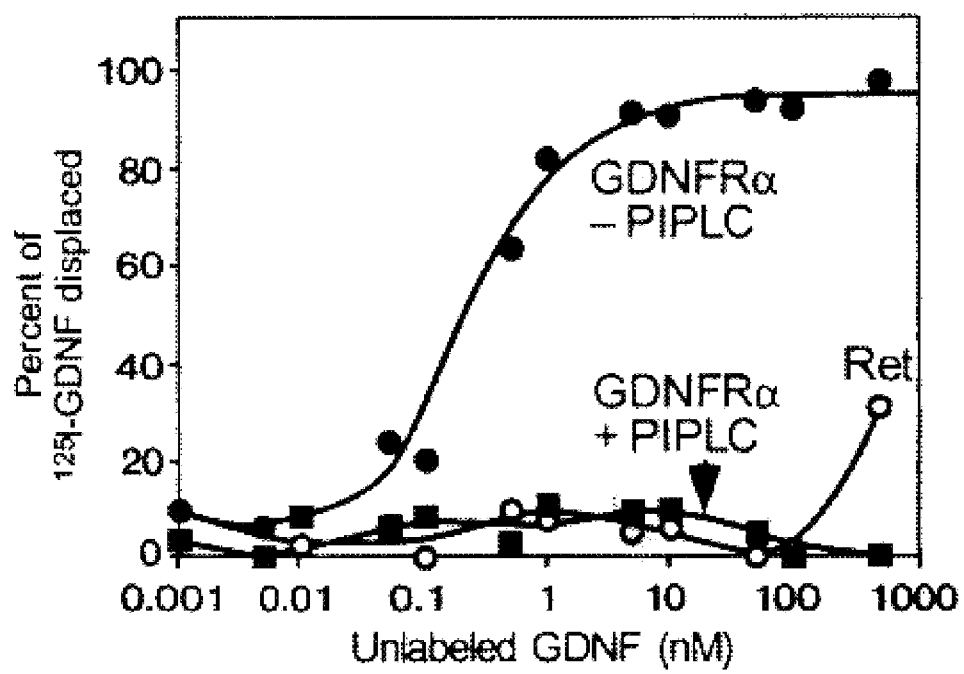
Figure 10C:
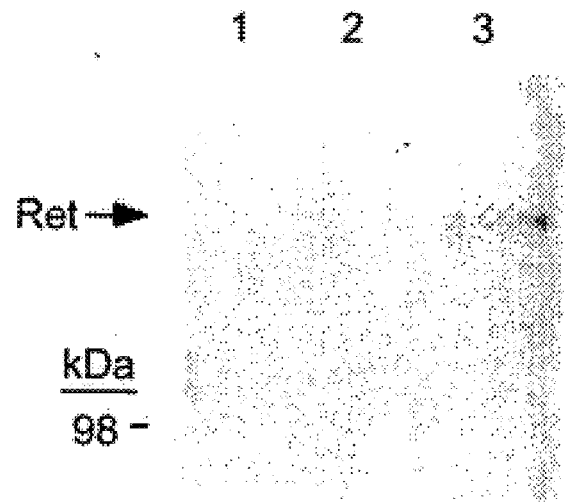
Figure 10D:
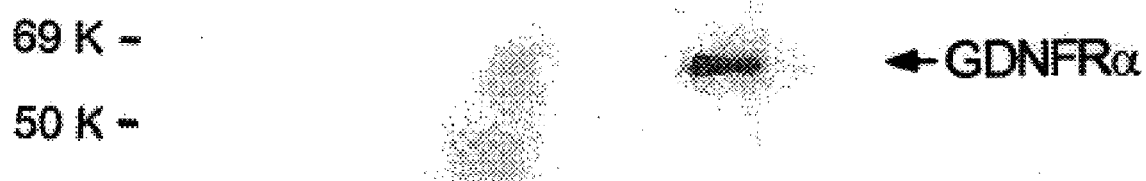

Although GDNF stimulated tyrosine phosphorylation of Ret, no high affinity binding of GDNF to Ret could be detected in Neuro-2a cells expressing high levels of an endogenous Ret or in cells expressing recombinant Ret protein (FIG. 10B and data not shown). The physical interaction between Ret and GDNF, as defined by the formation of an immunoprecipitable Ret IGDNF complex, which could be mediated by GDNFRα, was determined. Human embryonic kidney 293 cells were transiently transfected with an expression vector containing c-ret or with a combination of expression vectors for c-ret and GDNFRα, exposed to GDNF and then lysed with a mild detergent (Davis et al. *Science* 259:1736–1739 (1993)). Proteins that formed complexes with GDNF were immunoprecipitated with polyclonal antibody to GDNF and analyzed on a Western blot using polyclonal antibody to Ret. In cells expressing Ret alone, or GDNFRα alone, no co-immunoprecipitated Ret protein could be detected. In contrast, Ret was readily co-immunoprecipitated by GDNF antibodies from cells that express both Ret and GDNFRα (FIG. 10C). To further characterize the complex between GDNFRα and Ret, 293 cells were transiently transfected with expression vectors for c-ret and with an epitope tagged GDNFRα and then analyzed for the presence of GDNFRA/Ret protein complexes in the presence or absence of GDNF. Cells were stimulated with GDNF as indicated and lysed with Brij 96 detergent (Sigma) as described (Davis et al., *Science*, 259:1736–1739 (1993)). Putative immune complexes were immunoprecipitated with a polyclonal antibody against GDNF (FIG. 10C) or Ret (FIG. 10D) transferred onto a nitrocellulose filter and then analyzed with polyclonal antibody against Ret (FIG. 10C) or the epitope tagged GDNFRα (FIG. 10D). In cells that expressed Ret alone or the epitope tagged GDNFRα alone, no significant level of protein complexes could be detected, either in the presence or absence of GDNF (FIG. 10D). In contrast, in cells expressing both epitope tagged GDNFRα and Ret, a protein complex containing both proteins was readily detected following exposure to GDNF (FIG. 10D). These findings are consistent with the idea that GDNF, GDNFRα and Ret can, in the presence of GDNF, form a complex on the cell surface, that Ret is a component of a functional GDNF receptor, and that GDNFRα is a required intermediary in the interaction between GDNF and Ret.

Example 6

The mouse GDNF gene was disrupted by homologous recombination in embryonic stem ("ES") cells and a targeted clone was injected into blastocysts to generate GDNF mutant mice. Amino acids 103–211 of the mature biologically active portion of GDNF (see FIG. 1) missing from the targeting construct produced the disrupted allele. The targeting construct was created as follows. A 3 Kb Sph 1-Eco R1 genomic fragment encoding amino acids 52–102 of GDNF was fused in-frame to the lacZ gene. A neo$^\gamma$ gene under the control of PGK promoter and a 3.1 kb Bgl II-Bam HI fragment from the 3' end of the GDNF gene were inserted immediately downstream of the lacZ gene. GDNF gene fragments were obtained from a murine 129 lambda library. The targeting construct was electroporated into ES-D3 cells. G418 (400 micrograms/ml) resistant clones were isolated. ES targeted clones were injected into BALB/c blastocysts and a single clone was transmitted through the germline. Homologous recombination event in a single ES clone was determined by Southern hybridization. Southern blots were used to confirm the disruption. Genotype analysis of wild-type (+/+), heterozygous (+/−) and homozygous mutants (−/−) animals was determined by PCR. In the analysis, an upper band observed was specific for the neo$^\gamma$ gene and a lower band was specific for the wild-type GDNF gene.

Mutant mice were examined. Whereas GDNF mRNA was found in the kidney, intestine, ventral midbrain and skeletal muscle of normal E15.5 mice, no GDNF transcripts could be detected in litter mates homozygous for the mutant allele (GDNF$^{−/−}$). Heterozygous mice were normal in size and were indistinguishable from their wild-type (WT) litter mates. In contrast, although GDNF$^{−/−}$ mice were able to suckle and had normal limb and body movements, they died 1–1.5 days after birth.

GDNF was first identified by its ability to prevent the death of embryonic dopaminergic neurons in culture (Lin et al. *Science* 260:1130–1132 (1993)) and in lesion models in vivo (Beck et al. *Nature* 373:339–341 (1995); Kearns et al. *Brain Res.* 672:104–111 (1995); Tomac et al. *Nature* 373:335–339 (1995)) and was subsequently shown to be expressed in the embryonic striatum, a major innervation target for dopaminergic neurons (Schaar et al. *Exp. Neurol.* 124:368–371 (1993); Stromberg et al. *Exp. Neurol.* 124:401–412 (1993); Poulsen et al. *Neuron* 13:1245–1252 (1994)). Whether GDNF is an essential survival factor for dopaminergic (DA) neurons during normal development was examined. The number of neurons in different ganglia in p1 WT and GDNF$^{−/−}$ mice was determined. Neuron type examined included dopaminergic, facial motor, spinal motor, noradrenergic, trigeminal, nodose, DRG, petrosal, vestibular, and SCG. Animals were processed and neuronal counts were preformed as in Jones et al. (*Cell* 76:989–999 (1994)). The number of ganglia was recorded. The striatum, ventral midbrain, substantia nigra, locus coeruleus, and facial motonuclei in the GDNF$^{−/−}$ mouse was examined after tyrosine hydroxylase (TH) staining and compared to P1 WT and GDNF−/− mice. TH is the rate limiting enzyme in dopamine synthesis. A reduction in the density of TH fibers in the striatum of the GDNF$^{−/−}$ mouse was observed. Animals were anesthetized and perfusion fixed with 4% paraformaldehyde in 0.1M phosphate buffer sectioned stained and analyzed as described (Jones et al. *Cell* 76:989–999 (1994)). Surprisingly, the number of tyrosine hydroxylase positive (TH+) dopaminergic neurons in the ventral midbrain and the density of dopaminergic projections to the striatum were identical in GDNF$^{−/−}$ and WT animals.

Since development of DA neurons in mammals is protracted and continues postnatally (Coyle et al *J.Neurochem.* 27:673–678 (1976); Specht et al *Comp. Neurol.*

199:255–276 (1981)), the number of TH+ cells in the midbrain of P42 GDNF$^{+/-}$ heterozygous mice was compared. The results are presented in Table 1.

TABLE 1

Number of neurons in different ganglia in P42 WT and GDNF$^{+/-}$ mice

| Neuron Type | Wild Type (N = 8) | GDNF$^{het}$ (N = 12) |
|---|---|---|
| Facial MN | 1701 ± 55.8 | 1657 ± 54.4 |
| Dopaminergic | 118.04 ± 7.34 | 112.88 ± 9.04 |
| Noradrenergic | 1218.5 ± 91.24 | 1068 ± 38.19 |

Table legend: The processing of animals and count of TH-immunoreactive cell numbers in the entire pars compacta region of the substantia nigra was conducted as previously described (Sauer et al. Proc. Natl. Acad. Sci. USA 92:8935-8939 (1995)). Cell counts are represented as the mean number of cells per section per animal. Count of TH-IR cell numbers in the locus coeruleus was performed by counting the number of TH-IR cell profiles present in every hindbrain section containing the locus coeruleus. Cell numbers are represented as cumulative counts on both sides of each animal. Counts in the facial motor nucleus were done from cresyl violet-stained sections by a naive observer. The total number of stained neuronal perikarya in all subnuclei of the facial motor nucleus were counted in every third section on both sides of the brainstem. Cell numbers are presented as total cell counts +/– SEM per animal. All microscopy was conducted under bright-field illumination at ×200 magnification. N represent that number of ganglia analyzed.

Surprisingly, no deficit in the number of dopaminergic neurons (Table 1) or in the complexity of TH+ fibers in the striatum was detected in GDNF$^{+/-}$ mice. These results indicate that GDNF is not a required survival factor for embryonic dopaminergic neurons and is not a limiting survival factor for dopaminergic neurons in the adult, as had been previously suggested (Lin et al. Science 260:1130–1132 (1993); Beck et al. Nature 373:339–341 (1995); Kearns et al. Brain Res. 672:104–111 (1995); Tomac et al. Nature 373:335–339 (1995)).

GDNF is a potent neurotrophic factor for embryonic spinal motoneurons in culture and prevents the death of lesioned facial motorneurons in vivo (Henderson et al. Science 266:1062–1064 (1994); Yan et al. Nature 373:341–344 (1995); Oppenheim et al. Nature 373:344–346 (1995)). Whether GDNF, expressed in skeletal muscle, is required for motoneuron survival during embryogenesis was determined. Small deficits were detected in the lumbar spinal and trigeminal (<20%) but not facial nuclei of P1 GDNF$^{-/-}$ mice. In addition, no deficit in facial motomeurons was observed in P42 GDNF$^{+/-}$ animals (Table 1). These findings argue against the possibility that GDNF is a major neurotrophic factor for voluntary motoneurons during the period of naturally occurring cell death (Henderson et al. Science 266:1062–1064 (1994); Yan et al. Nature 373:341–344 (1995); Oppenheim et al. Nature 373:344–346 (1995)).

GDNF was recently shown to prevent the chemically induced death of noradrenergic neurons in the locus coeruleus and to promote their fasciculation and sprouting in whole animals (Arenas et al., Neuron 15:1465–1473 (1995)). These findings suggested that GDNF may be a natural neurotrophic factor and a potential therapeutic agent for noradrenergic neurons which degenerate in Alzheimer's and Parkinson's diseases. Upon examination, noradrenergic, locus coeruleus neurons were found to be normal in size and in number in both the P1 GDNF$^{-/-}$ and in P42 GDNF$^{+/-}$ (Table 1) mice. Likewise, although GDNF is upregulated in the hippocampus, cortex, and striatum following chemically induced epileptic seizure or injection of excitatory neurotransmitters (Schmidt-Kastner et al. Brain Res. Mol. Brain Res. 26:325–330 (1994); Humpel et al Neuroscience 59:791–795 (1994)), no gross deficits were identified in the cerebellum, basal forebrain, hippocampal formation, striatum and neocortex of P1 GDNF$^{-/-}$ mice. Only a small deficit in spinal motoneurons (<20%) and no deficit in noradrenergic or dopaminergic neurons, at post natal day 1 (P1) was observed. These findings suggest that the presence of GDNF in the embryonic CNS and in innervation targets may reflect, at least in part, involvement in differentiation, regulation of axonal sprouting, synaptogenesis, choice of neurotransmitters, conduction velocity or synaptic efficacy.

Consistent with the observation that GDNF promotes the survival of chick embryonic sympathetic and nodose sensory neurons in culture (Buj-Bello et al. Neuron 15:821–828 (1995)), a reduction in the number of sympathetic superior cervical ganglion (<35%), nodose neurons (<40%), as well as in dorsal root ganglia (<40%) neurons was detected. In contrast, no deficit in the number of trigeminal or vestibular ganglia neurons was noticed.

The enteric nervous system in WT and GDNF$^{-/-}$ mice was examined. Small intestine from WT and GDNF$^{-/-}$ mice was stained with H&E or with antibodies against the neuronal specific protein peripherin. P1 mice, E13.5 mice were examined. Myenteric (Myn) and submucosal (Sub) neurons in WT animals were absent in GDNF$^{-/-}$ mice. Animals were perfusion fixed with 10% neutral buffered formalin, paraffin embedded and sectioned at 5 μm for light microscopic analysis. Antibody staining was performed as in (Jones et al. Cell 76:989–999 (1994)), using polyclonal anti-peripherin antibodies (Chemicon Inc.) at 1:300 dilution. The myenteric (Auerbach) and submucosal (Meissner) plexi were examined for neuronal deficits. Enteric nervous system (ENS) neurons belonging to these 2 plexi were readily visible along the length of the gastrointestinal tract in E13.5, E15.5, and P1 WT and GDNF$^{+/-}$ mice by light microscopy as well as following staining with an antibody against the neuronal specific marker peripherin. In contrast, these neurons were completely absent in aged matched GDNF$^{-/-}$ litter mates. Furthermore, the muscle wall of the intestine was thinned in GDNF$^{-/-}$ relative to their WT or GDNF$^{+/-}$ litter mates. Although the ENS originates prirnarily from neural crest cells of the hindbrain region, a significant effect on other neural crest derived neurons was not observed. These combined findings suggest that GDNF is essential for the survival and/or development of enteric neurons shortly after they enter the embryonic bowel (Gershon et al. J. Neurobiol. 2:199–214 (1993)), and that GDNF induced innervation may be required for the development and/or maintenance of smooth muscles in the intestine. Absence of the ENS was previously noted in mice lacking the orphan tyrosine kinase receptor RET (Schuchardt et al. Nature 367:380–383 (1994)). GDNF has been reported as abundantly expressed in the smooth muscles layers of the intestine during embryogenesis and the presence of GDNF mRNA in the embryonic kidney mesenchyme had been reported (e.g., Trupp et al. J. Cell Biol. 130:137–148 (1995)).

The kidneys in WT, GDNF$^{-/+}$ and GDNF$^{-/-}$ mice were examined. Low power photomicrographs of abdomen in P1 WT, P1 GDNF-/-, P1 GDNF+/-, and P42 GDNF$^{+/-}$ mice were obtained. The position of the kidneys was adjacent to the adrenal glands in the WT mice; however, they were absent in the GDNF$^{-/-}$ and he left kidney was absent in P1 and P30 GDNF$^{+/-}$ mice. H&E staining of sagginal sections form in E13.5 WT, E13.5 GDNF$^{-/-}$ embryos, E11.5 WT, E 11.5 GDNF-/- was performed. Ovary (Ovr) was present in the space normally occupied by the kidney (Kid), just caudal to the adrenal (Adr). WT, GDNF$^{-/-}$ and GDNF$^{+/-}$ mice were killed at the indicated age, perfused with 10% neutral buffered formalin, embedded in paraffin, serially sectioned, and stained with H&E for microscopic examination. The GDNF genotype of each pup was determined by PCR analysis, the sex was determined by microscopic analysis of gonads and 2–3 animals were histologically analyzed from each genotype and at each age.

14/16 GDNF$^{-/-}$ mice had complete bilateral renal and ureteral agenesis, with partial development of one of the two kidneys and ureter was observed in a two GDNF$^{-/-}$ embryos. In heterozygote embryos, pups and adults of both sexes, there was an increased incidence of unilateral renal agenesis (7/26) or hypoplasia (4/26) relative to WT mice. Analysis of GDNF$^{-/-}$ mice at early embryonic stages revealed the absence of metanephric kidneys as early as E11.5. Other derivatives of embryonic urogenital intermediate mesoderm (adrenal and gonads), remaining abdominal viscera and all thoracic tissues were microscopically normal in both GDNF$^{+/-}$ and GDNF$^{-/-}$ mice. With respect to the reproductive organs, the single noted change in GDNF$^{-/-}$ mice was a reversal in the orientation of the ovary in relation to the abdominal viscera. This change may reflect an increase in available space in the abdominal cavity following renal agenesis or modifications in the mesothelial that attaches the ovary to the body wall.

In addition the GDNF$^{-/-}$ mice displayed a mild multifocal necrosis in the splenic red pulp which are sites of active hematopoiesis. Spleens from the 1 day old (P1) GDNF wild type and the mutant GDNF-knock-out (KO)mice, as well as wildtype KO embryos at day 16.5 (E16.5), E15.5, E13.5 and E12.5 of gestation were examined. All of these examinations were done on 10% neutral buffered formalin fixed (14 hours), paraffin embedded, 5 micron sections which were stained with hematoxylin and eosin for microscopic evaluation using standard procedures for evaluating morphologic changes in tissues. At all the time points examined, there was production of hematopoietic elements (erythroid- red blood cell series- and myeloid -white blood cell series, including neutrophils, eosinophils, lymphocytes and macrophages) in the liver. This is a normal process during development which is still present at birth in mice and it appeared normal in both the wild type and KO mice. Similar production of erythroid and myeloid elements also takes place in the red pulp of the spleen, developing around E13.5 and persisting throughout the lifespan of mice. However, in the E16.5 KO (1 animal) and the 3 P1 KO mice examined, there were multiple scattered foci of necrosis in the red pulp, frequently adjacent to blood vessels. (The foci in the E16.5 embryo were less dramatic than those observed in the P1 mice. These foci were surrounded by developing erythroid and myeloid cells, indicating that these foci originated in hematopoietic islands where active cell proliferation takes place. These areas of necrosis frequently, but not always, were adjacent to veins in the parenchyma. These veins are the sites where the mature erythroid and myeloid cells enter the peripheral circulation. There was no evidence of thrombosis or infection to suggest another etiology for these necrotic foci. The absence of similar foci at any developmental age in wild type litter mates suggests that it is not due to infection or a condition in the dam (an "environmental"factor, of sorts) but is directly related to the KO genotype. These foci were not observed in the E15.5 and E13.5 KO mice, but this is because the splenic hematopoiesis at these gestational ages is just beginning to develop. At E16.5, hematopoiesis is also beginning in the bone marrow cavities, the major site of production after birth. Similar necrotic foci in the bone marrow in E16.5 or P1 KO mice or in the liver of KO was not seen at any of the gestational ages examined. The presence of necrotic foci in hematopoietic islands in the splenic red pulp of KO mice suggests that GDNF has an effect on splenic hematopoiesis.

The essentially normal development of gonads in GDNF$^{-/-}$ mice indicates that GDNF is not required for organogenesis of pro-nephric or mesonephric kidneys (transient structures that participate in the formation of both the definitive kidney and the gonads) (Saxen, Organogenesis of the kidney (ed. P. W. Barlow, P. B. Green, and C. C. White), Vol. 19, Cambridge University Press, Cambridge. UK (1987)). Instead, GDNF appear to be essential during the period when reciprocal inductive interactions between the ureteric bud (an evagination of the mesonephric/Wolffilan duct) and the metanephric mesenchyme (caudal intermediate mesoderm) give rise to the collecting ducts (ureter) and the filtering system (the renal corpuscle and proximal and distal tubules) of the metanephric permanent kidney. Interestingly, bone morphogenic factor-7 (BMP-7), another member of the TGF-β protein family, has been shown to be essential for growth and survival of the ureter and nephrons but not for their induction (Dudley et al. *Genes & Develop.* 9:2795–2807 (1995)), suggesting that multiple members of the TGF-β protein family may regulate distinct aspects of renal development. In addition, defects in kidney development (as well as other organs) were observed in mice lacking the orphan tyrosine kinase receptor RET (Schuchardt et al. *Nature* 367:380–383 (1994)) and in mice lacking the Willms tumor associated, putative transcription factor, WT-1 (Kreidberg et al. *Cell* 74:679–691 (1993)). Accordingly, as demonstrated herein, GDNF is involved in kidney organogenesis (Patterson and Dressler, *Curr. Opin. Genet. Dev.* 4(5):696–702 (1994)) to control growth cell differentiation and patterning in this organ.

A number of relatively young (5–7 week old) GDNF heterozygous mice were observed to be disheveled, with poor hair coat and weight loss. Four out of 8 were found to have severe, end stage renal disease. Examination of the kidneys revealed the microscopic appearance of a 1 or 2 year old kidney (when end stage renal disease is usually seen in mice). The lesions appeared to be primarily glomerular in origin, characterized by shrunken sclerotic glomeruli and increased glomerular matrix (membranous glomerulonephritis). One animal had increased acellular mesangial matrix, suggestive of glomerular amyloidosis, but special stains were negative for amyloid. This material was PAS positive, which indicates it is probably mesangial matrix. Secondary changes observed were tubular dilation and proteinuria. In terminal animals, BUN and creatinine levels were increased, which generally occurs very late in renal disease when >70% of the renal mass is lost. As shown above, some GDNF heterozygotes have only 1 kidney; however, this severe renal disease was seen in animals that had 1 or 2 kidneys (and in both sexes). These results indicate that the disease present in GDNF heterozygotes is a membranous glomerulonephritis.

Seven pairs of age-matched GDNF wild type and heterozygous mice were screened by clinical pathology, hematology, and light and electron microscopy. These mice were 21–23 weeks old, and except for a slight elevation of BUN (34 vs 25) in the heterozygotes, there was no evidence of renal disease. We did some electron microscopy on the heterozygotes with the highest BUN (44), but it was generally ultrastructurally normal. There were some areas where the epithelial pedicles were fused. Since these animals were much older than those examined at necropsy previously, they probably were not susceptible to the renal disease.

In summary, the work presented herein demonstrates that GDNF is not an essential neurotrophic factor for dopaminergic, motor, or noradrenergic neurons during embryogenesis as previously suggested. Rather, GDNF appears to be essential for the survival or development the enteric nervous system and for the differentiation of the metanephric kidney and ureter from the caudal intermediate mesoderm.

Example 7
Anti-GDNF Monoclonal Antibodies

Five BALB/c mice (Charles River Laboratories, Wilmington, Del.) were hyperimmunized with purified rhGDNF in RIBI adjuvant (RIBI Immunochem Research, Inc., Hamilton, Mo.). Splenocytes from the mouse demonstrating the highest titer of antibody to immobilized rhGDNF were fused (Sierra BioSource, Inc., Gilroy, Calif.) with the mouse myeloma cells (SP2/0; American Type Culture Collection, Rockville, Md.). After 10–14 days, the supernatants were harvested and screened for antibody production and hGDNF specificity by enzyme-linked immunosorbent assay (ELISA). Fourteen positive clones showing the highest immunoreactivity after the second round of cloning were injected into Pristane-primed mice for in vivo production of MAb. The ascites fluids were pooled and purified by affinity chromatography (Pharmacia fast protein liquid chromatography [FPLC]; Pharmacia, Uppsala, Sweden) on staphylococcal protein A (Pharmacia). The purified antibody preparations were sterile filtered (0.2-$\mu$m pore size; Nalgene, Rochester, N.Y.) and stored at 4° C. in phosphate-buffered saline (PBS).

Microtiter plates were coated with 100 $\mu$l/well of rhGDNF or rhTGF-$\beta_1$ (Genentech, Inc.; 1 $\mu$g/mL) in 0.05 M carbonate buffer, pH 9.6, overnight at 4° C. Plates were washed three times with ELISA wash buffer (PBS/0.05% Tween 20) and blocked for at least 1 hr with PBS containing 0.5% bovine serum albumin and 0.05% Tween 20 (PBS/BSA/T20). The plates were washed again three times with wash buffer, and 100 $\mu$L of samples and controls were added for 1–2 hrs at ambient temperature. The plates were washed three times and incubated for 1–2 hrs at ambient temperature with HRP-conjugated goat anti-mouse IgG (Fc specific) (Sigma) diluted in PBS/BSA/20. The plates were then washed and incubated with orthophenylene diamine in PBS (Sigma; one 5 mg tablet per 12.5 mL of PBS; 100 $\mu$L/well) for 10–20 minutes at ambient temperature. The reaction was stopped with 2.5 N $H_2SO_4$. The resulting absorbances (490 nm using a 405 nm reference filter) were recorded using an automatic plate reader (UV Max, Molecular Devices, Palo Alto, Calif.).

The isoelectric points of the purified MAbs were determined using the Phast-System (Pharmacia), following manufactures procedures.

SDS-PAGE can be used for purity analysis and immunoblotting. One-dimensional SDS-PAGE was performed according to the method of Laemmli using 4–20% Trisglycine gels (Novex, Encinitas, Calif.). rhGDNF (1 $\mu$g per lane) and 5 $\mu$L of biotinylated molecular weight standards (Bio-Rad) were added to the appropriate gel lanes and electrophoresed at 125 V (approximately 32–35 mA) for 1.5–2 hr. The gels were used for immunoblotting. rhGDNF was diluted to 100 $\mu$g/mL in sample buffer (8% SDS-40% glycerol-350 mM Tris-HCI-273 mM Tris base, 0.5% [w/v] xylene cyanole, and 0.5% [w/v] bromphenol blue) in the presence (5% [v/v] $\beta$-mercaptoethanol) and absence of a reducing agent. Reduced samples were heated at 90° C. for 5 min.

Immunoblotting analysis was performed. After transfer, the membranes were blocked with PBS/BSA/T20 for at least 1 hr at ambient temperature, and incubated with the affinity-purified MAbs (diluted to 1 $\mu$g/mL in PBS/BSA/T20) for 1 hr at ambient temperature. The sheets were then washed with PBS-0.05% T20 and the appropriate HRP conjugates (rat anti-mouse IgG-HRP [Boehringer Mannheim], 1:5000; or streptavidin-HRP [Sigma, St. Louis, Mo.], 1:10,000; each diluted in PBS/BSA/T20) were added for 1 hr at ambient temperature. The sheets were then washed and exposed to luminol substrate (Amersham International, Amersham, UK) for 1 min at ambient temperature with agitation, and exposed to X-ray film (Eastman Kodak, Rochester, N.Y.) for approximately 15–60 sec.

Fourteen rhGDNF MAbs, of varying isotypes, capable of binding both immobilized rhGDNF and rhGDNF in solution were found. The MAbs do not crossreact with rhTGF$\beta_1$, and bind both non-reduced and reduced GDNF protein. Five (5) of the MAbs were suitable for immunohistochemical analysis. MAbs 1694, 1712, 1717, 1725 and 1731 are capable of binding GDNF complexed with its putative receptor. The other Mabs were designated 1693, 1695, 1696, 1709, 1710, 1711, 1713, 1714, 1715, and 1716. The designations are those assigned to the hybridoma producing each Mab. Epitope specificity of the MAbs can determined by cross-blocking analysis.

In summary, provided herein is a unique receptor system for GDNF, in which GDNFR$\alpha$, a novel GPI-linked protein, is a ligand-binding component and the tyrosine kinase receptor Ret is a signaling component. The GDNF receptor complex resembles in part the receptors for ciliary neurotrophic factor (Davis et al. *Science* 259:1736–1739 (1993)), bacterial endotoxin (Lee et al. *Proc. Natl. Acad. Sci. USA* 90:9930–9934 (1993); Pugin et al. *Proc. Nat. Acad. Sci. USA* 90:2744–2748 (1993)), and receptors in the immune system in which GPI-linked proteins serve as ligand binding components and cytoplasmic tyrosine kinases serves as the signaling components (Brown, *Curr. Opin. Immunol* 5:349–354(1993)). GDNF may represent an evolutionary transition within the super-family of the cysteine knot-containing proteins, from growth factors that use serine threonine kinase receptors (the TGF$\beta$ branch of this super-family) to growth factors that use tyrosine kinase receptors (the nerve growth factor and platelet-derived growth factor branches of this super family; McDonald et al. *Cell* 73:421–424 (1993). The identification of additional neuronal and non-neuronal cells and organs dependent on GDNF and the discovery of the receptor and associated receptor system for GDNF, presented herein, provide the means for modulating and controlling cell activity and survival. This provides additional and specific methods of treatment available to the clinician.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 2378 base pairs
       (B) TYPE: Nucleic Acid
       (C) STRANDEDNESS: Double
       (D) TOPOLOGY: Linear (xi) SEQUENCE DESCRIPTION: SEQ ID NO:1:

```
TTCTATCGAT TGAATTCCCC GGGGATCCTC TAGAGATCCC TCGACCTCGA              50

CCCACGCGTC CGCCGGGCGG CGGCTTTGGA TTTTGGGGGG GCGGGGACCA             100

GCTGCGCGGC GGCACC   ATG TTC CTA GCC ACT CTG TAC TTC                140
                    Met Phe Leu Ala Thr Leu Tyr Phe
                     1               5

GCG CTG CCA CTC CTG GAT TTG CTG ATG TCC GCC GAG GTG                179
Ala Leu Pro Leu Leu Asp Leu Leu Met Ser Ala Glu Val
     10              15                  20

AGT GGT GGA GAC CGT CTG GAC TGT GTG AAA GCC AGC GAT                218
Ser Gly Gly Asp Arg Leu Asp Cys Val Lys Ala Ser Asp
             25                  30

CAG TGC CTG AAG GAA CAG AGC TGC AGC ACC AAG TAC CGC                257
Gln Cys Leu Lys Glu Gln Ser Cys Ser Thr Lys Tyr Arg
 35                  40                  45

ACA CTA AGG CAG TGC GTG GCG GGC AAG GAA ACC AAC TTC                296
Thr Leu Arg Gln Cys Val Ala Gly Lys Glu Thr Asn Phe
         50                  55                  60

AGC CTG ACA TCC GGC CTT GAG GCC AAG GAT GAG TGC CGT                335
Ser Leu Thr Ser Gly Leu Glu Ala Lys Asp Glu Cys Arg
                 65                  70

AGC GCC ATG GAG GCC TTG AAG CAG AAG TCT CTG TAC AAC                374
Ser Ala Met Glu Ala Leu Lys Gln Lys Ser Leu Tyr Asn
         75                  80                  85

TGC CGC TGC AAG CGG GGC ATG AAG AAA GAG AAG AAT TGT                413
Cys Arg Cys Lys Arg Gly Met Lys Lys Glu Lys Asn Cys
                 90                  95

CTG CGT ATC TAC TGG AGC ATG TAC CAG AGC CTG CAG GGA                452
Leu Arg Ile Tyr Trp Ser Met Tyr Gln Ser Leu Gln Gly
100                 105                 110

AAT GAC CTC CTG GAA GAT TCC CCG TAT GAG CCG GTT AAC                491
Asn Asp Leu Leu Glu Asp Ser Pro Tyr Glu Pro Val Asn
        115                 120                 125

AGC AGG TTG TCA GAT ATA TTC CGG GCA GTC CCG TTC ATA                530
Ser Arg Leu Ser Asp Ile Phe Arg Ala Val Pro Phe Ile
                130                 135

TCA GAT GTT TTC CAG CAA GTG GAA CAC ATT TCC AAA GGG                569
Ser Asp Val Phe Gln Gln Val Glu His Ile Ser Lys Gly
        140                 145                 150

AAC AAC TGC CTG GAC GCA GCC AAG GCC TGC AAC CTG GAC                608
Asn Asn Cys Leu Asp Ala Ala Lys Ala Cys Asn Leu Asp
                155                 160

GAC ACC TGT AAG AAG TAC AGG TCG GCC TAC ATC ACC CCC                647
Asp Thr Cys Lys Lys Tyr Arg Ser Ala Tyr Ile Thr Pro
165                 170                 175

TGC ACC ACC AGC ATG TCC AAC GAG GTC TGC AAC CGC CGT                686
```

-continued

| | | | | | | | | | | |
|---|---|---|---|---|---|---|---|---|---|---|
| Cys | Thr | Thr | Ser | Met | Ser | Asn | Glu | Val | Cys | Asn | Arg | Arg |
| | | 180 | | | | 185 | | | | 190 |

```
AAG TGC CAC AAG GCC CTC AGG CAG TTC TTC GAC AAG GTT         725
Lys Cys His Lys Ala Leu Arg Gln Phe Phe Asp Lys Val
            195                 200

CCG GCC AAG CAC AGC TAC GGG ATG CTC TTC TGC TCC TGC         764
Pro Ala Lys His Ser Tyr Gly Met Leu Phe Cys Ser Cys
205             210                 215

CGG GAC ATC GCC TGC ACC GAG CGG CGG CGA CAG ACT ATC         803
Arg Asp Ile Ala Cys Thr Glu Arg Arg Arg Gln Thr Ile
            220                 225

GTC CCC GTG TGC TCC TAT GAA GAA CGA GAG AGG CCC AAC         842
Val Pro Val Cys Ser Tyr Glu Glu Arg Glu Arg Pro Asn
230             235                 240

TGC CTG AGT CTG CAA GAC TCC TGC AAG ACC AAT TAT ATC         881
Cys Leu Ser Leu Gln Asp Ser Cys Lys Thr Asn Tyr Ile
            245                 250             255

TGC AGA TCT CGC CTT GCA GAT TTT TTT ACC AAC TGC CAG         920
Cys Arg Ser Arg Leu Ala Asp Phe Phe Thr Asn Cys Gln
                260                 265

CCA GAG TCA AGG TCT GTC AGC AAC TGT CTT AAG GAG AAC         959
Pro Glu Ser Arg Ser Val Ser Asn Cys Leu Lys Glu Asn
        270                 275                 280

TAC GCA GAC TGC CTC CTG GCC TAC TCG GGA CTG ATT GGC         998
Tyr Ala Asp Cys Leu Leu Ala Tyr Ser Gly Leu Ile Gly
                285                 290

ACA GTC ATG ACT CCC AAC TAC GTA GAC TCC AGC AGC CTC        1037
Thr Val Met Thr Pro Asn Tyr Val Asp Ser Ser Ser Leu
295                 300                 305

AGC GTG GCA CCA TGG TGT GAC TGC AGC AAC AGC GGC AAT        1076
Ser Val Ala Pro Trp Cys Asp Cys Ser Asn Ser Gly Asn
        310                 315                 320

GAC CTG GAA GAC TGC TTG AAA TTT CTG AAT TTT TTT AAG        1115
Asp Leu Glu Asp Cys Leu Lys Phe Leu Asn Phe Phe Lys
                325                 330

GAC AAT ACT TGT CTC AAA AAT GCA ATT CAA GCC TTT GGC        1154
Asp Asn Thr Cys Leu Lys Asn Ala Ile Gln Ala Phe Gly
        335                 340                 345

AAT GGC TCA GAT GTG ACC ATG TGG CAG CCA GCC CCT CCA        1193
Asn Gly Ser Asp Val Thr Met Trp Gln Pro Ala Pro Pro
                350                 355

GTC CAG ACC ACC ACT GCC ACC ACT ACT ACT GCC TTC CGG        1232
Val Gln Thr Thr Thr Ala Thr Thr Thr Thr Ala Phe Arg
360                 365                 370

GTC AAG AAC AAG CCT CTG GGG CCA GCA GGG TCT GAG AAT        1271
Val Lys Asn Lys Pro Leu Gly Pro Ala Gly Ser Glu Asn
        375                 380                 385

GAG ATC CCC ACA CAC GTT TTA CCA CCC TGT GCG AAT TTG        1310
Glu Ile Pro Thr His Val Leu Pro Pro Cys Ala Asn Leu
                390                 395

CAG GCT CAG AAG CTG AAA TCC AAT GTG TCG GGT AGC ACA        1349
Gln Ala Gln Lys Leu Lys Ser Asn Val Ser Gly Ser Thr
400                 405                 410

CAC CTC TGT CTT TCT GAT AGT GAT TTC GGA AAG GAT GGT        1388
His Leu Cys Leu Ser Asp Ser Asp Phe Gly Lys Asp Gly
                415                 420

CTC GCT GGT GCC TCC AGC CAC ATA ACC ACA AAA TCA ATG        1427
Leu Ala Gly Ala Ser Ser His Ile Thr Thr Lys Ser Met
425                 430                 435
```

```
GCT GCT CCT CCC AGC TGC AGT CTG AGC TCA CTG CCG GTG           1466
Ala Ala Pro Pro Ser Cys Ser Leu Ser Ser Leu Pro Val
        440                 445                 450

CTG ATG CTC ACC GCC CTT GCT GCC CTG TTA TCT GTA TCG           1505
Leu Met Leu Thr Ala Leu Ala Ala Leu Leu Ser Val Ser
            455                 460

TTG GCA GAA ACG TCG  TAGCTGCATC CGGGAAAACA GTATGAAAAG         1550
Leu Ala Glu Thr Ser
    465         468

ACAAAGAGA ACCAAGTATT CTGTCCCTGT CCTCTTGTAT ATCTGAAAAT         1600

CCAGTTTTAA AAGCTCCGTT GAGAAGCAGT TTCACCCAAC TGGAACTCTT        1650

TCCTTGTTTT TAAGAAAGCT TGTGGCCCTC AGGGGCTTCT GTTGAAGAAC        1700

TGCTACAGGG CTAATTCCAA ACCCATAAGG CTCTGGGGCG TGGTGCGGCT        1750

TAAGGGGACC ATTTGCACCA TGTAAAGCAA GCTGGGCTTA TCATGTGTTT        1800

GATGGTGAGG ATGGTAGTGG TGATGATGAT GGTAATTTTA ACAGCTTGAA        1850

CCCTGTTCTC TCTACTGGTT AGGAACAGGA GATACTATTG ATAAAGATTC        1900

TTCCATGTCT TACTCAGCAG CATTGCCTTC TGAAGACAGG CCCGCAGCCT        1950

AGTGTGAATG ACAAGTGGAG GTTGGCCTCA AGAGTGGACT TGGCAGACTC        2000

TACCTTGTAG TAATGTTCAC CTTTCCGTGT ATGGTCTCCA CAGAGTGTTT        2050

ATGTATTTAC AGACTGTTCT GTGATCCCCC AACAACAACA ACCACAAATT        2100

CCTTGGTCAC CTCCAAATGT AACCGGTCCT TTAGCCCAGT AGAGGAGGGT        2150

GGGTGTGGCC CTGGCACAGC TCCCGGATTG TTGATGGGCA CTCTCCTGAG        2200

CTTTGCTTGA GTGAGAAGCT GAATGTAGCT GAAAATCAAC TCTTCTTACA        2250

CTTAAAAAAA AAAAAAAAAA AAAAAAAAAA AAAAAAAAAA AAAAAAAAA         2300

AAAAAAAAAA AAAAGGTTTA GGGATAACAG GGTAATGCGG CCGCGTCGAC        2350

CTGCAGAAGC TTGGCCGCCA TGGCCCAA                                2378

(2) INFORMATION FOR SEQ ID NO:2:

(i) SEQUENCE CHARACTERISTICS:
        (A) LENGTH: 468 amino acids
        (B) TYPE: Amino Acid
        (D) TOPOLOGY: Linear (ix) FEATURE:
        (A) NAME/KEY: Extracellular Domain
        (B) LOCATION: 25
        (C) IDENTIFICATION METHOD:
        (D) OTHER INFORMATION:

(ix) FEATURE:
        (A) NAME/KEY: Mature Protein N-terminal
        (B) LOCATION: 25-427
        (C) IDENTIFICATION METHOD:
        (D) OTHER INFORMATION:

(ix) FEATURE:
        (A) NAME/KEY: Potential Glycosolation Site
        (B) LOCATION: 349
        (C) IDENTIFICATION METHOD:
        (D) OTHER INFORMATION:

(ix) FEATURE:
        (A) NAME/KEY: Potential Glycosolation Site
        (B) LOCATION: 408
        (C) IDENTIFICATION METHOD:
        (D) OTHER INFORMATION:

(ix) FEATURE:
```

(A) NAME/KEY: Potential Glycosolation Site
(B) LOCATION: 61
(C) IDENTIFICATION METHOD:
(D) OTHER INFORMATION:

(xi) SEQUENCE DESCRIPTION: SEQ ID NO:2:

```
Met Phe Leu Ala Thr Leu Tyr Phe Ala Leu Pro Leu Leu Asp Leu
 1               5                  10                  15

Leu Met Ser Ala Glu Val Ser Gly Gly Asp Arg Leu Asp Cys Val
                20                  25                  30

Lys Ala Ser Asp Gln Cys Leu Lys Glu Gln Ser Cys Ser Thr Lys
                35                  40                  45

Tyr Arg Thr Leu Arg Gln Cys Val Ala Gly Lys Glu Thr Asn Phe
                50                  55                  60

Ser Leu Thr Ser Gly Leu Glu Ala Lys Asp Glu Cys Arg Ser Ala
                65                  70                  75

Met Glu Ala Leu Lys Gln Lys Ser Leu Tyr Asn Cys Arg Cys Lys
                80                  85                  90

Arg Gly Met Lys Lys Glu Lys Asn Cys Leu Arg Ile Tyr Trp Ser
                95                 100                 105

Met Tyr Gln Ser Leu Gln Gly Asn Asp Leu Leu Glu Asp Ser Pro
               110                 115                 120

Tyr Glu Pro Val Asn Ser Arg Leu Ser Asp Ile Phe Arg Ala Val
               125                 130                 135

Pro Phe Ile Ser Asp Val Phe Gln Gln Val Glu His Ile Ser Lys
               140                 145                 150

Gly Asn Asn Cys Leu Asp Ala Ala Lys Ala Cys Asn Leu Asp Asp
               155                 160                 165

Thr Cys Lys Lys Tyr Arg Ser Ala Tyr Ile Thr Pro Cys Thr Thr
               170                 175                 180

Ser Met Ser Asn Glu Val Cys Asn Arg Arg Lys Cys His Lys Ala
               185                 190                 195

Leu Arg Gln Phe Phe Asp Lys Val Pro Ala Lys His Ser Tyr Gly
               200                 205                 210

Met Leu Phe Cys Ser Cys Arg Asp Ile Ala Cys Thr Glu Arg Arg
               215                 220                 225

Arg Gln Thr Ile Val Pro Val Cys Ser Tyr Glu Glu Arg Glu Arg
               230                 235                 240

Pro Asn Cys Leu Ser Leu Gln Asp Ser Cys Lys Thr Asn Tyr Ile
               245                 250                 255

Cys Arg Ser Arg Leu Ala Asp Phe Phe Thr Asn Cys Gln Pro Glu
               260                 265                 270

Ser Arg Ser Val Ser Asn Cys Leu Lys Glu Asn Tyr Ala Asp Cys
               275                 280                 285

Leu Leu Ala Tyr Ser Gly Leu Ile Gly Thr Val Met Thr Pro Asn
               290                 295                 300

Tyr Val Asp Ser Ser Ser Leu Ser Val Ala Pro Trp Cys Asp Cys
               305                 310                 315

Ser Asn Ser Gly Asn Asp Leu Glu Asp Cys Leu Lys Phe Leu Asn
               320                 325                 330

Phe Phe Lys Asp Asn Thr Cys Leu Lys Asn Ala Ile Gln Ala Phe
               335                 340                 345

Gly Asn Gly Ser Asp Val Thr Met Trp Gln Pro Ala Pro Val
               350                 355                 360
```

```
Gln Thr Thr Thr Ala Thr Thr Thr Ala Phe Arg Val Lys Asn
            365                 370                 375

Lys Pro Leu Gly Pro Ala Gly Ser Glu Asn Glu Ile Pro Thr His
            380                 385                 390

Val Leu Pro Pro Cys Ala Asn Leu Gln Ala Gln Lys Leu Lys Ser
            395                 400                 405

Asn Val Ser Gly Ser Thr His Leu Cys Leu Ser Asp Ser Asp Phe
            410                 415                 420

Gly Lys Asp Gly Leu Ala Gly Ala Ser Ser His Ile Thr Thr Lys
            425                 430                 435

Ser Met Ala Ala Pro Pro Ser Cys Ser Leu Ser Ser Leu Pro Val
            440                 445                 450

Leu Met Leu Thr Ala Leu Ala Ala Leu Leu Ser Val Ser Leu Ala
            455                 460                 465

Glu Thr Ser (2) INFORMATION FOR SEQ ID NO:3:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:3:

His Gln Asn Leu Ser Asp Gly Lys
 1               5

(2) INFORMATION FOR SEQ ID NO:4:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:4:

His Gln Asn Ile Ser Asp Gly Lys
 1               5

(2) INFORMATION FOR SEQ ID NO:5:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:5:

His Gln Ser Leu Gly Thr Gln
 1               5

(2) INFORMATION FOR SEQ ID NO:6:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:6:

Val Ile Ser Ser His Leu Gly Gln
 1               5

(2) INFORMATION FOR SEQ ID NO:7:

(i) SEQUENCE CHARACTERISTICS:
```

(A) LENGTH: 11 amino acids
(B) TYPE: Amino Acid
(D) TOPOLOGY: Linear (xi) SEQUENCE DESCRIPTION: SEQ ID NO:7:

Pro Lys Asn Ser Ser Met Ile Ser Asn Thr Pro
 1               5                  10

(2) INFORMATION FOR SEQ ID NO:8:

(i) SEQUENCE CHARACTERISTICS:
        (A) LENGTH: 418 base pairs
        (B) TYPE: Nucleic Acid
        (C) STRANDEDNESS: Single
        (D) TOPOLOGY: Linear (xi) SEQUENCE DESCRIPTION: SEQ ID NO:8:

| | |
|---|---|
| CCGGCACTGA ATCTAGGAAG GAGCCCAGGA TGAGCGGCAG GTTGGGTCGG | 50 |
| AACTGAACCC CTAAAAGCGG GTCCGCCTCC CGCCCTCGCG CCCGCTCGGA | 100 |
| GCTGAGTCCC TGGCGGCGGT GGGCGGCAGA GCAACGGGGA GTCTGCTCTC | 150 |
| ACCCTGGATG GAGCTTAACT TTGAGTGGCC AGAGGAGCGC AGTCGCCCGG | 200 |
| GGATCTCTGC ACGCTGAGCT CTCTCCGCGA GATCCGGTGG CGGCTTTGGA | 250 |
| TTTTGGGGGG GCGGGGACCA GCTGCGCGGT GGCACCATGT TCCTAGCCAC | 300 |
| TCTGTACTTC GTGCTGCCAC TCCTGGATTT GCTGATGTCG GCCGAGGTGA | 350 |
| GTGGTGGGGA CCGCCTGGAC TGTGTGAAAG CCAGTGATCA GTGCCTGAAG | 400 |
| GAACAGAGCT GCAGCACC | 418 |

(2) INFORMATION FOR SEQ ID NO:9:

(i) SEQUENCE CHARACTERISTICS:
        (A) LENGTH: 840 base pairs
        (B) TYPE: Nucleic Acid
        (C) STRANDEDNESS: Single
        (D) TOPOLOGY: Linear (xi) SEQUENCE DESCRIPTION: SEQ ID NO:9:

| | |
|---|---|
| CGCCGCAAGT GCCACAAAGC CCTCAGGCAG TTCTTCGACA AAGTTCCAGC | 50 |
| CAAGCACAGC TACGGGATGC TCTTCTGCTC CTGCCGGGAC GTCGCCTGCA | 100 |
| CCGAGAGGCG CGCGACAGACT ATCGTCCCTG TGTGCTCCTA TGAAGAACGA | 150 |
| GAGAGGCCCA ACTGCCTGAA TCTGCAAGAC TCCTGCAAGA CAAATTACAT | 200 |
| CTGCAGATCT CGCCTTGCAG ATTTTTTTAC CAACTGCCAG CCAGAGTCAA | 250 |
| GGTCTGTCAG CAACTGTCTT AAGGAGAACT ACGCAGACTG CCTCCTGGCC | 300 |
| TACTCGGGAC TGATTGGCAC AGTCATGACT CCTAACTACA TAGACTCCAG | 350 |
| CAGCCTCAGT GTGGCGCCGT GGTGCGATTG CAGCAACAGT GGCAATGACC | 400 |
| TGGAAGATTG CCTGAAGTTT CTGAATTTTT TTAAGGACAA TACGTGTCTC | 450 |
| AAAAATGCAA TTCAAGCCTT TGGCAATGGC TCGGATGTGA CCATGTGGCA | 500 |
| GCCAGCCCCC CCAGTCCAGA CCACCACTGC CACGACTACC ACTGCCTTCC | 550 |
| GGATCAAGAA CAAGCCTCTA GGGCCAGCAG GCTCTGAGAA TGAGATTCCC | 600 |
| ACACACGTTT TACCACCGTG TGCTAATTTG CAGGCACAGA AGCTGAAATC | 650 |
| CAATGTATCG GGCAGTACAC ATCTCTGTCT TTCTGATAAT GATTACGGAA | 700 |
| AGGATGGTCT CGCTGGTGCC TCCAGCCACA TAACCACAAA ATCAATGGCT | 750 |

```
GCTCCTCCCA GCTGCGGTCT GAGCTCACTG CCGGTGATGG TGTTCACCGC         800

TCTGGCTGCC CTGTTGTCTG TATCATTGGC AGAAACATCG                    840
```

(2) INFORMATION FOR SEQ ID NO:10:

(i) SEQUENCE CHARACTERISTICS:
        (A) LENGTH: 351 base pairs
        (B) TYPE: Nucleic Acid
        (C) STRANDEDNESS: Single
        (D) TOPOLOGY: Linear (xi) SEQUENCE DESCRIPTION: SEQ ID NO:10:

```
AGGGAATTTG GCCCTCGAGG AAGGAGATTC GGCACGAGGC CAAGAGCAAC          50

CATTGCCTGG ATGCTGCCAA GGCCTGCAAC CTGAATGACA ACTGCAAGAA         100

GCTGCGCTCC TCCTACATCT CCATCTGCAA CCGCGAGATC TCGCCCACCG         150

AGCGCTGCAA CCGCCGCAAG TGCCACAAGG CCCTGCGCCA GTTCTTCGAC         200

CGGGTGCCCA GCGAGTACAC CTACCGCATG CTCTTCTGCT CCTGCCAAGA         250

TCAGGCGTGC GCTGAGCNCG CGGNCAAAAC CATCCTGCCC AGCTGCTCCT         300

ATGAGGACAA GGAGAAGCCC AACTGCNTGG ACNTGCGTGG CGTGTGCCGG         350

A                                                              351
```

(2) INFORMATION FOR SEQ ID NO:11:

(i) SEQUENCE CHARACTERISTICS:
        (A) LENGTH: 453 base pairs
        (B) TYPE: Nucleic Acid
        (C) STRANDEDNESS: Single
        (D) TOPOLOGY: Linear (xi) SEQUENCE DESCRIPTION: SEQ ID NO:11:

```
GCAACCATTG CCTGGATGCT GCCAAGGCCT GCAACCTGAA TGACAACTGC          50

AAGAAGCTGC GCTCCTCCTA CATCTCCATC TGCAACCGCG AGATCTCGCC         100

CACCGAGCGC TGCAACCGCC GCAAGTGCCA CAAGGCCCTG CGCCAGTTCT         150

TCGACCGGGT GCCCAGCGAG TACACCTACC GCATGCTCTT CTGCTCCTGC         200

CAAGACCAGG CGTGCGCTGA GCGCGCGGGC AAAACCATCC TGCCCAGCTG         250

CTCCTATGAG GACAAGGAGA AGCCCAACTG CCTGGACCTG CGTGGCGTGT         300

GCCGGACTGA CCACCTGTGT CGGTCCCGGC TNGCCGACTT TCCATGCCAA         350

TTTGTTCGAG CCTTCCTACC AGACGGGTCA CCAGGCTGCC CTNGCGGACA         400

ATTTACCAGG GCGTGTCTTG GGGTCTTNAT GTTGGCATGA TTGGGTTTGA         450

CAT                                                            453
```

(2) INFORMATION FOR SEQ ID NO:12:

(i) SEQUENCE CHARACTERISTICS:
        (A) LENGTH: 201 base pairs
        (B) TYPE: Nucleic Acid
        (C) STRANDEDNESS: Single
        (D) TOPOLOGY: Linear -continued (xi) SEQUENCE DESCRIPTION: SEQ ID NO:12:

| | | | | |
|---|---|---|---|---|
| GCAACCATTG | CCTGGATGCT | GCCAAGGCCT | GCAACCTGAA | TGACAACTGC | 50 |
| AAGAAGCTGC | GCTCCTCCTA | CATCTCCATC | TGCAACCGCG | AGATCTCGCC | 100 |
| CACCGAGCGC | TGCAACCGCC | GCAAGTGCCA | CAAGGCCCTG | CGCCAGTTCT | 150 |
| TCGACCGGGT | GCCCAGCGAG | TACACCTACC | GCATGCTCTT | CTGCTCCTGC | 200 |
| C | | | | | 201 |

What is claimed is:

1. An isolated polypeptide comprising a GDNFRα extracellular domain having the amino acid sequence as set out between amino acids Asp25 and Gly427 cf SEQ ID NO:2.

2. An isolated polypeptide comprising mature GDNFRα having the amino acid sequence as set out between amino acids Asp25 and Ser468 of SEQ ID NO:2.

* * * * *